United States Patent
Pike et al.

(10) Patent No.: US 12,419,871 B2
(45) Date of Patent: Sep. 23, 2025

(54) BIOMOLECULES INVOLVED IN ALZHEIMER'S DISEASE

(71) Applicant: ELECTROPHORETICS LIMITED, London (GB)

(72) Inventors: Ian Hugo Pike, Cobham (GB); Malcolm Andrew Ward, Cobham (GB); Claire Louise Russell, Cobham (GB); Vikram Mitra, Cobham (GB)

(73) Assignee: ELECTROPHORETICS LIMITED, Cobham (GB)

( * ) Notice: Subject to any disclaimer, the term of this patent is extended or adjusted under 35 U.S.C. 154(b) by 0 days.

(21) Appl. No.: 15/577,522

(22) PCT Filed: May 27, 2016

(86) PCT No.: PCT/EP2016/062090
§ 371 (c)(1),
(2) Date: Nov. 28, 2017

(87) PCT Pub. No.: WO2016/189163
PCT Pub. Date: Dec. 1, 2016

(65) Prior Publication Data
US 2018/0140585 A1    May 24, 2018

(30) Foreign Application Priority Data

May 28, 2015  (GB) ..................................... 1509134
Jul. 17, 2015  (GB) ..................................... 1512596

(51) Int. Cl.
| | | |
|---|---|---|
| A61K 31/437 | (2006.01) | |
| A61K 31/13 | (2006.01) | |
| A61K 31/445 | (2006.01) | |
| A61K 31/55 | (2006.01) | |
| A61K 31/57 | (2006.01) | |
| A61P 25/28 | (2006.01) | |
| C07K 14/47 | (2006.01) | |
| C12N 9/16 | (2006.01) | |
| G01N 33/68 | (2006.01) | |

(52) U.S. Cl.
CPC ............ *A61K 31/437* (2013.01); *A61K 31/13* (2013.01); *A61K 31/445* (2013.01); *A61K 31/55* (2013.01); *A61K 31/57* (2013.01); *A61P 25/28* (2018.01); *C07K 14/4711* (2013.01); *C12N 9/16* (2013.01); *G01N 33/6896* (2013.01); *G01N 2800/2821* (2013.01); *G01N 2800/50* (2013.01); *G01N 2800/56* (2013.01)

(58) Field of Classification Search
CPC .... A61K 31/437; A61K 31/13; A61K 31/445; A61K 31/55; A61K 31/57; A61P 25/28; C07K 14/4711; C12N 9/16; G01N 33/6896; G01N 2800/2821; G01N 2800/50; G01N 2800/56
See application file for complete search history.

(56) References Cited

U.S. PATENT DOCUMENTS

| | | |
|---|---|---|
| 4,376,110 A | 3/1983 | David et al. |
| 4,946,778 A | 8/1990 | Ladner et al. |
| 2004/0106120 A1 | 6/2004 | Tazi-Ahnini et al. |
| 2013/0237454 A1 | 9/2013 | Schutzer |
| 2017/0285010 A1 | 10/2017 | Lindstedt et al. |
| 2018/0067133 A1 | 3/2018 | Pike et al. |

FOREIGN PATENT DOCUMENTS

| | | |
|---|---|---|
| AU | 2012258339 A1 | 6/2013 |
| JP | 2002523461 A | 7/2002 |
| JP | 2004524010 A | 8/2004 |
| JP | 2013121956 A | 6/2013 |
| JP | 2018505655 A | 3/2018 |
| JP | 2018510343 A | 4/2018 |
| WO | 0012093 A1 | 3/2000 |
| WO | 0153312 A1 | 7/2001 |
| WO | WO 2005/067391 A2 | 7/2005 |
| WO | WO 2006/083854 A2 | 8/2006 |
| WO | 2011005893 A2 | 1/2011 |
| WO | WO 2012/080727 A2 | 6/2012 |
| WO | WO 2012/080729 A2 | 6/2012 |

OTHER PUBLICATIONS

McAvoy et al. Clinical Chem., 2014, 60(4):683-9.*
Aljo, T. et al.; "An integrative computational systems biology approach identifies differentially regulated dynamic transcriptome signatures which drive the initiation of human T helper cell differentiation"; BMC Genomics; vol. 13; No. 572; 20 pages.
Ali, D. et al.; "694—Identification of novel epigenetic biomarkers in colorectal cancer, GLDC and PPP1R14A"; European Journal of Cancer Supplements; vol. 8; No. 5; Jun. 1, 2010; p. 175.
Aluise, C. D. et al.; "Peptides and Proteins in Plasma and Cerebrospinal Fluid as Biomarkers for the Prediction, Diagnosis, and Monitoring of Therapeutic Efficacy of Alzheimer's Disease"; Biochim Biophys Acta.; vol. 1782; No. 10; 2008; pp. 549-558.
Atluri, VSR et al.; "Differential Effects o HIV-1B and HIV-1C Infection on Synaptic Plasticity Genes: Implication in HIV-associated Neurocognitive Disorders"; Journal of Neuroimmune Pharmacology; vol. 7; Suppl. 1; 2012; p. S29.

(Continued)

*Primary Examiner* — Olga N Chernyshev
(74) *Attorney, Agent, or Firm* — ArentFox Schiff LLP

(57) ABSTRACT

The invention relates to panels of biomarkers including proteins phosphatase 1 regulatory subunit 14A and/or 2',3'-cyclic-nucleotide 3'-phosphodiesterase and/or phosphorylated tau or fragments thereof and methods using thereof for diagnosing, staging, treating and assessing the response of a treatment for a neurocognitive disorder characterised by tau toxicity, in particular for Alzheimer's disease. The present invention shows that the biomarkers disclosed herein are elevated in the brain of subjects with an advanced stage of a neurocognitive disorder (Braak stage V/VI) and/or are regulated in the CSF of AD subjects in comparison to cognitively affected non-AD controls; and/or regulated in response to two casein kinase 1 delta inhibitors.

17 Claims, 7 Drawing Sheets

Specification includes a Sequence Listing.

(56) References Cited

OTHER PUBLICATIONS

Bird, R. E. et al.; "Single-Chain Antigen-Binding Proteins"; Science; vol. 242; Oct. 21, 1988; pp. 423-426.
Braak, H. et al.; "Neuropathological stageing of Alzheimer-related changes"; Acta Neuropathol; vol. 82; 1991; pp. 239-259.
Brown, L. A. et al.; "The role of tau protein in HIV-associated neurocognitive disorders"; Molecular Neurodegeneration; vol. 9; Article 40; 2014; 9 pages.
Cole, S.P.C. et al.; "The EBV-Hybridoma Technique and Its Application To Human Lung Cancer"; Monoclonal Antibodies and Cancer Therapy; Alan R. Liss, Inc.; 1985; pp. 77-96.
Cote, R. J. et al.; "Generation of human monoclonal antibodies reactive with cellular antigens"; Proc. Natl. Acad. Sci., USA; vol. 80; Apr. 1983; pp. 2026-2030.
Ferreira, D. et al.; "Meta-review of CSF core biomakers in Alzheimer's disease: the state-of-the-art after the new revised diagnostic criteria"; Frontiers In Aging Neuroscience: vol. 6; Mar. 2014; 24 pages.
GB Search Report issued for GB Application No. 1509134.1, date of search Feb. 24, 2016; 7 pages.
GB Search Report issued for GB Application No. 1512596.6, date of search May 6, 2016; 6 pages.
Huse, W. D. et al.; "Generation of a Large Combinatorial Library of the Immunoglobulin Repertoire in Phage Lambda"; Science; vol. 246; Dec. 8, 1989; pp. 1275-1281.
Huston, J. S. et al.; "Protein engineering of antibody binding sites: Recovery of specific activity in an anti-digoxin single-chain Fv analogue produced in *Escherichia coli*"; Proc. Natl. Acad. Sci. USA; vol. 85; Aug. 1988; pp. 5879-5883.
International Search Report issued for PCT/EP2016/062090, date of mailing Sep. 28, 2016; 4 pages.
Köhler, G. et al.; "Continuous cultures of fused cells secreting antibody of predefined specificity"; Nature; vol. 256; Aug. 7, 1975; pp. 495-497.
Kozbor, D. et al.; "The production of monoclonal antibodies from human lymphocytes"; Immunology Today: vol. 4; No. 3; 1983; pp. 72-79.
Li, M. D. et al.; "Integrated multi-cohort transcriptional meta-analysis of neurodegenerative diseases"; Acta Neuropatholgica Communications: vol. 2; 2014; 23 pages.
Li, X. et al.; "Ratio of AB42/P-tau181p in CSF Is associated with aberrant default mode network in AD"; Scientific Reports; vol. 3; Feb. 26, 2013; 5 pages.
Morrison, S. L. et al.; "Chimeric human antibody molecules: Mouse antigen-binding domains with human constant region domains"; Proc. Natl. Acad. Sci. USA; vol. 81; Nov. 1984; pp. 6851-6855.
Musunuri, S. et al.; "Quantification of the Brain Proteome in Alzheimer's Disease Using Multiplexed Mass Spectrometry"; Journal of Proteome Research; vol. 13; Mar. 10, 2014; pp. 2056-2068.
Nägga, K. et al.; "Cerebrospinal Fluid Phospho-Tau, Total Tau and β-Amyloid1-42 in the Differentiation between Alzheimer's Disease and Vascular Dementia"; Dementia and Geriatric Cognitive Disorders; vol. 14; 2002; pp. 183-190.
Neuberger, M. S. et al.; "Recombinant antibodies possessing novel effector functions"; Nature; vol. 312; Dec. 13, 1984; pp. 604-608.
Takeda, S. et al.; "Construction of chimaeric processed immunoglobulin genes containing mouse variable and human constant region sequences"; Nature; vol. 314; Apr. 4, 1985; pp. 452-454.
Ward, E. S. et al.; "Binding activities of a repertoire of single immunoglobulin variable domains secreted from *Escherichia coli*"; Letters to Nature; vol. 341; Oct. 12, 1989; pp. 544-546.
Yamawaki, K. et al.; "Identification of Human CPI-17, an Inhibitory Phosphoprotein for Myosin Phosphatase"; Biochemical and Biophysical Research Communciations; vol. 285; No. 4; 2001; pp. 1040-1045.
Zetterberg, H. et al.; "Cerebrospinal Fluid Biomarkers for Alzheimer's Disease: More to Come?"; Journal of Alzheimer's Disease: vol. 33; 2013; pp. S361-S369.
Japanese Office Action issued for JP Application No. 2017-561625, dated Apr. 28, 2020 (8 pages), and English translation of Pertinent Portion of Japanese Office Action (12 pages).
Braithwaite, S, et al.; "Protein Phosphatases and Alzheimer's Disease"; Prog Mol Biol Transl Sci., 2012, vol. 106, pp. 343-379 (32 pages).
EP Examination Report issued for EP Application No. 16 725 537.1, dated Jun. 15, 2021 (11 pages).
Tagawa, K. et al.; "Comprehensive phosphoproteome analysis unravels the core signaling network that initiates the earliest synapse pathology in preclinical Alzheimer's disease brain"; Human Molecular Genetics, vol. 24, No. 2, Sep. 17, 2014, pp. 540-558 (19 pages).
Canadian Office Action issued for Canadian Patent Application No. 2,986,826, dated Feb. 11, 2022 (4 pages).
C.-X. Gong et al.;"Post-translational modifications of tau protein in Alzheimer's disease"; J Neural Transm, 2005, vol. 112, pp. 813-838.
C.-X. Gong et al.; "Hyperphosphorylation of Microtubule-Associated Protein Tau: A Promising Therapeutic Target for Alzheimer Disease"; Curr Med Chem., 2008, vol. 15 No. 23, pp. 2321-2328.
Thomas McAvoy et al.; "Quantification of Tau in Cerebrospinal Fluid by Immunoaffinity Enrichment and Tandem Mass Spectrometry"; Clinical Chemistry, 2014, vol. 60 No. 4, pp. 683-689.
Roman Vlkolinsky et al.; "Decreased brain levels of 2',3'-cyclic nucleotide-3'-phosphodiesterase in Down syndrome and Alzheimer's disease"; Neurobiology of Aging, 2001, vol. 22, pp. 547-553.
Michael Fountoulakis et al.; Proteomics-driven progress in neurodegeneration research, Electrophoresis, 2006, vol. 27, pp. 1556-1573.
Christopher D. Aluise et al.; "Peptides and proteins in plasma and cerebrosipinal fluid as biomarkers for the prediction, diagnosis, and monitoring of the therapeutic efficacy of Alzheimer's disease"; Biochimica et Biophysica Acta, Aug. 7, 2008, vol. 1782 No. 10, pp. 549-558.
Henrik Zetterberg et al.; "Cerebrospinal Fluid Biomarkers for Alzheimer's Disease: More to Come?"; Journal of Alzheimer's Disease, 2013, vol. 33, pp. S361-S369.
Japanese Office Action issued for Japanese Patent Application No. 2021-005131, date of Japanese Office Action is Mar. 15, 2022 (11 pages) and English translation (10 pages).
Sayuri Taniguchi-Watanabe et al.; "Biochemical classification of tauopathies by immunoblot, protein sequence and mass spectrometric analyses of sarkosyl-insoluble and trypsin-resistant tau"; Acta Neuropathol, 2016, vol. 131, pp. 267-280.
Akihiko Takashima; "dementia, and the Tou protein"; Saitama Medical School magazine, Mar. 2017, vol. 43, No. 2, pp. 134-141. (English Machine translation of description from pp. 136-137).
Canadian Office Action issued in CA Application No. 2,986,826, dated Oct. 3, 2022.
Japanese Office Action issued in JP Application No. 2021-005131, dated Nov. 8, 2022 (English translation attached).
Yamawaki, Koji et al.; Identification of Human CPI-17, an Inhibitory Phosphoprotein for Myosin Phosphatase; Biochemical and Biophysical Research Communications, vol. 285, No. 4, 2001, pp. 1040-1045.
European Patent Office Communication pursuant to Article 94(3) EPC issued for EP Application No. 16 725 537.1-1118, dated May 9, 2023 (11 pages).
Gomez, Yassel Ramos et al.; "Characterization of Protein Complexes Using Targeted Proteomics"; Current Topics in Medicinal Chemistry, 2014, vol. 14, No. 3, pp. 1-8.
Zhao, Yingxin et al.; "Applications Of Selected Reaction Monitoring (SRM)-Mass Spectrometry (MS) for Quantitative Measurement Of Signaling Pathways"; NIH Public Access Author Manuscript, Methods, Jun. 15, 2013, vol. 61, No. 3, pp. 313-322.
Dubitzky, Werner, et al., Encyclopedia of Systems Biology Copyright 2013,—Excerpt, pp. 1-7, 1914 ("Selected Reaction Monitoring").
European Patent Office Communication pursuant to Article 94(3) EPC issued for EP Application No. 16 725 537.1, dated Aug. 20, 2024 (7 pages).

\* cited by examiner

Fig. 1

```
           10         20         30         40         50         60
MAAQRLGKRV LSKLQSPSRA RGPGGSPGGL QKRHARVTVK YDRRELQRRL DVEKWIDGRL
                                *                   *
           70         80         90        100        110        120
EELYRGMEAD MPDEINIDEL LELESEEERS RKIQGLLKSC GKPVEDFIQE LLAKLQGLHR 130        140
QPG̲LRQPSPS HDGSLSPLQD RARTAHP
                *
```

Fig. 2

```
            10         20         30         40         50         60
    MNRGFSRKSH TFLPKIFFRK MSSSGAKDKP ELQFPFLQDE DTVATLLECK TLFILRGLPG 70         80         90        100        110        120
    SGKSTLARVI VDKYRDGTKM VSADAYKITP GARGAFSEEY KRLDEDLAAY CRRRDIRILV
                                                                    *

130        140        150        160        170        180
    LDDTNHERER LEQLFEMADQ YQYQVVLVEP KTAWRLDCAQ LKEKNQWQLS ADDLKKLKPG 190        200        210        220        230        240
    LEKDFLPLYF GWFLTKKSSE TLRKAG[Q]VFL EELGNHKAFK KELRQFVPGD EPREKMDLVT 250        260        270        280        290        300
    YFGKRPPGVL HCTTKFCDYG KAPGAEEYAQ QDVLKKSYSK AFTLTISALF VTPKTTGARV 310        320        330        340        350        360
    ELSEQQLQLW PSDVDKLSPT DNLPRGSRAH ITLGCAADVE AVQTGLDLLE ILRQEKGGSR 370        380        390        400        410        420
    GEEVGELSRG KLYSLGNGRW MLTLAKNMEV RAIFTGYYGK GKPVPTQGSR KGGALQSCTI
                                                                    *
```

Fig. 3
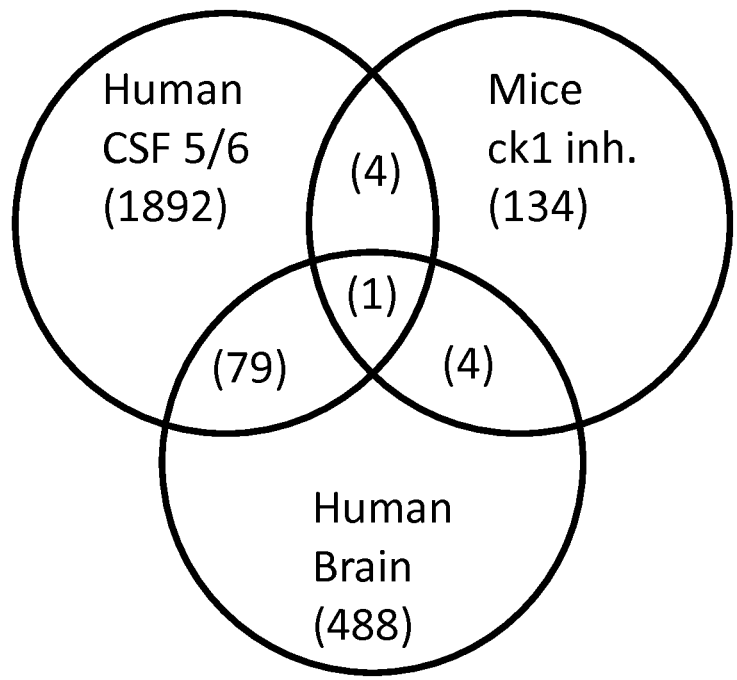
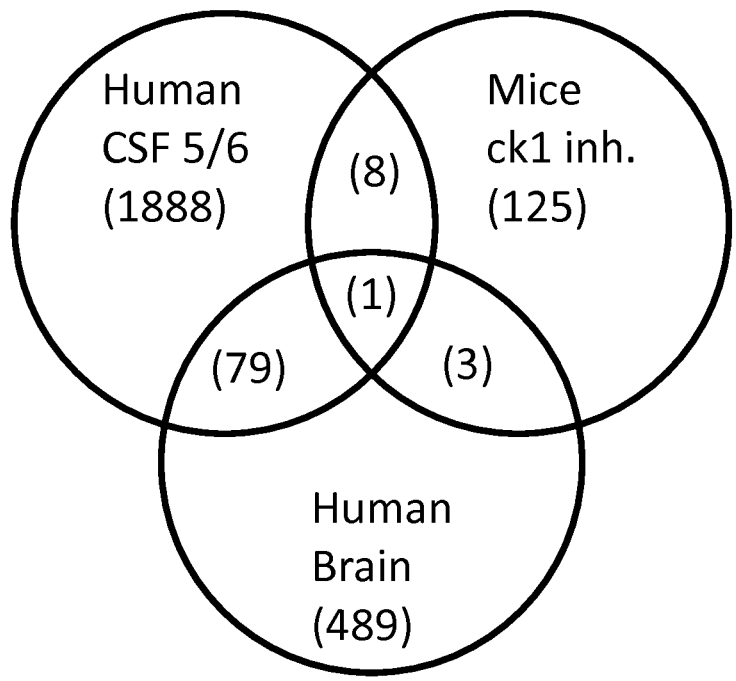

Fig. 4
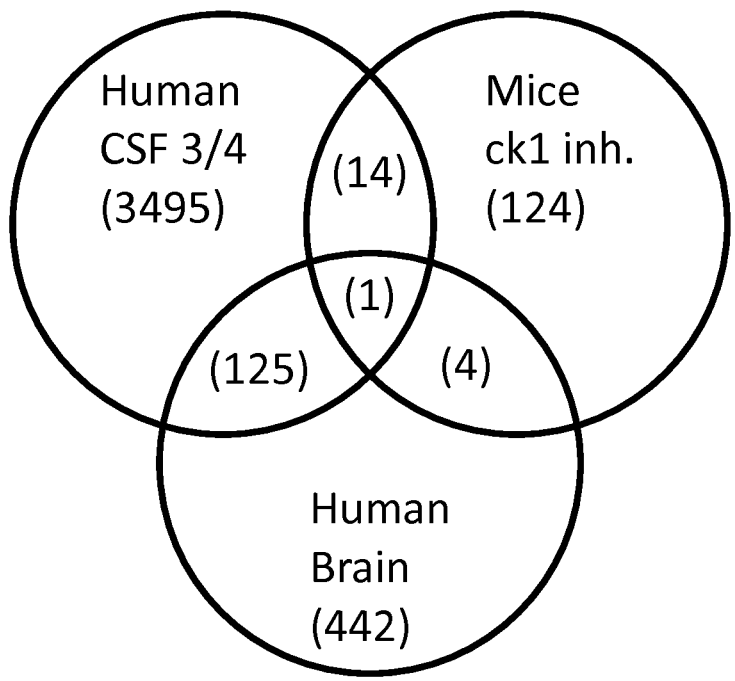
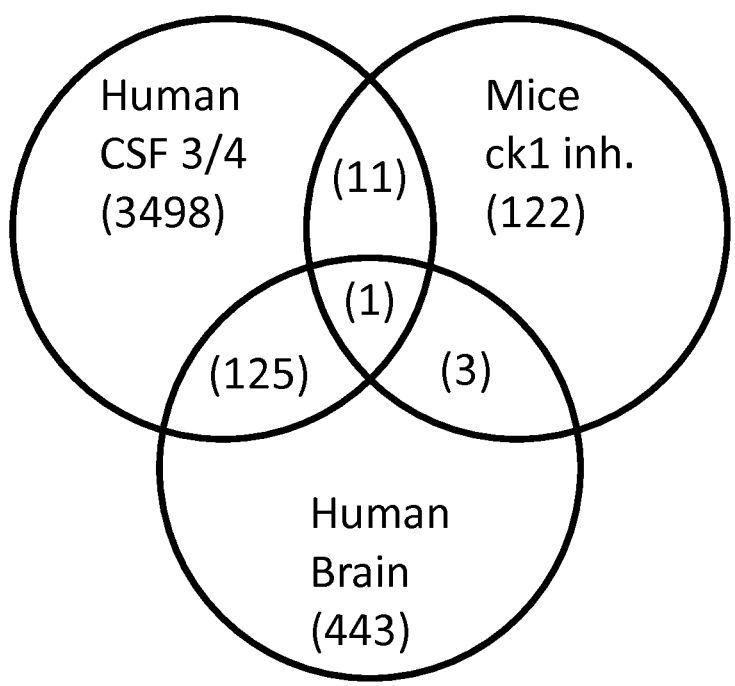

SEQUENCE LISTING

```
<160> NUMBER OF SEQ ID NOS: 31

<210> SEQ ID NO 1
<211> LENGTH: 147
<212> TYPE: PRT
<213> ORGANISM: Homo sapiens

<400> SEQUENCE: 1

Met Ala Ala Gln Arg Leu Gly Lys Arg Val Leu Ser Lys Leu Gln Ser
1               5                   10                  15
```

Pro Ser Arg Ala Arg Gly Pro Gly Ser Pro Gly Gly Leu Gln Lys
            20                  25                  30

Arg His Ala Arg Val Thr Val Lys Tyr Asp Arg Glu Leu Gln Arg
            35                  40                  45

Arg Leu Asp Val Glu Lys Trp Ile Asp Gly Arg Leu Glu Glu Leu Tyr
50                      55                  60

Arg Gly Met Glu Ala Asp Met Pro Asp Glu Ile Asn Ile Asp Glu Leu
65                  70                  75                  80

Leu Glu Leu Glu Ser Glu Glu Arg Ser Arg Lys Ile Gln Gly Leu
                    85                  90                  95

Leu Lys Ser Cys Gly Lys Pro Val Glu Asp Phe Ile Gln Glu Leu Leu
                    100                 105                 110

Ala Lys Leu Gln Gly Leu His Arg Gln Pro Gly Leu Arg Gln Pro Ser
                    115                 120                 125

Pro Ser His Asp Gly Ser Leu Ser Pro Leu Gln Asp Arg Ala Arg Thr
130                     135                 140

Ala His Pro
145

<210> SEQ ID NO 2
<211> LENGTH: 421
<212> TYPE: PRT
<213> ORGANISM: homo sapiens

<400> SEQUENCE: 2

Met Asn Arg Gly Phe Ser Arg Lys Ser His Thr Phe Leu Pro Lys Ile
1               5                   10                  15

Phe Phe Arg Lys Met Ser Ser Ser Gly Ala Lys Asp Lys Pro Glu Leu
                20                  25                  30

Gln Phe Pro Phe Leu Gln Asp Glu Asp Thr Val Ala Thr Leu Leu Glu
            35                  40                  45

Cys Lys Thr Leu Phe Ile Leu Arg Gly Leu Pro Gly Ser Gly Lys Ser
        50                  55                  60

Thr Leu Ala Arg Val Ile Val Asp Lys Tyr Arg Asp Gly Thr Lys Met
65                  70                  75                  80

Val Ser Ala Asp Ala Tyr Lys Ile Thr Pro Gly Ala Arg Gly Ala Phe
                85                  90                  95

Ser Glu Glu Tyr Lys Arg Leu Asp Glu Asp Leu Ala Ala Tyr Cys Arg
                100                 105                 110

Arg Arg Asp Ile Arg Ile Leu Val Leu Asp Asp Thr Asn His Glu Arg
                115                 120                 125

Glu Arg Leu Glu Gln Leu Phe Glu Met Ala Asp Gln Tyr Gln Tyr Gln
            130                 135                 140

Val Val Leu Val Glu Pro Lys Thr Ala Trp Arg Leu Asp Cys Ala Gln
145                 150                 155                 160

Leu Lys Glu Lys Asn Gln Trp Gln Leu Ser Ala Asp Asp Leu Lys Lys
                165                 170                 175

Leu Lys Pro Gly Leu Glu Lys Asp Phe Leu Pro Leu Tyr Phe Gly Trp
                180                 185                 190

Phe Leu Thr Lys Lys Ser Ser Glu Thr Leu Arg Lys Ala Gly Gln Val
            195                 200                 205

Phe Leu Glu Glu Leu Gly Asn His Lys Ala Phe Lys Lys Glu Leu Arg
210                 215                 220

Gln Phe Val Pro Gly Asp Glu Pro Arg Glu Lys Met Asp Leu Val Thr
225                 230                 235                 240

```
Tyr Phe Gly Lys Arg Pro Pro Gly Val Leu His Cys Thr Thr Lys Phe
                245                 250                 255

Cys Asp Tyr Gly Lys Ala Pro Gly Ala Glu Glu Tyr Ala Gln Gln Asp
            260                 265                 270

Val Leu Lys Lys Ser Tyr Ser Lys Ala Phe Thr Leu Thr Ile Ser Ala
        275                 280                 285

Leu Phe Val Thr Pro Lys Thr Thr Gly Ala Arg Val Glu Leu Ser Glu
    290                 295                 300

Gln Gln Leu Gln Leu Trp Pro Ser Asp Val Asp Lys Leu Ser Pro Thr
305                 310                 315                 320

Asp Asn Leu Pro Arg Gly Ser Arg Ala His Ile Thr Leu Gly Cys Ala
                325                 330                 335

Ala Asp Val Glu Ala Val Gln Thr Gly Leu Asp Leu Leu Glu Ile Leu
            340                 345                 350

Arg Gln Glu Lys Gly Gly Ser Arg Gly Glu Glu Val Gly Glu Leu Ser
        355                 360                 365

Arg Gly Lys Leu Tyr Ser Leu Gly Asn Gly Arg Trp Met Leu Thr Leu
    370                 375                 380

Ala Lys Asn Met Glu Val Arg Ala Ile Phe Thr Gly Tyr Tyr Gly Lys
385                 390                 395                 400

Gly Lys Pro Val Pro Thr Gln Gly Ser Arg Lys Gly Gly Ala Leu Gln
                405                 410                 415

Ser Cys Thr Ile Ile
            420

<210> SEQ ID NO 3
<211> LENGTH: 195
<212> TYPE: PRT
<213> ORGANISM: Homo sapiens

<400> SEQUENCE: 3

Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
```

-continued

```
                180                 185                 190

Gly Met Asp
        195

<210> SEQ ID NO 4
<211> LENGTH: 968
<212> TYPE: PRT
<213> ORGANISM: Homo sapiens

<400> SEQUENCE: 4

Met Asp Asp Ser Glu Val Glu Ser Thr Ala Ser Ile Leu Ala Ser Val
1               5                   10                  15

Lys Glu Gln Glu Ala Gln Phe Glu Lys Leu Thr Arg Ala Leu Glu Glu
                20                  25                  30

Glu Arg Arg His Val Ser Ala Gln Leu Glu Arg Val Arg Val Ser Pro
            35                  40                  45

Gln Asp Ala Asn Pro Leu Met Ala Asn Gly Thr Leu Thr Arg Arg His
    50                  55                  60

Gln Asn Gly Arg Phe Val Gly Asp Ala Asp Leu Glu Arg Gln Lys Phe
65                  70                  75                  80

Ser Asp Leu Lys Leu Asn Gly Pro Gln Asp His Ser His Ser Leu Leu Tyr
                85                  90                  95

Ser Thr Ile Pro Arg Met Gln Glu Pro Gly Gln Ile Val Glu Thr Tyr
                100                 105                 110

Thr Glu Glu Asp Pro Glu Gly Ala Met Ser Val Val Ser Val Glu Thr
            115                 120                 125

Ser Asp Asp Gly Thr Thr Arg Arg Thr Glu Thr Thr Val Lys Lys Val
    130                 135                 140

Val Lys Thr Val Thr Thr Arg Thr Val Gln Pro Val Ala Met Gly Pro
145                 150                 155                 160

Asp Gly Leu Pro Val Asp Ala Ser Ser Val Ser Asn Asn Tyr Ile Gln
                165                 170                 175

Thr Leu Gly Arg Asp Phe Arg Lys Asn Gly Asn Gly Gly Pro Gly Pro
                180                 185                 190

Tyr Val Gly Gln Ala Gly Thr Ala Thr Leu Pro Arg Asn Phe His Tyr
            195                 200                 205

Pro Pro Asp Gly Tyr Ser Arg His Tyr Glu Asp Gly Tyr Pro Gly Gly
    210                 215                 220

Ser Asp Asn Tyr Gly Ser Leu Ser Arg Val Thr Arg Ile Glu Glu Arg
225                 230                 235                 240

Tyr Arg Pro Ser Met Glu Gly Tyr Arg Ala Pro Ser Arg Gln Asp Val
                245                 250                 255

Tyr Gly Pro Gln Pro Gln Val Arg Val Gly Gly Ser Ser Val Asp Leu
            260                 265                 270

His Arg Phe His Pro Glu Pro Tyr Gly Leu Glu Asp Asp Gln Arg Ser
        275                 280                 285

Met Gly Tyr Asp Asp Leu Asp Tyr Gly Met Met Ser Asp Tyr Gly Thr
    290                 295                 300

Ala Arg Arg Thr Gly Thr Pro Ser Asp Pro Arg Arg Leu Arg Ser
305                 310                 315                 320

Tyr Glu Asp Met Ile Gly Glu Val Pro Ser Asp Gln Tyr Tyr Trp
                325                 330                 335

Ala Pro Leu Ala Gln His Glu Arg Gly Ser Leu Ala Ser Leu Asp Ser
            340                 345                 350
```

-continued

Leu Arg Lys Gly Gly Pro Pro Pro Asn Trp Arg Gln Pro Glu Leu
            355                 360                 365

Pro Glu Val Ile Ala Met Leu Gly Phe Arg Leu Asp Ala Val Lys Ser
    370                 375                 380

Asn Ala Ala Ala Tyr Leu Gln His Leu Cys Tyr Arg Asn Asp Lys Val
385                 390                 395                 400

Lys Thr Asp Val Arg Lys Leu Lys Gly Ile Pro Val Leu Val Gly Leu
                405                 410                 415

Leu Asp His Pro Lys Lys Glu Val His Leu Gly Ala Cys Gly Ala Leu
            420                 425                 430

Lys Asn Ile Ser Phe Gly Arg Asp Gln Asp Asn Lys Ile Ala Ile Lys
            435                 440                 445

Asn Cys Asp Gly Val Pro Ala Leu Val Arg Leu Leu Arg Lys Ala Arg
450                 455                 460

Asp Met Asp Leu Thr Glu Val Ile Thr Gly Thr Leu Trp Asn Leu Ser
465                 470                 475                 480

Ser His Asp Ser Ile Lys Met Glu Ile Val Asp His Ala Leu His Ala
            485                 490                 495

Leu Thr Asp Glu Val Ile Ile Pro His Ser Gly Trp Glu Arg Glu Pro
            500                 505                 510

Asn Glu Asp Cys Lys Pro Arg His Ile Glu Trp Glu Ser Val Leu Thr
            515                 520                 525

Asn Thr Ala Gly Cys Leu Arg Asn Val Ser Ser Glu Arg Ser Glu Ala
            530                 535                 540

Arg Arg Lys Leu Arg Glu Cys Asp Gly Leu Val Asp Ala Leu Ile Phe
545                 550                 555                 560

Ile Val Gln Ala Glu Ile Gly Gln Lys Asp Ser Asp Ser Lys Leu Val
                565                 570                 575

Glu Asn Cys Val Cys Leu Leu Arg Asn Leu Ser Tyr Gln Val His Arg
            580                 585                 590

Glu Ile Pro Gln Ala Glu Arg Tyr Gln Glu Ala Ala Pro Asn Val Ala
            595                 600                 605

Asn Asn Thr Gly Pro His Ala Ala Ser Cys Phe Gly Ala Lys Lys Gly
610                 615                 620

Lys Asp Glu Trp Phe Ser Arg Gly Lys Lys Pro Ile Glu Asp Pro Ala
625                 630                 635                 640

Asn Asp Thr Val Asp Phe Pro Lys Arg Thr Ser Pro Ala Arg Gly Tyr
                645                 650                 655

Glu Leu Leu Phe Gln Pro Glu Val Val Arg Ile Tyr Ile Ser Leu Leu
            660                 665                 670

Lys Glu Ser Lys Thr Pro Ala Ile Leu Glu Ala Ser Ala Gly Ala Ile
            675                 680                 685

Gln Asn Leu Cys Ala Gly Arg Trp Thr Tyr Gly Arg Tyr Ile Arg Ser
            690                 695                 700

Ala Leu Arg Gln Glu Lys Ala Leu Ser Ala Ile Ala Asp Leu Leu Thr
705                 710                 715                 720

Asn Glu His Glu Arg Val Val Lys Ala Ala Ser Gly Ala Leu Arg Asn
                725                 730                 735

Leu Ala Val Asp Ala Arg Asn Lys Glu Leu Ile Gly Lys His Ala Ile
            740                 745                 750

Pro Asn Leu Val Lys Asn Leu Pro Gly Gly Gln Gln Asn Ser Ser Trp
            755                 760                 765

Asn Phe Ser Glu Asp Thr Val Ile Ser Ile Leu Asn Thr Ile Asn Glu

```
                    770             775             780
        Val Ile Ala Glu Asn Leu Glu Ala Ala Lys Lys Leu Arg Glu Thr Gln
        785             790             795             800

Gly Ile Glu Lys Leu Val Leu Ile Asn Lys Ser Gly Asn Arg Ser Glu
                        805             810             815

Lys Glu Val Arg Ala Ala Ala Leu Val Leu Gln Thr Ile Trp Gly Tyr
                        820             825             830

Lys Glu Leu Arg Lys Pro Leu Glu Lys Glu Gly Trp Lys Lys Ser Asp
                        835             840             845

Phe Gln Val Asn Leu Asn Asn Ala Ser Arg Ser Gln Ser Ser His Ser
        850             855             860

Tyr Asp Asp Ser Thr Leu Pro Leu Ile Asp Arg Asn Gln Lys Ser Asp
        865             870             875             880

Lys Lys Pro Asp Arg Glu Glu Ile Gln Met Ser Asn Met Gly Ser Asn
                        885             890             895

Thr Lys Ser Leu Asp Asn Asn Tyr Ser Thr Pro Asn Glu Arg Gly Asp
                        900             905             910

His Asn Arg Thr Leu Asp Arg Ser Gly Asp Leu Gly Asp Met Glu Pro
                        915             920             925

Leu Lys Gly Thr Thr Pro Leu Met Gln Asp Glu Gly Gln Glu Ser Leu
        930             935             940

Glu Glu Glu Leu Asp Val Leu Val Leu Asp Asp Glu Gly Gly Gln Val
        945             950             955             960

Ser Tyr Pro Ser Met Gln Lys Ile
                        965

<210> SEQ ID NO 5
<211> LENGTH: 229
<212> TYPE: PRT
<213> ORGANISM: Homo sapiens

<400> SEQUENCE: 5

Met Ala Asp Asp Phe Gly Phe Phe Ser Ser Glu Ser Gly Ala Pro
1               5                   10                  15

Glu Ala Glu Glu Asp Pro Ala Ala Phe Leu Ala Gln Gln Glu
                20                  25              30

Ser Glu Ile Ala Gly Ile Glu Asn Asp Glu Gly Phe Gly Ala Pro Ala
                35                  40                  45

Gly Ser His Ala Ala Pro Ala Gln Pro Gly Pro Thr Ser Gly Ala Gly
        50                  55                  60

Ser Glu Asp Met Gly Thr Thr Val Asn Gly Asp Val Phe Gln Glu Ala
65                  70                  75                  80

Asn Gly Pro Ala Asp Gly Tyr Ala Ala Ile Ala Gln Ala Asp Arg Leu
                85                  90                  95

Thr Gln Glu Pro Glu Ser Ile Arg Lys Trp Arg Glu Glu Gln Arg Lys
                100                 105                 110

Arg Leu Gln Glu Leu Asp Ala Ala Ser Lys Val Thr Glu Gln Glu Trp
                115                 120                 125

Arg Glu Lys Ala Lys Lys Asp Leu Glu Glu Trp Asn Gln Arg Gln Ser
        130                 135                 140

Glu Gln Val Glu Lys Asn Lys Ile Asn Asn Arg Ile Ala Asp Lys Ala
145                 150                 155                 160

Phe Tyr Gln Gln Pro Asp Ala Asp Ile Ile Gly Tyr Val Ala Ser Glu
                165                 170                 175
```

```
Glu Ala Phe Val Lys Glu Ser Lys Glu Thr Pro Gly Thr Glu Trp
            180                 185                 190

Glu Lys Val Ala Gln Leu Cys Asp Phe Asn Pro Lys Ser Ser Lys Gln
195                 200                 205

Cys Lys Asp Val Ser Arg Leu Arg Ser Val Leu Met Ser Leu Lys Gln
210                 215                 220

Thr Pro Leu Ser Arg
225

<210> SEQ ID NO 6
<211> LENGTH: 359
<212> TYPE: PRT
<213> ORGANISM: Homo sapiens

<400> SEQUENCE: 6

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320
```

```
Asp Lys Ile Ile Tyr Ser His Phe Thr Cys Ala Asp Thr Glu Asn
            325                 330                 335

Ile Arg Phe Val Phe Ala Ala Val Lys Asp Thr Ile Leu Gln Leu Asn
            340                 345                 350

Leu Lys Glu Tyr Asn Leu Val
            355

<210> SEQ ID NO 7
<211> LENGTH: 944
<212> TYPE: PRT
<213> ORGANISM: Homo sapiens

<400> SEQUENCE: 7

Met Ala Val Ala Ala Val Ala Ala Arg Arg Arg Ser Trp Ala
1               5                   10                  15

Ser Leu Val Leu Ala Phe Leu Gly Val Cys Leu Gly Ile Thr Leu Ala
                20                  25                  30

Val Asp Arg Ser Asn Phe Lys Thr Cys Glu Glu Ser Ser Phe Cys Lys
            35                  40                  45

Arg Gln Arg Ser Ile Arg Pro Gly Leu Ser Pro Tyr Arg Ala Leu Leu
        50                  55                  60

Asp Ser Leu Gln Leu Gly Pro Asp Ser Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Phe Arg Ile Asp Glu Leu Glu Pro Arg Arg Pro Arg
            100                 105                 110

Tyr Arg Val Pro Asp Val Leu Val Ala Asp Pro Pro Ile Ala Arg Leu
        115                 120                 125

Ser Val Ser Gly Arg Asp Glu Asn Ser Val Glu Leu Thr Met Ala Glu
    130                 135                 140

Gly Pro Tyr Lys Ile Ile Leu Thr Ala Arg Pro Phe Arg Leu Asp Leu
145                 150                 155                 160

Leu Glu Asp Arg Ser Leu Leu Leu Ser Val Asn Ala Arg Gly Leu Leu
                165                 170                 175

Glu Phe Glu His Gln Arg Ala Pro Arg Val Ser Gln Gly Ser Lys Asp
            180                 185                 190

Pro Ala Glu Gly Asp Gly Ala Gln Pro Glu Glu Thr Pro Arg Asp Gly
        195                 200                 205

Asp Lys Pro Glu Glu Thr Gln Gly Lys Ala Glu Lys Asp Glu Pro Gly
    210                 215                 220

Ala Trp Glu Glu Thr Phe Lys Thr His Ser Asp Ser Lys Pro Tyr Gly
225                 230                 235                 240

Pro Met Ser Val Gly Leu Asp Phe Ser Leu Pro Gly Met Glu His Val
                245                 250                 255

Tyr Gly Ile Pro Glu His Ala Asp Asn Leu Arg Leu Lys Val Thr Glu
            260                 265                 270

Gly Gly Glu Pro Tyr Arg Leu Tyr Asn Leu Asp Val Phe Gln Tyr Glu
        275                 280                 285

Leu Tyr Asn Pro Met Ala Leu Tyr Gly Ser Val Pro Val Leu Leu Ala
    290                 295                 300

His Asn Pro His Arg Asp Leu Gly Ile Phe Trp Leu Asn Ala Ala Glu
305                 310                 315                 320

Thr Trp Val Asp Ile Ser Ser Asn Thr Ala Gly Lys Thr Leu Phe Gly
```

```
            325                 330                 335
Lys Met Met Asp Tyr Leu Gln Gly Ser Gly Glu Thr Pro Gln Thr Asp
            340                 345                 350

Val Arg Trp Met Ser Glu Thr Gly Ile Ile Asp Val Phe Leu Leu Leu
            355                 360                 365

Gly Pro Ser Ile Ser Asp Val Phe Arg Gln Tyr Ala Ser Leu Thr Gly
            370                 375                 380

Thr Gln Ala Leu Pro Pro Leu Phe Ser Leu Gly Tyr His Gln Ser Arg
385                 390                 395                 400

Trp Asn Tyr Arg Asp Glu Ala Asp Val Leu Glu Val Asp Gln Gly Phe
                    405                 410                 415

Asp Asp His Asn Leu Pro Cys Asp Val Ile Trp Leu Asp Ile Glu His
                    420                 425                 430

Ala Asp Gly Lys Arg Tyr Phe Thr Trp Asp Pro Ser Arg Phe Pro Gln
                    435                 440                 445

Pro Arg Thr Met Leu Glu Arg Leu Ala Ser Lys Arg Lys Leu Val
                    450                 455                 460

Ala Ile Val Asp Pro His Ile Lys Val Asp Ser Gly Tyr Arg Val His
465                 470                 475                 480

Glu Glu Leu Arg Asn Leu Gly Leu Tyr Val Lys Thr Arg Asp Gly Ser
                    485                 490                 495

Asp Tyr Glu Gly Trp Cys Trp Pro Gly Ser Ala Gly Tyr Pro Asp Phe
                    500                 505                 510

Thr Asn Pro Thr Met Arg Ala Trp Trp Ala Asn Met Phe Ser Tyr Asp
                    515                 520                 525

Asn Tyr Glu Gly Ser Ala Pro Asn Leu Phe Val Trp Asn Asp Met Asn
                    530                 535                 540

Glu Pro Ser Val Phe Asn Gly Pro Glu Val Thr Met Leu Lys Asp Ala
545                 550                 555                 560

Gln His Tyr Gly Gly Trp Glu His Arg Asp Val His Asn Ile Tyr Gly
                    565                 570                 575

Leu Tyr Val His Met Ala Thr Ala Asp Gly Leu Arg Gln Arg Ser Gly
                    580                 585                 590

Gly Met Glu Arg Pro Phe Val Leu Ala Arg Ala Phe Phe Ala Gly Ser
                    595                 600                 605

Gln Arg Phe Gly Ala Val Trp Thr Gly Asp Asn Thr Ala Glu Trp Asp
                    610                 615                 620

His Leu Lys Ile Ser Ile Pro Met Cys Leu Ser Leu Gly Leu Val Gly
625                 630                 635                 640

Leu Ser Phe Cys Gly Ala Asp Val Gly Gly Phe Phe Lys Asn Pro Glu
                    645                 650                 655

Pro Glu Leu Leu Val Arg Trp Tyr Gln Met Gly Ala Tyr Gln Pro Phe
                    660                 665                 670

Phe Arg Ala His Ala His Leu Asp Thr Gly Arg Arg Glu Pro Trp Leu
                    675                 680                 685

Leu Pro Ser Gln His Asn Asp Ile Ile Arg Asp Ala Leu Gly Gln Arg
                    690                 695                 700

Tyr Ser Leu Leu Pro Phe Trp Tyr Thr Leu Leu Tyr Gln Ala His Arg
705                 710                 715                 720

Glu Gly Ile Pro Val Met Arg Pro Leu Trp Val Gln Tyr Pro Gln Asp
                    725                 730                 735

Val Thr Thr Phe Asn Ile Asp Asp Gln Tyr Leu Leu Gly Asp Ala Leu
                    740                 745                 750
```

-continued

Leu Val His Pro Val Ser Asp Ser Gly Ala His Gly Val Gln Val Tyr
            755                 760                 765

Leu Pro Gly Gln Gly Glu Val Trp Tyr Asp Ile Gln Ser Tyr Gln Lys
        770                 775                 780

His His Gly Pro Gln Thr Leu Tyr Leu Pro Val Thr Leu Ser Ser Ile
785                 790                 795                 800

Pro Val Phe Gln Arg Gly Gly Thr Ile Val Pro Arg Trp Met Arg Val
            805                 810                 815

Arg Arg Ser Ser Glu Cys Met Lys Asp Asp Pro Ile Thr Leu Phe Val
            820                 825                 830

Ala Leu Ser Pro Gln Gly Thr Ala Gln Gly Glu Leu Phe Leu Asp Asp
            835                 840                 845

Gly His Thr Phe Asn Tyr Gln Thr Arg Gln Glu Phe Leu Leu Arg Arg
850                 855                 860

Phe Ser Phe Ser Gly Asn Thr Leu Val Ser Ser Ala Asp Pro Glu
865                 870                 875                 880

Gly His Phe Glu Thr Pro Ile Trp Ile Glu Arg Val Val Ile Gly
            885                 890                 895

Ala Gly Lys Pro Ala Ala Val Val Leu Gln Thr Lys Gly Ser Pro Glu
            900                 905                 910

Ser Arg Leu Ser Phe Gln His Asp Pro Glu Thr Ser Val Leu Val Leu
            915                 920                 925

Arg Lys Pro Gly Ile Asn Val Ala Ser Asp Trp Ser Ile His Leu Arg
            930                 935                 940

<210> SEQ ID NO 8
<211> LENGTH: 425
<212> TYPE: PRT
<213> ORGANISM: Homo sapiens

<400> SEQUENCE: 8

Met Ala Ser Ser Ser Pro Asp Ser Pro Cys Ser Cys Asp Cys Phe Val
1               5                   10                  15

Ser Val Pro Pro Ala Ser Ala Ile Pro Ala Val Ile Phe Ala Lys Asn
                20                  25                  30

Ser Asp Arg Pro Arg Asp Glu Val Gln Glu Val Val Phe Val Pro Ala
            35                  40                  45

Gly Thr His Thr Pro Gly Ser Arg Leu Gln Cys Thr Tyr Ile Glu Val
        50                  55                  60

Glu Gln Val Ser Lys Thr His Ala Val Ile Leu Ser Arg Pro Ser Trp
65                  70                  75                  80

Leu Trp Gly Ala Glu Met Gly Ala Asn Glu His Gly Val Cys Ile Gly
                85                  90                  95

Asn Glu Ala Val Trp Thr Lys Glu Pro Val Gly Glu Gly Glu Ala Leu
            100                 105                 110

Leu Gly Met Asp Leu Leu Arg Leu Ala Leu Glu Arg Ser Ser Ser Ala
        115                 120                 125

Gln Glu Ala Leu His Val Ile Thr Gly Leu Leu Glu His Tyr Gly Gln
    130                 135                 140

Gly Gly Asn Cys Leu Glu Asp Ala Ala Pro Phe Ser Tyr His Ser Thr
145                 150                 155                 160

Phe Leu Leu Ala Asp Arg Thr Glu Ala Trp Val Leu Glu Thr Ala Gly
                165                 170                 175

Arg Leu Trp Ala Ala Gln Arg Ile Gln Glu Gly Ala Arg Asn Ile Ser

```
                 180                 185                 190
Asn Gln Leu Ser Ile Gly Thr Asp Ile Ser Ala Gln His Pro Glu Leu
            195                 200                 205

Arg Thr His Ala Gln Ala Lys Gly Trp Trp Asp Gly Gln Gly Ala Phe
        210                 215                 220

Asp Phe Ala Gln Ile Phe Ser Leu Thr Gln Gln Pro Val Arg Met Glu
225                 230                 235                 240

Ala Ala Lys Ala Arg Phe Gln Ala Gly Arg Glu Leu Leu Arg Gln Arg
                245                 250                 255

Gln Gly Gly Ile Thr Ala Glu Val Met Met Gly Ile Leu Arg Asp Lys
            260                 265                 270

Glu Ser Gly Ile Cys Met Asp Ser Gly Gly Phe Arg Thr Thr Ala Ser
        275                 280                 285

Met Val Ser Val Leu Pro Gln Asp Pro Thr Gln Pro Cys Val His Phe
    290                 295                 300

Leu Thr Ala Thr Pro Asp Pro Ser Arg Ser Val Phe Lys Pro Phe Ile
305                 310                 315                 320

Phe Gly Met Gly Val Ala Gln Ala Pro Gln Val Leu Ser Pro Thr Phe
                325                 330                 335

Gly Ala Gln Asp Pro Val Arg Thr Leu Pro Arg Phe Gln Thr Gln Val
            340                 345                 350

Asp Arg Arg His Thr Leu Tyr Arg Gly His Gln Ala Ala Leu Gly Leu
        355                 360                 365

Met Glu Arg Asp Gln Asp Arg Gly Gln Gln Leu Gln Gln Lys Gln Gln
    370                 375                 380

Asp Leu Glu Gln Glu Gly Leu Glu Ala Thr Gln Gly Leu Leu Ala Gly
385                 390                 395                 400

Glu Trp Ala Pro Pro Leu Trp Glu Leu Gly Ser Leu Phe Gln Ala Phe
                405                 410                 415

Val Lys Arg Glu Ser Gln Ala Tyr Ala
            420                 425

<210> SEQ ID NO 9
<211> LENGTH: 412
<212> TYPE: PRT
<213> ORGANISM: Homo sapiens

<400> SEQUENCE: 9

Met Ala Ala Ala Leu Leu Ala Arg Ala Ser Gly Pro Ala Arg Arg Ala
1               5                   10                  15

Leu Cys Pro Arg Ala Trp Arg Gln Leu His Thr Ile Tyr Gln Ser Val
            20                  25                  30

Glu Leu Pro Glu Thr His Gln Met Leu Leu Gln Thr Cys Arg Asp Phe
        35                  40                  45

Ala Glu Lys Glu Leu Phe Pro Ile Ala Ala Gln Val Asp Lys Glu His
    50                  55                  60

Leu Phe Pro Ala Ala Gln Val Lys Lys Met Gly Gly Leu Gly Leu Leu
65                  70                  75                  80

Ala Met Asp Val Pro Glu Glu Leu Gly Gly Ala Gly Leu Asp Tyr Leu
                85                  90                  95

Ala Tyr Ala Ile Ala Met Glu Glu Ile Ser Arg Gly Cys Ala Ser Thr
            100                 105                 110

Gly Val Ile Met Ser Val Asn Asn Ser Leu Tyr Leu Gly Pro Ile Leu
        115                 120                 125
```

```
Lys Phe Gly Ser Lys Glu Gln Lys Gln Ala Trp Val Thr Pro Phe Thr
    130                 135                 140

Ser Gly Asp Lys Ile Gly Cys Phe Ala Leu Ser Glu Pro Gly Asn Gly
145                 150                 155                 160

Ser Asp Ala Gly Ala Ala Ser Thr Thr Ala Arg Ala Glu Gly Asp Ser
                165                 170                 175

Trp Val Leu Asn Gly Thr Lys Ala Trp Ile Thr Asn Ala Trp Glu Ala
                180                 185                 190

Ser Ala Ala Val Val Phe Ala Ser Thr Asp Arg Ala Leu Gln Asn Lys
            195                 200                 205

Gly Ile Ser Ala Phe Leu Val Pro Met Pro Thr Pro Gly Leu Thr Leu
210                 215                 220

Gly Lys Lys Glu Asp Lys Leu Gly Ile Arg Gly Ser Ser Thr Ala Asn
225                 230                 235                 240

Leu Ile Phe Glu Asp Cys Arg Ile Pro Lys Asp Ser Ile Leu Gly Glu
                245                 250                 255

Pro Gly Met Gly Phe Lys Ile Ala Met Gln Thr Leu Asp Met Gly Arg
                260                 265                 270

Ile Gly Ile Ala Ser Gln Ala Leu Gly Ile Ala Gln Thr Ala Leu Asp
            275                 280                 285

Cys Ala Val Asn Tyr Ala Glu Asn Arg Met Ala Phe Gly Ala Pro Leu
290                 295                 300

Thr Lys Leu Gln Val Ile Gln Phe Lys Leu Ala Asp Met Ala Leu Ala
305                 310                 315                 320

Leu Glu Ser Ala Arg Leu Leu Thr Trp Arg Ala Ala Met Leu Lys Asp
                325                 330                 335

Asn Lys Lys Pro Phe Ile Lys Glu Ala Ala Met Ala Lys Leu Ala Ala
                340                 345                 350

Ser Glu Ala Ala Thr Ala Ile Ser His Gln Ala Ile Gln Ile Leu Gly
            355                 360                 365

Gly Met Gly Tyr Val Thr Glu Met Pro Ala Glu Arg His Tyr Arg Asp
370                 375                 380

Ala Arg Ile Thr Glu Ile Tyr Glu Gly Thr Ser Glu Ile Gln Arg Leu
385                 390                 395                 400

Val Ile Ala Gly His Leu Leu Arg Ser Tyr Arg Ser
                405                 410

<210> SEQ ID NO 10
<211> LENGTH: 494
<212> TYPE: PRT
<213> ORGANISM: Homo sapiens

<400> SEQUENCE: 10

Met Ala Met Ser Leu Pro Gly Ser Arg Arg Thr Ser Ala Gly Ser Arg
1               5                   10                  15

Arg Arg Thr Ser Pro Pro Val Ser Val Arg Asp Ala Tyr Gly Thr Ser
                20                  25                  30

Ser Leu Ser Ser Ser Ser Asn Ser Gly Ser Tyr Lys Gly Ser Asp Ser
            35                  40                  45

Ser Pro Thr Pro Arg Arg Ser Met Lys Tyr Thr Leu Cys Ser Asp Asn
        50                  55                  60

His Gly Ile Lys Pro Pro Thr Pro Glu Gln Tyr Leu Thr Pro Leu Gln
65                  70                  75                  80

Gln Lys Glu Val Cys Ile Arg His Leu Lys Ala Arg Leu Lys Asp Thr
                85                  90                  95
```

Gln Asp Arg Leu Gln Asp Arg Asp Thr Glu Ile Asp Asp Leu Lys Thr
            100                 105                 110

Gln Leu Ser Arg Met Gln Glu Asp Trp Ile Glu Glu Cys His Arg
        115                 120                 125

Val Glu Ala Gln Leu Ala Leu Lys Glu Ala Arg Lys Glu Ile Lys Gln
130                 135                 140

Leu Lys Gln Val Ile Asp Thr Val Lys Asn Asn Leu Ile Asp Lys Asp
145                 150                 155                 160

Lys Gly Leu Gln Lys Tyr Phe Val Asp Ile Asn Ile Gln Asn Lys Lys
                165                 170                 175

Leu Glu Thr Leu Leu His Ser Met Glu Val Ala Gln Asn Gly Met Ala
            180                 185                 190

Lys Glu Asp Gly Thr Gly Glu Ser Ala Gly Gly Ser Pro Ala Arg Ser
        195                 200                 205

Leu Thr Arg Ser Ser Thr Tyr Thr Lys Leu Ser Asp Pro Ala Val Cys
    210                 215                 220

Gly Asp Arg Gln Pro Gly Asp Pro Ser Ser Gly Ser Ala Glu Asp Gly
225                 230                 235                 240

Ala Asp Ser Gly Phe Ala Ala Asp Asp Thr Leu Ser Arg Thr Asp
                245                 250                 255

Ala Leu Glu Ala Ser Ser Leu Leu Ser Ser Gly Val Asp Cys Gly Thr
            260                 265                 270

Glu Glu Thr Ser Leu His Ser Ser Phe Gly Leu Gly Pro Arg Phe Pro
        275                 280                 285

Ala Ser Asn Thr Tyr Glu Lys Leu Leu Cys Gly Met Glu Ala Gly Val
    290                 295                 300

Gln Ala Ser Cys Met Gln Glu Arg Ala Ile Gln Thr Asp Phe Val Gln
305                 310                 315                 320

Tyr Gln Pro Asp Leu Asp Thr Ile Leu Glu Lys Val Thr Gln Ala Gln
                325                 330                 335

Val Cys Gly Thr Asp Pro Glu Ser Gly Asp Arg Cys Pro Glu Leu Asp
            340                 345                 350

Ala His Pro Ser Gly Pro Arg Asp Pro Asn Ser Ala Val Val Thr
        355                 360                 365

Val Gly Asp Glu Leu Glu Ala Pro Glu Pro Ile Thr Arg Gly Pro Thr
    370                 375                 380

Pro Gln Arg Pro Gly Ala Asn Pro Asn Pro Gly Gln Ser Val Ser Val
385                 390                 395                 400

Val Cys Pro Met Glu Glu Glu Glu Ala Val Ala Glu Lys Glu
                405                 410                 415

Pro Lys Ser Tyr Trp Ser Arg His Tyr Ile Val Asp Leu Leu Ala Val
            420                 425                 430

Val Val Pro Ala Val Pro Thr Val Ala Trp Leu Cys Arg Ser Gln Arg
        435                 440                 445

Arg Gln Gly Gln Pro Ile Tyr Asn Ile Ser Ser Leu Leu Arg Gly Cys
    450                 455                 460

Cys Thr Val Ala Leu His Ser Ile Arg Arg Ile Ser Cys Arg Ser Leu
465                 470                 475                 480

Ser Gln Pro Ser Pro Ser Pro Ala Gly Gly Gly Ser Gln Leu
                485                 490

<210> SEQ ID NO 11
<211> LENGTH: 377

<212> TYPE: PRT
<213> ORGANISM: Homo sapiens

<400> SEQUENCE: 11

```
Met Cys Asp Asp Glu Thr Thr Ala Leu Val Cys Asp Asn Gly Ser
1               5                   10                  15

Gly Leu Val Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Thr Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
210                 215                 220

Phe Glu Asn Glu Met Ala Thr Ala Ala Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
        275                 280                 285

Ile Asp Ile Arg Lys Asp Leu Tyr Ala Asn Asn Val Leu Ser Gly Gly
290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Ser Lys Gln Glu Tyr Asp Glu Ala Gly
        355                 360                 365

Pro Ser Ile Val His Arg Lys Cys Phe
370                 375
```

<210> SEQ ID NO 12

```
<211> LENGTH: 464
<212> TYPE: PRT
<213> ORGANISM: Homo sapiens

<400> SEQUENCE: 12

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65              70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
```

```
385                 390                 395                 400
His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
                420                 425                 430

Thr Phe Lys Ala Asn Arg Pro Phe Leu Val Phe Ile Arg Glu Val Pro
                435                 440                 445

Leu Asn Thr Ile Ile Phe Met Gly Arg Val Ala Asn Pro Cys Val Lys
    450                 455                 460

<210> SEQ ID NO 13
<211> LENGTH: 426
<212> TYPE: PRT
<213> ORGANISM: Homo sapiens

<400> SEQUENCE: 13

Met Ala Asn Asp Ser Gly Gly Pro Gly Gly Pro Ser Pro Ser Glu Arg
1               5                   10                  15

Asp Arg Gln Tyr Cys Glu Leu Cys Gly Lys Met Glu Asn Leu Leu Arg
                20                  25                  30

Cys Ser Arg Cys Arg Ser Ser Phe Tyr Cys Cys Lys Glu His Gln Arg
            35                  40                  45

Gln Asp Trp Lys Lys His Lys Leu Val Cys Gln Gly Ser Glu Gly Ala
    50                  55                  60

Leu Gly His Gly Val Gly Pro His Gln His Ser Gly Pro Ala Pro Pro
65              70                  75                  80

Ala Ala Val Pro Pro Arg Ala Gly Ala Arg Glu Pro Arg Lys Ala
                85                  90                  95

Ala Ala Arg Arg Asp Asn Ala Ser Gly Asp Ala Ala Lys Gly Lys Val
                100                 105                 110

Lys Ala Lys Pro Pro Ala Asp Pro Ala Ala Ala Ser Pro Cys Arg
                115                 120                 125

Ala Ala Ala Gly Gly Gln Gly Ser Ala Val Ala Ala Glu Ala Glu Pro
    130                 135                 140

Gly Lys Glu Glu Pro Pro Ala Arg Ser Ser Leu Phe Gln Glu Lys Ala
145                 150                 155                 160

Asn Leu Tyr Pro Pro Ser Asn Thr Pro Gly Asp Ala Leu Ser Pro Gly
                165                 170                 175

Gly Gly Leu Arg Pro Asn Gly Gln Thr Lys Pro Leu Pro Ala Leu Lys
                180                 185                 190

Leu Ala Leu Glu Tyr Ile Val Pro Cys Met Asn Lys His Gly Ile Cys
    195                 200                 205

Val Val Asp Asp Phe Leu Gly Lys Glu Thr Gly Gln Gln Ile Gly Asp
    210                 215                 220

Glu Val Arg Ala Leu His Asp Thr Gly Lys Phe Thr Asp Gly Gln Leu
225                 230                 235                 240

Val Ser Gln Lys Ser Asp Ser Ser Lys Asp Ile Arg Gly Asp Lys Ile
                245                 250                 255

Thr Trp Ile Glu Gly Lys Glu Pro Gly Cys Glu Thr Ile Gly Leu Leu
                260                 265                 270

Met Ser Ser Met Asp Asp Leu Ile Arg His Cys Asn Gly Lys Leu Gly
            275                 280                 285

Ser Tyr Lys Ile Asn Gly Arg Thr Lys Ala Met Val Ala Cys Tyr Pro
    290                 295                 300
```

```
Gly Asn Gly Thr Gly Tyr Val Arg His Val Asp Asn Pro Asn Gly Asp
305                 310                 315                 320

Gly Arg Cys Val Thr Cys Ile Tyr Tyr Leu Asn Lys Asp Trp Asp Ala
            325                 330                 335

Lys Val Ser Gly Gly Ile Leu Arg Ile Phe Pro Glu Gly Lys Ala Gln
            340                 345                 350

Phe Ala Asp Ile Glu Pro Lys Phe Asp Arg Leu Leu Phe Phe Trp Ser
            355                 360                 365

Asp Arg Arg Asn Pro His Glu Val Gln Pro Ala Tyr Ala Thr Arg Tyr
            370                 375                 380

Ala Ile Thr Val Trp Tyr Phe Asp Ala Asp Glu Arg Ala Arg Ala Lys
385                 390                 395                 400

Val Lys Tyr Leu Thr Gly Glu Lys Gly Val Arg Val Glu Leu Asn Lys
                405                 410                 415

Pro Ser Asp Ser Val Gly Lys Asp Val Phe
            420                 425

<210> SEQ ID NO 14
<211> LENGTH: 453
<212> TYPE: PRT
<213> ORGANISM: Homo sapiens

<400> SEQUENCE: 14

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255
```

```
Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
            275                 280                 285

Ala Met Phe Lys Val Gly Pro Glu Ala Asp Lys Tyr Arg Leu Thr Tyr
            290                 295                 300

Ala Tyr Phe Ala Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Lys Phe Glu Gly Asn Cys
            340                 345                 350

Ala Glu Gln Asp Gly Ser Gly Trp Trp Met Asn Lys Cys His Ala Gly
            355                 360                 365

His Leu Asn Gly Val Tyr Tyr Gln Gly Gly Thr Tyr Ser Lys Ala Ser
            370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His His Leu Gly Gly Ala Lys
            420                 425                 430

Gln Val Arg Pro Glu His Pro Ala Glu Thr Glu Tyr Asp Ser Leu Tyr
            435                 440                 445

Pro Glu Asp Asp Leu
        450

<210> SEQ ID NO 15
<211> LENGTH: 240
<212> TYPE: PRT
<213> ORGANISM: Homo sapiens

<400> SEQUENCE: 15

Met Thr Pro His Arg Leu Leu Pro Pro Leu Leu Leu Leu Leu Ala Leu
1               5                   10                  15

Leu Leu Ala Ala Ser Pro Gly Gly Ala Leu Ala Arg Cys Pro Gly Cys
            20                  25                  30

Gly Gln Gly Val Gln Ala Gly Cys Pro Gly Gly Cys Val Glu Glu Glu
            35                  40                  45

Asp Gly Gly Ser Pro Ala Glu Gly Cys Ala Glu Ala Glu Gly Cys Leu
50                  55                  60

Arg Arg Glu Gly Gln Glu Cys Gly Val Tyr Thr Pro Asn Cys Ala Pro
65                  70                  75                  80

Gly Leu Gln Cys His Pro Pro Lys Asp Asp Glu Ala Pro Leu Arg Ala
            85                  90                  95

Leu Leu Leu Gly Arg Gly Arg Cys Leu Pro Ala Arg Ala Pro Ala Val
            100                 105                 110

Ala Glu Glu Asn Pro Lys Glu Ser Lys Pro Gln Ala Gly Thr Ala Arg
            115                 120                 125

Pro Gln Asp Val Asn Arg Arg Asp Gln Gln Arg Asn Pro Gly Thr Ser
            130                 135                 140

Thr Thr Pro Ser Gln Pro Asn Ser Ala Gly Val Gln Asp Thr Glu Met
145                 150                 155                 160

Gly Pro Cys Arg Arg His Leu Asp Ser Val Leu Gln Gln Leu Gln Thr
```

```
                165                 170                 175
Glu Val Tyr Arg Gly Ala Gln Thr Leu Tyr Val Pro Asn Cys Asp His
            180                 185                 190

Arg Gly Phe Tyr Arg Lys Arg Gln Cys Arg Ser Ser Gln Gly Gln Arg
        195                 200                 205

Arg Gly Pro Cys Trp Cys Val Asp Arg Met Gly Lys Ser Leu Pro Gly
    210                 215                 220

Ser Pro Asp Gly Asn Gly Ser Ser Ser Cys Pro Thr Gly Ser Ser Gly
225                 230                 235                 240

<210> SEQ ID NO 16
<211> LENGTH: 245
<212> TYPE: PRT
<213> ORGANISM: Homo sapiens

<400> SEQUENCE: 16

Met Asn Gly Arg Ala Asp Phe Arg Glu Pro Asn Ala Glu Val Pro Arg
1               5                   10                  15

Pro Ile Pro His Ile Gly Pro Asp Tyr Ile Pro Thr Glu Glu Glu Arg
            20                  25                  30

Arg Val Phe Ala Glu Cys Asn Asp Glu Ser Phe Trp Phe Arg Ser Val
        35                  40                  45

Pro Leu Ala Ala Thr Ser Met Leu Ile Thr Gln Gly Leu Ile Ser Lys
    50                  55                  60

Gly Ile Leu Ser Ser His Pro Lys Tyr Gly Ser Ile Pro Lys Leu Ile
65                  70                  75                  80

Leu Ala Cys Ile Met Gly Tyr Phe Ala Gly Lys Leu Ser Tyr Val Lys
                85                  90                  95

Thr Cys Gln Glu Lys Phe Lys Lys Leu Glu Asn Ser Pro Leu Gly Glu
            100                 105                 110

Ala Leu Arg Ser Gly Gln Ala Arg Arg Ser Ser Pro Pro Gly His Tyr
        115                 120                 125

Tyr Gln Lys Ser Lys Tyr Asp Ser Ser Val Ser Gly Gln Ser Ser Phe
    130                 135                 140

Val Thr Ser Pro Ala Ala Asp Asn Ile Glu Met Leu Pro His Tyr Glu
145                 150                 155                 160

Pro Ile Pro Phe Ser Ser Met Asn Glu Ser Ala Pro Thr Gly Ile
                165                 170                 175

Thr Asp His Ile Val Gln Gly Pro Asp Pro Asn Leu Glu Glu Ser Pro
            180                 185                 190

Lys Arg Lys Asn Ile Thr Tyr Glu Glu Leu Arg Asn Lys Asn Arg Glu
        195                 200                 205

Ser Tyr Glu Val Ser Leu Thr Gln Lys Thr Asp Pro Ser Val Arg Pro
    210                 215                 220

Met His Glu Arg Val Pro Lys Lys Glu Val Lys Val Asn Lys Tyr Gly
225                 230                 235                 240

Asp Thr Trp Asp Glu
                245

<210> SEQ ID NO 17
<211> LENGTH: 609
<212> TYPE: PRT
<213> ORGANISM: Homo sapiens

<400> SEQUENCE: 17

Met Lys Trp Val Thr Phe Ile Ser Leu Leu Phe Leu Phe Ser Ser Ala
```

-continued

```
1               5                   10                  15
Tyr Ser Arg Gly Val Phe Arg Arg Asp Ala His Lys Ser Glu Val Ala
                20                  25                  30
His Arg Phe Lys Asp Leu Gly Glu Glu Asn Phe Lys Ala Leu Val Leu
                35                  40                  45
Ile Ala Phe Ala Gln Tyr Leu Gln Gln Cys Pro Phe Glu Asp His Val
                50                  55                  60
Lys Leu Val Asn Glu Val Thr Glu Phe Ala Lys Thr Cys Val Ala Asp
65                  70                  75                  80
Glu Ser Ala Glu Asn Cys Asp Lys Ser Leu His Thr Leu Phe Gly Asp
                    85                  90                  95
Lys Leu Cys Thr Val Ala Thr Leu Arg Glu Thr Tyr Gly Glu Met Ala
                100                 105                 110
Asp Cys Cys Ala Lys Gln Glu Pro Glu Arg Asn Glu Cys Phe Leu Gln
                115                 120                 125
His Lys Asp Asp Asn Pro Asn Leu Pro Arg Leu Val Arg Pro Glu Val
                130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
                180                 185                 190
Cys Gln Ala Ala Asp Lys Ala Ala Cys Leu Leu Pro Lys Leu Asp Glu
                195                 200                 205
Leu Arg Asp Glu Gly Lys Ala Ser Ser Ala Lys Gln Arg Leu Lys Cys
                210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                    245                 250                 255
Lys Leu Val Thr Asp Leu Thr Lys Val His Thr Glu Cys Cys His Gly
                260                 265                 270
Asp Leu Leu Glu Cys Ala Asp Asp Arg Ala Asp Leu Ala Lys Tyr Ile
                275                 280                 285
Cys Glu Asn Gln Asp Ser Ile Ser Ser Lys Leu Lys Glu Cys Cys Glu
                290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                    325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
                355                 360                 365
Leu Leu Leu Arg Leu Ala Lys Thr Tyr Glu Thr Thr Leu Glu Lys Cys
                370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                    405                 410                 415
Glu Leu Phe Glu Gln Leu Gly Glu Tyr Lys Phe Gln Asn Ala Leu Leu
                420                 425                 430
```

```
Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ser Gln Ala Ala Leu Gly Leu
            595                 600                 605

Leu

<210> SEQ ID NO 18
<211> LENGTH: 319
<212> TYPE: PRT
<213> ORGANISM: Homo sapiens

<400> SEQUENCE: 18

Met Ala Ser Ser Ala Ala Gly Cys Val Val Ile Val Gly Ser Gly Val
1               5                   10                  15

Ile Gly Arg Ser Trp Ala Met Leu Phe Ala Ser Gly Gly Phe Gln Val
                20                  25                  30

Lys Leu Tyr Asp Ile Glu Gln Gln Gln Ile Arg Asn Ala Leu Glu Asn
            35                  40                  45

Ile Arg Lys Glu Met Lys Leu Leu Glu Gln Ala Gly Ser Leu Lys Gly
        50                  55                  60

Ser Leu Ser Val Glu Glu Gln Leu Ser Leu Ile Ser Gly Cys Pro Asn
65                  70                  75                  80

Ile Gln Glu Ala Val Glu Gly Ala Met His Ile Gln Glu Cys Val Pro
                85                  90                  95

Glu Asp Leu Glu Leu Lys Lys Lys Ile Phe Ala Gln Leu Asp Ser Ile
            100                 105                 110

Ile Asp Asp Arg Val Ile Leu Ser Ser Ser Thr Ser Cys Leu Met Pro
        115                 120                 125

Ser Lys Leu Phe Ala Gly Leu Val His Val Lys Gln Cys Ile Val Ala
    130                 135                 140

His Pro Val Asn Pro Pro Tyr Tyr Ile Pro Leu Val Glu Leu Val Pro
145                 150                 155                 160

His Pro Glu Thr Ala Pro Thr Thr Val Asp Arg Thr His Ala Leu Met
                165                 170                 175

Lys Lys Ile Gly Gln Cys Pro Met Arg Val Gln Lys Glu Val Ala Gly
            180                 185                 190
```

```
Phe Val Leu Asn Arg Leu Gln Tyr Ala Ile Ile Ser Glu Ala Trp Arg
            195                 200                 205

Leu Val Glu Glu Gly Ile Val Ser Pro Ser Asp Leu Asp Leu Val Met
        210                 215                 220

Ser Glu Gly Leu Gly Met Arg Tyr Ala Phe Ile Gly Pro Leu Glu Thr
225                 230                 235                 240

Met His Leu Asn Ala Glu Gly Met Leu Ser Tyr Cys Asp Arg Tyr Ser
                245                 250                 255

Glu Gly Ile Lys His Val Leu Gln Thr Phe Gly Pro Ile Pro Glu Phe
            260                 265                 270

Ser Arg Ala Thr Ala Glu Lys Val Asn Gln Asp Met Cys Met Lys Val
        275                 280                 285

Pro Asp Asp Pro Glu His Leu Ala Ala Arg Arg Gln Trp Arg Asp Glu
    290                 295                 300

Cys Leu Met Arg Leu Ala Lys Leu Lys Ser Gln Val Gln Pro Gln
305                 310                 315

<210> SEQ ID NO 19
<211> LENGTH: 1391
<212> TYPE: PRT
<213> ORGANISM: Homo sapiens

<400> SEQUENCE: 19

Met Pro Ser Ser Leu Leu Gly Ala Ala Met Pro Ala Ser Thr Ser Ala
1               5                   10                  15

Ala Ala Leu Gln Glu Ala Leu Glu Asn Ala Gly Arg Leu Ile Asp Arg
            20                  25                  30

Gln Leu Gln Glu Asp Arg Met Tyr Pro Asp Leu Ser Glu Leu Leu Met
        35                  40                  45

Val Ser Ala Pro Asn Asn Pro Thr Val Ser Gly Met Ser Asp Met Asp
    50                  55                  60

Tyr Pro Leu Gln Gly Pro Gly Leu Leu Ser Val Pro Asn Leu Pro Glu
65                  70                  75                  80

Ile Ser Ser Ile Arg Arg Val Pro Leu Pro Pro Glu Leu Val Glu Gln
                85                  90                  95

Phe Gly His Met Gln Cys Asn Cys Met Met Gly Val Phe Pro Pro Ile
            100                 105                 110

Ser Arg Ala Trp Leu Thr Ile Asp Ser Asp Ile Phe Met Trp Asn Tyr
        115                 120                 125

Glu Asp Gly Gly Asp Leu Ala Tyr Phe Asp Gly Leu Ser Glu Thr Ile
    130                 135                 140

Leu Ala Val Gly Leu Val Lys Pro Lys Ala Gly Ile Phe Gln Pro His
145                 150                 155                 160

Val Arg His Leu Leu Val Leu Ala Thr Pro Val Asp Ile Val Ile Leu
                165                 170                 175

Gly Leu Ser Tyr Ala Asn Leu Gln Thr Gly Ser Gly Val Leu Asn Asp
            180                 185                 190

Ser Leu Ser Gly Gly Met Gln Leu Leu Pro Asp Pro Leu Tyr Ser Leu
        195                 200                 205

Pro Thr Asp Asn Thr Tyr Leu Leu Thr Ile Thr Ser Thr Asp Asn Gly
    210                 215                 220

Arg Ile Phe Leu Ala Gly Lys Asp Gly Cys Leu Tyr Glu Val Ala Tyr
225                 230                 235                 240

Gln Ala Glu Ala Gly Trp Phe Ser Gln Arg Cys Arg Lys Ile Asn His
```

-continued

```
                245                 250                 255
Ser Lys Ser Ser Leu Ser Phe Leu Val Pro Ser Leu Gln Phe Thr
            260                 265                 270
Phe Ser Glu Asp Pro Ile Leu Gln Ile Ala Ile Asp Asn Ser Arg
            275                 280                 285
Asn Ile Leu Tyr Thr Arg Ser Glu Lys Gly Val Ile Gln Val Tyr Asp
            290                 295                 300
Leu Gly Gln Asp Gly Gln Gly Met Ser Arg Val Ala Ser Val Ser Gln
305                 310                 315                 320
Asn Ala Ile Val Ser Ala Ala Gly Asn Ile Ala Arg Thr Ile Asp Arg
            325                 330                 335
Ser Val Phe Lys Pro Ile Val Gln Ile Ala Val Ile Glu Asn Ser Glu
            340                 345                 350
Ser Leu Asp Cys Gln Leu Leu Ala Val Thr His Ala Gly Val Arg Leu
            355                 360                 365
Tyr Phe Ser Thr Cys Pro Phe Arg Gln Pro Leu Ala Arg Pro Asn Thr
            370                 375                 380
Leu Thr Leu Val His Val Arg Leu Pro Pro Gly Phe Ser Ala Ser Ser
385                 390                 395                 400
Thr Val Glu Lys Pro Ser Lys Val His Arg Ala Leu Tyr Ser Lys Gly
            405                 410                 415
Ile Leu Leu Met Ala Ala Ser Glu Asn Glu Asp Asn Asp Ile Leu Trp
            420                 425                 430
Cys Val Asn His Asp Thr Phe Pro Phe Gln Lys Pro Met Met Glu Thr
            435                 440                 445
Gln Met Thr Ala Gly Val Asp Gly His Ser Trp Ala Leu Ser Ala Ile
            450                 455                 460
Asp Glu Leu Lys Val Asp Lys Ile Ile Thr Pro Leu Asn Lys Asp His
465                 470                 475                 480
Ile Pro Ile Thr Asp Ser Pro Val Val Gln Gln His Met Leu Pro
            485                 490                 495
Pro Lys Lys Phe Val Leu Leu Ser Ala Gln Gly Ser Leu Met Phe His
            500                 505                 510
Lys Leu Arg Pro Val Asp Gln Leu Arg His Leu Leu Val Ser Asn Val
            515                 520                 525
Gly Gly Asp Gly Glu Glu Ile Glu Arg Phe Phe Lys Leu His Gln Glu
            530                 535                 540
Asp Gln Ala Cys Ala Thr Cys Leu Ile Leu Ala Cys Ser Thr Ala Ala
545                 550                 555                 560
Cys Asp Arg Glu Val Ser Ala Trp Ala Thr Arg Ala Phe Phe Arg Tyr
            565                 570                 575
Gly Gly Glu Ala Gln Met Arg Phe Pro Thr Thr Leu Pro Pro Pro Ser
            580                 585                 590
Asn Val Gly Pro Ile Leu Gly Ser Pro Val Tyr Ser Ser Ser Pro Val
            595                 600                 605
Pro Ser Gly Ser Pro Tyr Pro Asn Pro Ser Phe Leu Gly Thr Pro Ser
            610                 615                 620
His Gly Ile Gln Pro Pro Ala Met Ser Thr Pro Val Cys Ala Leu Gly
625                 630                 635                 640
Asn Pro Ala Thr Gln Ala Thr Asn Met Ser Cys Val Thr Gly Pro Glu
            645                 650                 655
Ile Val Tyr Ser Gly Lys His Asn Gly Ile Cys Ile Tyr Phe Ser Arg
            660                 665                 670
```

```
Ile Met Gly Asn Ile Trp Asp Ala Ser Leu Val Val Glu Arg Ile Phe
            675                 680                 685

Lys Ser Gly Asn Arg Glu Ile Thr Ala Ile Glu Ser Ser Val Pro Cys
    690                 695                 700

Gln Leu Leu Glu Ser Val Leu Gln Glu Leu Lys Gly Leu Gln Glu Phe
705                 710                 715                 720

Leu Asp Arg Asn Ser Gln Phe Ala Gly Gly Pro Leu Gly Asn Pro Asn
                725                 730                 735

Thr Thr Ala Lys Val Gln Gln Arg Leu Ile Gly Phe Met Arg Pro Glu
            740                 745                 750

Asn Gly Asn Pro Gln Gln Met Gln Gln Glu Leu Gln Arg Lys Phe His
            755                 760                 765

Glu Ala Gln Leu Ser Glu Lys Ile Ser Leu Gln Ala Ile Gln Gln Leu
770                 775                 780

Val Arg Lys Ser Tyr Gln Ala Leu Ala Leu Trp Lys Leu Leu Cys Glu
785                 790                 795                 800

His Gln Phe Thr Ile Ile Val Ala Glu Leu Gln Lys Glu Leu Gln Glu
                805                 810                 815

Gln Leu Lys Ile Thr Thr Phe Lys Asp Leu Val Ile Arg Asp Lys Glu
            820                 825                 830

Leu Thr Gly Ala Leu Ile Ala Ser Leu Ile Asn Cys Tyr Ile Arg Asp
            835                 840                 845

Asn Ala Ala Val Asp Gly Ile Ser Leu His Leu Gln Asp Ile Cys Pro
850                 855                 860

Leu Leu Tyr Ser Thr Asp Asp Ala Ile Cys Ser Lys Ala Asn Glu Leu
865                 870                 875                 880

Leu Gln Arg Ser Arg Gln Val Gln Asn Lys Thr Glu Lys Glu Arg Met
                885                 890                 895

Leu Arg Glu Ser Leu Lys Glu Tyr Gln Lys Ile Ser Asn Gln Val Asp
            900                 905                 910

Leu Ser Asn Val Cys Ala Gln Tyr Arg Gln Val Arg Phe Tyr Glu Gly
            915                 920                 925

Val Val Glu Leu Ser Leu Thr Ala Ala Glu Lys Lys Asp Pro Gln Gly
930                 935                 940

Leu Gly Leu His Phe Tyr Lys His Gly Glu Pro Glu Glu Asp Ile Val
945                 950                 955                 960

Gly Leu Gln Ala Phe Gln Glu Arg Leu Asn Ser Tyr Lys Cys Ile Thr
                965                 970                 975

Asp Thr Leu Gln Glu Leu Val Asn Gln Ser Lys Ala Ala Pro Gln Ser
            980                 985                 990

Pro Ser Val Pro Lys Lys Pro Gly  Pro Pro Val Leu Ser  Ser Asp Pro
            995                 1000                1005

Asn Met  Leu Ser Asn Glu Glu  Ala Gly His His Phe  Glu Gln Met
   1010                1015                1020

Leu Lys  Leu Ser Gln Arg Ser  Lys Asp Glu Leu Phe  Ser Ile Ala
   1025                1030                1035

Leu Tyr  Asn Trp Leu Ile Gln  Val Asp Leu Ala Asp  Lys Leu Leu
   1040                1045                1050

Gln Val  Ala Ser Pro Phe Leu  Glu Pro His Leu Val  Arg Met Ala
   1055                1060                1065

Lys Val  Asp Gln Asn Arg Val  Arg Tyr Met Asp Leu  Leu Trp Arg
   1070                1075                1080
```

```
Tyr Tyr Glu Lys Asn Arg Ser Phe Ser Asn Ala Ala Arg Val Leu
    1085                1090                1095

Ser Arg Leu Ala Asp Met His Ser Thr Glu Ile Ser Leu Gln Gln
    1100                1105                1110

Arg Leu Glu Tyr Ile Ala Arg Ala Ile Leu Ser Ala Lys Ser Ser
    1115                1120                1125

Thr Ala Ile Ser Ser Ile Ala Ala Asp Gly Glu Phe Leu His Glu
    1130                1135                1140

Leu Glu Glu Lys Met Glu Val Ala Arg Ile Gln Leu Gln Ile Gln
    1145                1150                1155

Glu Thr Leu Gln Arg Gln Tyr Ser His His Ser Ser Val Gln Asp
    1160                1165                1170

Ala Val Ser Gln Leu Asp Ser Glu Leu Met Asp Ile Thr Lys Leu
    1175                1180                1185

Tyr Gly Glu Phe Ala Asp Pro Phe Lys Leu Ala Glu Cys Lys Leu
    1190                1195                1200

Ala Ile Ile His Cys Ala Gly Tyr Ser Asp Pro Ile Leu Val Gln
    1205                1210                1215

Thr Leu Trp Gln Asp Ile Ile Glu Lys Glu Leu Ser Asp Ser Val
    1220                1225                1230

Thr Leu Ser Ser Ser Asp Arg Met His Ala Leu Ser Leu Lys Ile
    1235                1240                1245

Val Leu Leu Gly Lys Ile Tyr Ala Gly Thr Pro Arg Phe Phe Pro
    1250                1255                1260

Leu Asp Phe Ile Val Gln Phe Leu Glu Gln Gln Val Cys Thr Leu
    1265                1270                1275

Asn Trp Asp Val Gly Phe Val Ile Gln Thr Met Asn Glu Ile Gly
    1280                1285                1290

Val Pro Leu Pro Arg Leu Leu Glu Val Tyr Asp Gln Leu Phe Lys
    1295                1300                1305

Ser Arg Asp Pro Phe Trp Asn Arg Met Lys Lys Pro Leu His Leu
    1310                1315                1320

Leu Asp Cys Ile His Val Leu Leu Ile Arg Tyr Val Glu Asn Pro
    1325                1330                1335

Ser Gln Val Leu Asn Cys Glu Arg Arg Phe Thr Asn Leu Cys
    1340                1345                1350

Leu Asp Ala Val Cys Gly Tyr Leu Val Glu Leu Gln Ser Met Ser
    1355                1360                1365

Ser Ser Val Ala Val Gln Ala Ile Thr Gly Asn Phe Lys Ser Leu
    1370                1375                1380

Gln Ala Lys Leu Glu Arg Leu His
    1385                1390

<210> SEQ ID NO 20
<211> LENGTH: 183
<212> TYPE: PRT
<213> ORGANISM: Homo sapiens

<400> SEQUENCE: 20

Met Ser Gln Lys Pro Ala Lys Glu Gly Pro Arg Leu Ser Lys Asn Gln
1               5                   10                  15

Lys Tyr Ser Glu His Phe Ser Ile His Cys Cys Pro Pro Phe Thr Phe
            20                  25                  30

Leu Asn Ser Lys Lys Glu Ile Val Asp Arg Lys Tyr Ser Ile Cys Lys
        35                  40                  45
```

-continued

Ser Gly Cys Phe Tyr Gln Lys Glu Glu Asp Trp Ile Cys Cys Ala
            50                  55                  60

Cys Gln Lys Thr Arg Thr Ser Arg Arg Ala Lys Ser Pro Gln Arg Pro
65                  70                  75                  80

Lys Gln Gln Pro Ala Ala Pro Ala Val Val Arg Ala Pro Ala Lys
                85                  90                  95

Pro Arg Ser Pro Pro Arg Ser Glu Arg Gln Pro Arg Ser Pro Arg
                100                 105                 110

Ser Glu Arg Gln Pro Arg Ser Pro Arg Ser Glu Arg Gln Pro Arg
            115                 120                 125

Ser Pro Pro Arg Ser Glu Arg Gln Pro Arg Pro Arg Pro Glu Val Arg
            130                 135                 140

Pro Pro Pro Ala Lys Gln Arg Pro Pro Gln Lys Ser Lys Gln Pro
145                 150                 155                 160

Arg Ser Ser Pro Leu Arg Gly Pro Gly Ala Ser Arg Gly Gly Ser Pro
                165                 170                 175

Val Lys Ala Ser Arg Phe Trp
                180

<210> SEQ ID NO 21
<211> LENGTH: 283
<212> TYPE: PRT
<213> ORGANISM: Homo sapiens

<400> SEQUENCE: 21

Met Val Ser Ala Ala Pro Ser Leu Leu Ile Leu Leu Leu Leu
1               5                   10                  15

Leu Gly Ser Val Pro Ala Thr Asp Ala Arg Ser Val Pro Leu Lys Ala
                20                  25                  30

Thr Phe Leu Glu Asp Val Ala Gly Ser Gly Glu Ala Glu Gly Ser Ser
            35                  40                  45

Ala Ser Ser Pro Ser Leu Pro Pro Pro Trp Thr Pro Ala Leu Ser Pro
        50                  55                  60

Thr Ser Met Gly Pro Gln Pro Ile Thr Leu Gly Gly Pro Ser Pro Pro
65                  70                  75                  80

Thr Asn Phe Leu Asp Gly Ile Val Asp Phe Phe Arg Gln Tyr Val Met
                85                  90                  95

Leu Ile Ala Val Val Gly Ser Leu Ala Phe Leu Leu Met Phe Ile Val
                100                 105                 110

Cys Ala Ala Val Ile Thr Arg Gln Lys Gln Lys Ala Ser Ala Tyr Tyr
            115                 120                 125

Pro Ser Ser Phe Pro Lys Lys Lys Tyr Val Asp Gln Ser Asp Arg Ala
        130                 135                 140

Gly Gly Pro Arg Ala Phe Ser Glu Val Pro Asp Arg Ala Pro Asp Ser
145                 150                 155                 160

Arg Pro Glu Glu Ala Leu Asp Ser Ser Arg Gln Leu Gln Ala Asp Ile
                165                 170                 175

Leu Ala Ala Thr Gln Asn Leu Lys Ser Pro Thr Arg Ala Ala Leu Gly
                180                 185                 190

Gly Gly Asp Gly Ala Arg Met Val Glu Gly Arg Gly Ala Glu Glu Glu
            195                 200                 205

Glu Lys Gly Ser Gln Glu Gly Asp Gln Glu Val Gln Gly His Gly Val
        210                 215                 220

Pro Val Glu Thr Pro Glu Ala Gln Glu Glu Pro Cys Ser Gly Val Leu

```
                    225                 230                 235                 240

Glu Gly Ala Val Val Ala Gly Glu Gly Gln Gly Glu Leu Gly Ser
                            245                 250                 255

Leu Leu Leu Ala Gln Glu Ala Gln Gly Pro Val Gly Pro Pro Glu Ser
                            260                 265                 270

Pro Cys Ala Cys Ser Ser Val His Pro Ser Val
                            275                 280

<210> SEQ ID NO 22
<211> LENGTH: 265
<212> TYPE: PRT
<213> ORGANISM: Homo sapiens

<400> SEQUENCE: 22

Met Cys Met Val Ile Phe Ala Pro Leu Phe Ala Ile Phe Ala Phe Ala
        1               5                   10                  15

Thr Cys Gly Gly Tyr Ser Gly Gly Leu Arg Leu Ser Val Asp Cys Val
                        20                  25                  30

Asn Lys Thr Glu Ser Asn Leu Ser Ile Asp Ile Ala Phe Ala Tyr Pro
                    35                  40                  45

Phe Arg Leu His Gln Val Thr Phe Glu Val Pro Thr Cys Glu Gly Lys
            50                  55                  60

Glu Arg Gln Lys Leu Ala Leu Ile Gly Asp Ser Ser Ser Ser Ala Glu
        65                  70                  75                  80

Phe Phe Val Thr Val Ala Val Phe Ala Phe Leu Tyr Ser Leu Ala Ala
                        85                  90                  95

Thr Val Val Tyr Ile Phe Phe Gln Asn Lys Tyr Arg Glu Asn Asn Arg
                    100                 105                 110

Gly Pro Leu Ile Asp Phe Ile Val Thr Val Val Phe Ser Phe Leu Trp
                115                 120                 125

Leu Val Gly Ser Ser Ala Trp Ala Lys Gly Leu Ser Asp Val Lys Val
        130                 135                 140

Ala Thr Asp Pro Lys Glu Val Leu Leu Leu Met Ser Ala Cys Lys Gln
        145                 150                 155                 160

Pro Ser Asn Lys Cys Met Ala Ile His Ser Pro Val Met Ser Ser Leu
                        165                 170                 175

Asn Thr Ser Val Val Phe Gly Phe Leu Asn Phe Ile Leu Trp Ala Gly
                    180                 185                 190

Asn Ile Trp Phe Val Phe Lys Glu Thr Gly Trp His Ser Ser Gly Gln
                195                 200                 205

Arg Tyr Leu Ser Asp Pro Met Glu Lys His Ser Ser Ser Tyr Asn Gln
            210                 215                 220

Gly Gly Tyr Asn Gln Asp Ser Tyr Gly Ser Ser Gly Tyr Ser Gln
        225                 230                 235                 240

Gln Ala Ser Leu Gly Pro Thr Ser Asp Glu Phe Gly Gln Gln Pro Thr
                        245                 250                 255

Gly Pro Thr Ser Phe Thr Asn Gln Ile
                        260                 265

<210> SEQ ID NO 23
<211> LENGTH: 1584
<212> TYPE: PRT
<213> ORGANISM: Homo sapiens

<400> SEQUENCE: 23

Met Ser Leu Thr Ser Trp Phe Leu Val Ser Ser Gly Gly Thr Arg His
```

-continued

```
1               5                    10                   15
Arg Leu Pro Arg Glu Met Ile Phe Val Gly Arg Asp Asp Cys Glu Leu
                20                  25                  30

Met Leu Gln Ser Arg Ser Val Asp Lys Gln His Ala Val Ile Asn Tyr
                35                  40                  45

Asp Ala Ser Thr Asp Glu His Leu Val Lys Asp Leu Gly Ser Leu Asn
    50                  55                  60

Gly Thr Phe Val Asn Asp Val Arg Ile Pro Glu Gln Thr Tyr Ile Thr
65                  70                  75                  80

Leu Lys Leu Glu Asp Lys Leu Arg Phe Gly Tyr Asp Thr Asn Leu Phe
                85                  90                  95

Thr Val Val Gln Gly Glu Met Arg Val Pro Glu Glu Ala Leu Lys His
                100                 105                 110

Glu Lys Phe Thr Ile Gln Leu Gln Leu Ser Gln Lys Ser Ser Glu Ser
            115                 120                 125

Glu Leu Ser Lys Ser Ala Ser Ala Lys Ser Ile Asp Ser Lys Val Ala
        130                 135                 140

Asp Ala Thr Glu Val Gln His Lys Thr Thr Glu Ala Leu Lys Ser
145                 150                 155                 160

Glu Glu Lys Ala Met Asp Ile Ser Ala Met Pro Arg Gly Thr Pro Leu
                165                 170                 175

Tyr Gly Gln Pro Ser Trp Trp Gly Asp Asp Glu Val Asp Glu Lys Arg
                180                 185                 190

Ala Phe Lys Thr Asn Gly Lys Pro Glu Glu Lys Asn His Glu Ala Gly
            195                 200                 205

Thr Ser Gly Cys Gly Ile Asp Ala Lys Gln Val Glu Glu Gln Ser Ala
    210                 215                 220

Ala Ala Asn Glu Glu Val Leu Phe Pro Phe Cys Arg Glu Pro Ser Tyr
225                 230                 235                 240

Phe Glu Ile Pro Thr Lys Glu Phe Gln Gln Pro Ser Gln Ile Thr Glu
                245                 250                 255

Ser Thr Ile His Glu Ile Pro Thr Lys Asp Thr Pro Ser Ser His Ile
            260                 265                 270

Thr Gly Ala Gly His Ala Ser Phe Thr Ile Glu Phe Asp Asp Ser Thr
        275                 280                 285

Pro Gly Lys Val Thr Ile Arg Asp His Val Thr Lys Phe Thr Ser Asp
    290                 295                 300

Gln Arg His Lys Ser Lys Lys Ser Ser Pro Gly Thr Gln Asp Leu Leu
305                 310                 315                 320

Gly Ile Gln Thr Gly Met Met Ala Pro Glu Asn Lys Val Ala Asp Trp
                325                 330                 335

Leu Ala Gln Asn Asn Pro Pro Gln Met Leu Trp Glu Arg Thr Glu Glu
                340                 345                 350

Asp Ser Lys Ser Ile Lys Ser Asp Val Pro Val Tyr Leu Lys Arg Leu
            355                 360                 365

Lys Gly Asn Lys His Asp Asp Gly Thr Gln Ser Asp Ser Glu Asn Ala
        370                 375                 380

Gly Ala His Arg Arg Cys Ser Lys Arg Ala Thr Leu Glu Glu His Leu
385                 390                 395                 400

Arg Arg His His Ser Glu His Lys Lys Leu Gln Lys Val Gln Ala Thr
                405                 410                 415

Glu Lys His Gln Asp Gln Ala Val Thr Ser Ser Ala His His Arg Gly
                420                 425                 430
```

```
Gly His Gly Val Pro His Gly Lys Leu Leu Lys Gln Lys Ser Glu Glu
            435                 440                 445

Pro Ser Val Ser Ile Pro Phe Leu Gln Thr Ala Leu Leu Arg Ser Ser
450                 455                 460

Gly Ser Leu Gly His Arg Pro Ser Gln Glu Met Asp Lys Met Leu Lys
465                 470                 475                 480

Asn Gln Ala Thr Ser Ala Thr Ser Glu Lys Asp Asn Asp Asp Asp Gln
                485                 490                 495

Ser Asp Lys Gly Thr Tyr Thr Ile Glu Leu Glu Asn Pro Asn Ser Glu
            500                 505                 510

Glu Val Glu Ala Arg Lys Met Ile Asp Lys Val Phe Gly Val Asp Asp
            515                 520                 525

Asn Gln Asp Tyr Asn Arg Pro Val Ile Asn Glu Lys His Lys Asp Leu
530                 535                 540

Ile Lys Asp Trp Ala Leu Ser Ser Ala Ala Val Met Glu Glu Arg
545                 550                 555                 560

Lys Pro Leu Thr Thr Ser Gly Phe His His Ser Glu Glu Gly Thr Ser
                565                 570                 575

Ser Ser Gly Ser Lys Arg Trp Val Ser Gln Trp Ala Ser Leu Ala Ala
            580                 585                 590

Asn His Thr Arg His Asp Gln Glu Glu Arg Ile Met Glu Phe Ser Ala
            595                 600                 605

Pro Leu Pro Leu Glu Asn Glu Thr Glu Ile Ser Glu Ser Gly Met Thr
610                 615                 620

Val Arg Ser Thr Gly Ser Ala Thr Ser Leu Ala Ser Gln Gly Glu Arg
625                 630                 635                 640

Arg Arg Arg Thr Leu Pro Gln Leu Pro Asn Glu Glu Lys Ser Leu Glu
                645                 650                 655

Ser His Arg Ala Lys Val Val Thr Gln Arg Ser Glu Ile Gly Glu Lys
            660                 665                 670

Gln Asp Thr Glu Leu Gln Glu Lys Glu Thr Pro Thr Gln Val Tyr Gln
            675                 680                 685

Lys Asp Lys Gln Asp Ala Asp Arg Pro Leu Ser Lys Met Asn Arg Ala
690                 695                 700

Val Asn Gly Glu Thr Leu Lys Thr Gly Gly Asp Asn Lys Thr Leu Leu
705                 710                 715                 720

His Leu Gly Ser Ser Ala Pro Gly Lys Glu Lys Ser Glu Thr Asp Lys
                725                 730                 735

Glu Thr Ser Leu Val Lys Gln Thr Leu Ala Lys Leu Gln Gln Gln Glu
            740                 745                 750

Gln Arg Glu Glu Ala Gln Trp Thr Pro Thr Lys Leu Ser Ser Lys Asn
            755                 760                 765

Val Ser Gly Gln Thr Asp Lys Cys Arg Glu Glu Thr Phe Lys Gln Glu
770                 775                 780

Ser Gln Pro Pro Glu Lys Asn Ser Gly His Ser Thr Ser Lys Gly Asp
785                 790                 795                 800

Arg Val Ala Gln Ser Glu Ser Lys Arg Lys Ala Glu Glu Ile Leu
                805                 810                 815

Lys Ser Gln Thr Pro Lys Gly Gly Asp Lys Glu Ser Ser Lys Ser
            820                 825                 830

Leu Val Arg Gln Gly Ser Phe Thr Ile Glu Lys Pro Ser Pro Asn Ile
            835                 840                 845
```

-continued

```
Pro Ile Glu Leu Ile Pro His Ile Asn Lys Gln Thr Ser Thr Pro
850                 855                 860

Ser Ser Leu Ala Leu Thr Ser Ala Ser Arg Ile Arg Glu Arg Ser Glu
865                 870                 875                 880

Ser Leu Asp Pro Asp Ser Ser Met Asp Thr Thr Leu Ile Leu Lys Asp
                885                 890                 895

Thr Glu Ala Val Met Ala Phe Leu Glu Ala Lys Leu Arg Glu Asp Asn
                900                 905                 910

Lys Thr Asp Glu Gly Pro Asp Thr Pro Ser Tyr Asn Arg Asp Asn Ser
                915                 920                 925

Ile Ser Pro Glu Ser Asp Val Asp Thr Ala Ser Thr Ile Ser Leu Val
930                 935                 940

Thr Gly Glu Thr Glu Arg Lys Ser Thr Gln Lys Arg Lys Ser Phe Thr
945                 950                 955                 960

Ser Leu Tyr Lys Asp Arg Cys Ser Thr Gly Ser Pro Ser Lys Asp Val
                965                 970                 975

Thr Lys Ser Ser Ser Gly Ala Arg Glu Lys Met Glu Lys Lys Thr
                980                 985                 990

Lys Ser Arg Ser Thr Asp Val Gly Ser Arg Ala Asp Gly Arg Lys Phe
                995                 1000                1005

Val Gln Ser Ser Gly Arg Ile Arg Gln Pro Ser Val Asp Leu Thr
    1010                1015                1020

Asp Asp Asp Gln Thr Ser Ser Val Pro His Ser Ala Ile Ser Asp
    1025                1030                1035

Ile Met Ser Ser Asp Gln Glu Thr Tyr Ser Cys Lys Pro His Gly
    1040                1045                1050

Arg Thr Pro Leu Thr Ser Ala Asp Glu His Val His Ser Lys Leu
    1055                1060                1065

Glu Gly Ser Lys Val Thr Lys Ser Lys Thr Ser Pro Val Val Ser
    1070                1075                1080

Gly Ser Ser Ser Lys Ser Thr Thr Leu Pro Arg Pro Arg Pro Thr
    1085                1090                1095

Arg Thr Ser Leu Leu Arg Arg Ala Arg Leu Gly Glu Ala Ser Asp
    1100                1105                1110

Ser Glu Leu Ala Asp Ala Asp Lys Ala Ser Val Ala Ser Glu Val
    1115                1120                1125

Ser Thr Thr Ser Ser Thr Ser Lys Pro Pro Thr Gly Arg Arg Asn
    1130                1135                1140

Ile Ser Arg Ile Asp Leu Leu Ala Gln Pro Arg Arg Thr Arg Leu
    1145                1150                1155

Gly Ser Leu Ser Ala Arg Ser Asp Ser Glu Ala Thr Ile Ser Arg
    1160                1165                1170

Ser Ser Ala Ser Ser Arg Thr Ala Glu Ala Ile Ile Arg Ser Gly
    1175                1180                1185

Ala Arg Leu Val Pro Ser Asp Lys Phe Ser Pro Arg Ile Arg Ala
    1190                1195                1200

Asn Ser Ile Ser Arg Leu Ser Asp Ser Lys Val Lys Ser Met Thr
    1205                1210                1215

Ser Ala His Gly Ser Ala Ser Val Asn Ser Arg Trp Arg Arg Phe
    1220                1225                1230

Pro Thr Asp Tyr Ala Ser Ser Glu Asp Glu Phe Gly Ser Asn
    1235                1240                1245

Arg Asn Ser Pro Lys His Thr Arg Leu Arg Thr Ser Pro Ala Leu
```

```
                1250                1255                1260

Lys Thr Thr Arg Leu Gln Ser Ala Gly Ser Ala Met Pro Thr Ser
    1265                1270                1275

Ser Ser Phe Lys His Arg Ile Lys Glu Gln Glu Asp Tyr Ile Arg
    1280                1285                1290

Asp Trp Thr Ala His Arg Glu Glu Ile Ala Arg Ile Ser Gln Asp
    1295                1300                1305

Leu Ala Leu Ile Ala Arg Glu Ile Asn Asp Val Ala Gly Glu Ile
    1310                1315                1320

Asp Ser Val Thr Ser Ser Gly Thr Ala Pro Ser Thr Thr Val Ser
    1325                1330                1335

Thr Ala Ala Thr Thr Pro Gly Ser Ala Ile Asp Thr Arg Glu Glu
    1340                1345                1350

Leu Val Asp Arg Val Phe Asp Glu Ser Leu Asn Phe Arg Lys Ile
    1355                1360                1365

Pro Pro Leu Val His Ser Lys Thr Pro Glu Gly Asn Asn Gly Arg
    1370                1375                1380

Ser Gly Asp Pro Arg Pro Gln Ala Ala Glu Pro Pro Asp His Leu
    1385                1390                1395

Thr Ile Thr Arg Arg Arg Thr Trp Ser Arg Asp Glu Val Met Gly
    1400                1405                1410

Asp Asn Leu Leu Leu Ser Ser Val Phe Gln Phe Ser Lys Lys Ile
    1415                1420                1425

Arg Gln Ser Ile Asp Lys Thr Ala Gly Lys Ile Arg Ile Leu Phe
    1430                1435                1440

Lys Asp Lys Asp Arg Asn Trp Asp Asp Ile Glu Ser Lys Leu Arg
    1445                1450                1455

Ala Glu Ser Glu Val Pro Ile Val Lys Thr Ser Ser Met Glu Ile
    1460                1465                1470

Ser Ser Ile Leu Gln Glu Leu Lys Arg Val Glu Lys Gln Leu Gln
    1475                1480                1485

Ala Ile Asn Ala Met Ile Asp Pro Asp Gly Thr Leu Glu Ala Leu
    1490                1495                1500

Asn Asn Met Gly Phe Pro Ser Ala Met Leu Pro Ser Pro Pro Lys
    1505                1510                1515

Gln Lys Ser Ser Pro Val Asn His His Ser Pro Gly Gln Thr
    1520                1525                1530

Pro Thr Leu Gly Gln Pro Glu Ala Arg Ala Leu His Pro Ala Ala
    1535                1540                1545

Val Ser Ala Ala Ala Glu Phe Glu Asn Ala Ser Glu Ala Asp
    1550                1555                1560

Phe Ser Ile His Phe Asn Arg Phe Asn Pro Asp Gly Glu Glu Glu
    1565                1570                1575

Asp Val Thr Val Gln Glu
    1580

<210> SEQ ID NO 24
<211> LENGTH: 381
<212> TYPE: PRT
<213> ORGANISM: Homo sapiens

<400> SEQUENCE: 24

Met Ala Ser Pro Pro Ala Cys Pro Ser Glu Glu Asp Glu Ser Leu Lys
1               5                   10                  15
```

Gly Cys Glu Leu Tyr Val Gln Leu His Gly Ile Gln Gln Val Leu Lys
            20                  25                  30

Asp Cys Ile Val His Leu Cys Ile Ser Lys Pro Glu Arg Pro Met Lys
            35                  40                  45

Phe Leu Arg Glu His Phe Glu Lys Leu Glu Lys Glu Glu Asn Arg Gln
        50                  55                  60

Ile Leu Ala Arg Gln Lys Ser Asn Ser Gln Ser Asp Ser His Asp Glu
65                  70                  75                  80

Glu Val Ser Pro Thr Pro Pro Asn Pro Val Val Lys Ala Arg Arg Arg
                    85                  90                  95

Arg Gly Gly Val Ser Ala Glu Val Tyr Thr Glu Glu Asp Ala Val Ser
                100                 105                 110

Tyr Val Arg Lys Val Ile Pro Lys Asp Tyr Lys Thr Met Thr Ala Leu
            115                 120                 125

Ala Lys Ala Ile Ser Lys Asn Val Leu Phe Ala His Leu Asp Asp Asn
        130                 135                 140

Glu Arg Ser Asp Ile Phe Asp Ala Met Phe Pro Val Thr His Ile Ala
145                 150                 155                 160

Gly Glu Thr Val Ile Gln Gln Gly Asn Glu Gly Asp Asn Phe Tyr Val
                    165                 170                 175

Val Asp Gln Gly Glu Val Asp Val Tyr Val Asn Gly Glu Trp Val Thr
                180                 185                 190

Asn Ile Ser Glu Gly Gly Ser Phe Gly Glu Leu Ala Leu Ile Tyr Gly
            195                 200                 205

Thr Pro Arg Ala Ala Thr Val Lys Ala Lys Thr Asp Leu Lys Leu Trp
        210                 215                 220

Gly Ile Asp Arg Asp Ser Tyr Arg Arg Ile Leu Met Gly Ser Thr Leu
225                 230                 235                 240

Arg Lys Arg Lys Met Tyr Glu Glu Phe Leu Ser Lys Val Ser Ile Leu
                    245                 250                 255

Glu Ser Leu Glu Lys Trp Glu Arg Leu Thr Val Ala Asp Ala Leu Glu
                260                 265                 270

Pro Val Gln Phe Glu Asp Gly Glu Lys Ile Val Val Gln Gly Glu Pro
            275                 280                 285

Gly Asp Asp Phe Tyr Ile Ile Thr Glu Gly Thr Ala Ser Val Leu Gln
        290                 295                 300

Arg Arg Ser Pro Asn Glu Glu Tyr Val Glu Val Gly Arg Leu Gly Pro
305                 310                 315                 320

Ser Asp Tyr Phe Gly Glu Ile Ala Leu Leu Asn Arg Pro Arg Ala
                    325                 330                 335

Ala Thr Val Val Ala Arg Gly Pro Leu Lys Cys Val Lys Leu Asp Arg
                340                 345                 350

Pro Arg Phe Glu Arg Val Leu Gly Pro Cys Ser Glu Ile Leu Lys Arg
            355                 360                 365

Asn Ile Gln Arg Tyr Asn Ser Phe Ile Ser Leu Thr Val
        370                 375                 380

<210> SEQ ID NO 25
<211> LENGTH: 400
<212> TYPE: PRT
<213> ORGANISM: Homo sapiens

<400> SEQUENCE: 25

Met Gly Val Leu Met Ser Lys Arg Gln Thr Val Glu Gln Val Gln Lys
1               5                   10                  15

Val Ser Leu Ala Val Ser Ala Phe Lys Asp Gly Leu Arg Asp Arg Pro
        20                  25                  30

Ser Ile Arg Arg Thr Gly Glu Leu Pro Gly Ser Arg Gly Thr Val
    35                  40                  45

Glu Gly Ser Val Gln Glu Val Gln Glu Glu Lys Glu Ala Glu Ala Gly
50                  55                  60

Thr Ser Val Val Gln Glu Glu Ser Ser Ala Gly Arg Ala Ala Trp Glu
65                  70                  75                  80

Arg Leu Arg Asp Gly Arg Gly Val Glu Pro Glu Glu Phe Asp Arg Thr
                85                  90                  95

Ser Arg Phe Thr Pro Pro Ala Phe Ile Arg Pro Thr Arg Lys Leu Asp
            100                 105                 110

Asp Asp Lys Pro Pro Glu Ile Cys Leu Glu Pro Arg Glu Pro Val Val
        115                 120                 125

Asn Asp Glu Met Cys Asp Val Cys Glu Val Trp Thr Ala Glu Ser Leu
130                 135                 140

Phe Pro Cys Arg Val Cys Thr Arg Val Phe His Asp Gly Cys Leu Arg
145                 150                 155                 160

Arg Met Gly Tyr Ile Gln Gly Asp Ser Ala Ala Glu Val Thr Glu Met
                165                 170                 175

Ala His Thr Glu Thr Gly Trp Ser Cys His Tyr Cys Asp Asn Ile Asn
            180                 185                 190

Leu Leu Leu Thr Glu Glu Glu Met Tyr Ser Leu Thr Glu Thr Phe Gln
        195                 200                 205

Arg Cys Lys Val Ile Pro Asp Cys Ser Leu Thr Leu Glu Asp Phe Leu
210                 215                 220

Arg Tyr Arg His Gln Ala Ala Lys Arg Gly Asp Arg Asp Arg Ala Leu
225                 230                 235                 240

Ser Glu Glu Gln Glu Glu Gln Ala Ala Arg Gln Phe Ala Ala Leu Asp
                245                 250                 255

Pro Glu His Arg Gly His Ile Glu Trp Pro Asp Phe Leu Ser His Glu
            260                 265                 270

Ser Leu Leu Leu Leu Gln Gln Leu Arg Pro Gln Asn Ser Leu Leu Arg
        275                 280                 285

Leu Leu Thr Val Lys Glu Arg Glu Arg Ala Arg Ala Ala Phe Leu Ala
290                 295                 300

Arg Gly Ser Gly Ser Thr Val Ser Glu Ala Glu Cys Arg Arg Ala Gln
305                 310                 315                 320

His Ser Trp Phe Cys Lys Arg Phe Pro Glu Ala Pro Ser Cys Ser Val
                325                 330                 335

Ser Ile Ser His Val Gly Pro Ile Ala Asp Ser Ser Pro Ala Ser Ser
            340                 345                 350

Ser Ser Lys Ser Gln Asp Lys Thr Leu Leu Pro Thr Glu Gln Glu Ser
        355                 360                 365

Arg Phe Val Asp Trp Pro Thr Phe Leu Gln Glu Asn Val Leu Tyr Ile
370                 375                 380

Leu Ala Ala Arg Pro Asn Ser Ala Ala Ile His Leu Lys Pro Pro Gly
385                 390                 395                 400

<210> SEQ ID NO 26
<211> LENGTH: 446
<212> TYPE: PRT
<213> ORGANISM: Homo sapiens

<400> SEQUENCE: 26

```
Met Arg Glu Cys Leu Ser Ile His Ile Gly Gln Ala Gly Ile Gln Ile
1               5                   10                  15
Gly Asp Ala Cys Trp Glu Leu Tyr Cys Leu Glu His Gly Ile Gln Pro
            20                  25                  30
Asn Gly Val Val Leu Asp Thr Gln Gln Asp Gln Leu Glu Asn Ala Lys
        35                  40                  45
Met Glu His Thr Asn Ala Ser Phe Asp Thr Phe Phe Cys Glu Thr Arg
50                  55                  60
Ala Gly Lys His Val Pro Arg Ala Leu Phe Val Asp Leu Glu Pro Thr
65                  70                  75                  80
Val Ile Asp Gly Ile Arg Thr Gly Gln His Arg Ser Leu Phe His Pro
                85                  90                  95
Glu Gln Leu Leu Ser Gly Lys Glu Asp Ala Ala Asn Asn Tyr Ala Arg
            100                 105                 110
Gly Arg Tyr Ser Val Gly Ser Glu Val Ile Asp Leu Val Leu Glu Arg
        115                 120                 125
Thr Arg Lys Leu Ala Glu Gln Cys Gly Gly Leu Gln Gly Phe Leu Ile
130                 135                 140
Phe Arg Ser Phe Gly Gly Gly Thr Gly Ser Gly Phe Thr Ser Leu Leu
145                 150                 155                 160
Met Glu Arg Leu Thr Gly Glu Tyr Ser Arg Lys Thr Lys Leu Glu Phe
                165                 170                 175
Ser Val Tyr Pro Ala Pro Arg Ile Ser Thr Ala Val Val Glu Pro Tyr
            180                 185                 190
Asn Ser Val Leu Thr Thr His Ser Thr Thr Glu His Thr Asp Cys Thr
        195                 200                 205
Phe Met Val Asp Asn Glu Ala Val Tyr Asp Ile Cys His Arg Lys Leu
210                 215                 220
Gly Val Glu Cys Pro Ser His Ala Ser Ile Asn Arg Leu Val Val Gln
225                 230                 235                 240
Val Val Ser Ser Ile Thr Ala Ser Leu Arg Phe Glu Gly Pro Leu Asn
                245                 250                 255
Val Asp Leu Ile Glu Phe Gln Thr Asn Leu Val Pro Tyr Pro Arg Ile
            260                 265                 270
His Phe Pro Met Thr Ala Phe Ala Pro Ile Val Ser Ala Asp Lys Ala
        275                 280                 285
Tyr His Glu Gln Phe Ser Val Ser Asp Ile Thr Thr Ala Cys Phe Glu
290                 295                 300
Ser Ser Asn Gln Leu Val Lys Cys Asp Pro Arg Leu Gly Lys Tyr Met
305                 310                 315                 320
Ala Cys Cys Leu Leu Tyr Arg Gly Asp Val Val Pro Lys Glu Val Asn
                325                 330                 335
Ala Ala Ile Ala Ala Thr Lys Ser Arg His Ser Val Gln Phe Val Asp
            340                 345                 350
Trp Cys Pro Thr Gly Phe Lys Val Gly Ile Asn Asn Arg Pro Pro Thr
        355                 360                 365
Val Met Pro Gly Gly Asp Leu Ala Lys Val His Arg Ser Ile Cys Met
370                 375                 380
Leu Ser Asn Thr Thr Ala Ile Val Glu Ala Trp Ala Arg Leu Asp His
385                 390                 395                 400
Lys Phe Asp Leu Met Tyr Ala Lys Arg Ala Phe Leu His Trp Tyr Leu
                405                 410                 415
```

Arg Glu Gly Met Glu Glu Ala Glu Phe Leu Glu Ala Arg Glu Asp Leu
            420                 425                 430

Ala Ala Leu Glu Arg Asp Tyr Glu Val Ala Gln Ser Phe
            435                 440                 445

<210> SEQ ID NO 27
<211> LENGTH: 345
<212> TYPE: PRT
<213> ORGANISM: Homo sapiens

<400> SEQUENCE: 27

Met Pro Arg Ile Asp Ala Asp Leu Lys Leu Asp Phe Lys Asp Val Leu
1               5                   10                  15

Leu Arg Pro Lys Arg Ser Ser Leu Lys Ser Arg Ala Glu Val Asp Leu
            20                  25                  30

Glu Arg Thr Phe Thr Phe Arg Asn Ser Lys Gln Thr Tyr Ser Gly Ile
        35                  40                  45

Pro Ile Ile Val Ala Asn Met Asp Thr Val Gly Thr Phe Glu Met Ala
    50                  55                  60

Ala Val Met Ser Gln His Ser Met Phe Thr Ala Ile His Lys His Tyr
65                  70                  75                  80

Ser Leu Asp Asp Trp Lys Leu Phe Ala Thr Asn His Pro Glu Cys Leu
                85                  90                  95

Gln Asn Val Ala Val Ser Ser Gly Ser Gly Gln Asn Asp Leu Glu Lys
            100                 105                 110

Met Thr Ser Ile Leu Glu Ala Val Pro Gln Val Lys Phe Ile Cys Leu
        115                 120                 125

Asp Val Ala Asn Gly Tyr Ser Glu His Phe Val Glu Phe Val Lys Leu
    130                 135                 140

Val Arg Ala Lys Phe Pro Glu His Thr Ile Met Ala Gly Asn Val Val
145                 150                 155                 160

Thr Gly Glu Met Val Glu Glu Leu Ile Leu Ser Gly Ala Asp Ile Ile
                165                 170                 175

Lys Val Gly Val Gly Pro Gly Ser Val Cys Thr Thr Arg Thr Lys Thr
            180                 185                 190

Gly Val Gly Tyr Pro Gln Leu Ser Ala Val Ile Glu Cys Ala Asp Ser
        195                 200                 205

Ala His Gly Leu Lys Gly His Ile Ile Ser Asp Gly Gly Cys Thr Cys
    210                 215                 220

Pro Gly Asp Val Ala Lys Ala Phe Gly Ala Gly Ala Asp Phe Val Met
225                 230                 235                 240

Leu Gly Gly Met Phe Ser Gly His Thr Glu Cys Ala Gly Glu Val Phe
                245                 250                 255

Glu Arg Asn Gly Arg Lys Leu Lys Leu Phe Tyr Gly Met Ser Ser Asp
            260                 265                 270

Thr Ala Met Asn Lys His Ala Gly Gly Val Ala Glu Tyr Arg Ala Ser
        275                 280                 285

Glu Gly Lys Thr Val Glu Val Pro Tyr Lys Gly Asp Val Glu Asn Thr
    290                 295                 300

Ile Leu Asp Ile Leu Gly Gly Leu Arg Ser Thr Cys Thr Tyr Val Gly
305                 310                 315                 320

Ala Ala Lys Leu Lys Glu Leu Ser Arg Arg Ala Thr Phe Ile Arg Val
                325                 330                 335

Thr Gln Gln His Asn Thr Val Phe Ser

```
<210> SEQ ID NO 28
<211> LENGTH: 176
<212> TYPE: PRT
<213> ORGANISM: Homo sapiens

<400> SEQUENCE: 28

Met Asp Leu Pro Asp Ser Ala Ser Arg Val Phe Cys Gly Arg Ile Leu
1               5                   10                  15

Ser Met Val Asn Thr Asp Asp Val Asn Ala Ile Ile Leu Ala Gln Lys
            20                  25                  30

Asn Met Leu Asp Arg Phe Glu Lys Thr Asn Glu Met Leu Leu Asn Phe
        35                  40                  45

Asn Asn Leu Ser Ser Ala Arg Leu Gln Gln Met Ser Glu Arg Phe Leu
    50                  55                  60

His His Thr Arg Thr Leu Val Glu Met Lys Arg Asp Leu Asp Ser Ile
65                  70                  75                  80

Phe Arg Arg Ile Arg Thr Leu Lys Gly Lys Leu Ala Arg Gln His Pro
                85                  90                  95

Glu Ala Phe Ser His Ile Pro Glu Ala Ser Phe Leu Glu Glu Glu Asp
            100                 105                 110

Glu Asp Pro Ile Pro Pro Ser Thr Thr Thr Thr Ile Ala Thr Ser Glu
        115                 120                 125

Gln Ser Thr Gly Ser Cys Asp Thr Ser Pro Asp Thr Val Ser Pro Ser
    130                 135                 140

Leu Ser Pro Gly Phe Glu Asp Leu Ser His Val Gln Pro Gly Ser Pro
145                 150                 155                 160

Ala Ile Asn Gly Arg Ser Gln Thr Asp Asp Glu Glu Met Thr Gly Glu
                165                 170                 175

<210> SEQ ID NO 29
<211> LENGTH: 758
<212> TYPE: PRT
<213> ORGANISM: Homo sapiens

<400> SEQUENCE: 29

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
```

```
            145                 150                 155                 160
        Glu Gly Pro Arg Glu Ala Thr Arg Gln Pro Ser Gly Thr Gly Pro Glu
                        165                 170                 175
        Asp Thr Glu Gly Gly Arg His Ala Pro Glu Leu Leu Lys His Gln Leu
                        180                 185                 190
        Leu Gly Asp Leu His Gln Glu Gly Pro Pro Leu Lys Gly Ala Gly Gly
                        195                 200                 205
        Lys Glu Arg Pro Gly Ser Lys Glu Val Asp Glu Arg Asp Val
                        210                 215                 220
        Asp Glu Ser Ser Pro Gln Asp Ser Pro Ser Lys Ala Ser Pro Ala
        225                 230                 235                 240
        Gln Asp Gly Arg Pro Pro Gln Thr Ala Ala Arg Glu Ala Thr Ser Ile
                        245                 250                 255
        Pro Gly Phe Pro Ala Glu Gly Ala Ile Pro Leu Pro Val Asp Phe Leu
                        260                 265                 270
        Ser Lys Val Ser Thr Glu Ile Pro Ala Ser Glu Pro Asp Gly Pro Ser
                        275                 280                 285
        Val Gly Arg Ala Lys Gly Gln Asp Ala Pro Leu Glu Phe Thr Phe His
                        290                 295                 300
        Val Glu Ile Thr Pro Asn Val Gln Lys Glu Gln Ala His Ser Glu Glu
        305                 310                 315                 320
        His Leu Gly Arg Ala Ala Phe Pro Gly Ala Pro Gly Glu Gly Pro Glu
                        325                 330                 335
        Ala Arg Gly Pro Ser Leu Gly Glu Asp Thr Lys Glu Ala Asp Leu Pro
                        340                 345                 350
        Glu Pro Ser Glu Lys Gln Pro Ala Ala Ala Pro Arg Gly Lys Pro Val
                        355                 360                 365
        Ser Arg Val Pro Gln Leu Lys Ala Arg Met Val Ser Lys Ser Lys Asp
                        370                 375                 380
        Gly Thr Gly Ser Asp Asp Lys Lys Ala Lys Thr Ser Thr Arg Ser Ser
        385                 390                 395                 400
        Ala Lys Thr Leu Lys Asn Arg Pro Cys Leu Ser Pro Lys His Pro Thr
                        405                 410                 415
        Pro Gly Ser Ser Asp Pro Leu Ile Gln Pro Ser Ser Pro Ala Val Cys
                        420                 425                 430
        Pro Glu Pro Pro Ser Ser Pro Lys Tyr Val Ser Ser Val Thr Ser Arg
                        435                 440                 445
        Thr Gly Ser Ser Gly Ala Lys Glu Met Lys Leu Lys Gly Ala Asp Gly
                        450                 455                 460
        Lys Thr Lys Ile Ala Thr Pro Arg Gly Ala Ala Pro Pro Gly Gln Lys
        465                 470                 475                 480
        Gly Gln Ala Asn Ala Thr Arg Ile Pro Ala Lys Thr Pro Pro Ala Pro
                        485                 490                 495
        Lys Thr Pro Pro Ser Ser Gly Glu Pro Pro Lys Ser Gly Asp Arg Ser
                        500                 505                 510
        Gly Tyr Ser Ser Pro Gly Ser Pro Gly Thr Pro Gly Ser Arg Ser Arg
                        515                 520                 525
        Thr Pro Ser Leu Pro Thr Pro Pro Thr Arg Glu Pro Lys Lys Val Ala
                        530                 535                 540
        Val Val Arg Thr Pro Pro Lys Ser Pro Ser Ser Ala Lys Ser Arg Leu
        545                 550                 555                 560
        Gln Thr Ala Pro Val Pro Met Pro Asp Leu Lys Asn Val Lys Ser Lys
                        565                 570                 575
```

```
Ile Gly Ser Thr Glu Asn Leu Lys His Gln Pro Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
        610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gln Val Glu Val
            645                 650                 655

Lys Ser Glu Lys Leu Asp Phe Lys Asp Arg Val Gln Ser Lys Ile Gly
        660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
        690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
            725                 730                 735

Val Asp Ser Pro Gln Leu Ala Thr Leu Ala Asp Glu Val Ser Ala Ser
            740                 745                 750

Leu Ala Lys Gln Gly Leu
            755

<210> SEQ ID NO 30
<211> LENGTH: 161
<212> TYPE: PRT
<213> ORGANISM: Homo sapiens

<400> SEQUENCE: 30

Met Ala Ala Ala Leu Phe Val Leu Leu Gly Phe Ala Leu Leu Gly Thr
1               5                   10                  15

His Gly Ala Ser Gly Ala Glu Asp Leu Gly Ser Lys Ile Leu Leu Thr
            20                  25                  30

Cys Ser Leu Asn Asp Ser Ala Thr Glu Val Thr Gly His Arg Trp Leu
        35                  40                  45

Lys Gly Gly Val Val Leu Lys Glu Asp Ala Leu Pro Gly Gln Lys Thr
    50                  55                  60

Glu Phe Lys Val Asp Ser Asp Gln Trp Gly Glu Tyr Ser Cys Val
65                  70                  75                  80

Phe Leu Pro Glu Pro Met Gly Thr Ala Asn Ile Gln Leu His Gly Pro
            85                  90                  95

Pro Arg Val Lys Ala Val Lys Ser Ser Glu His Ile Asn Glu Gly Glu
            100                 105                 110

Thr Ala Met Leu Val Cys Lys Ser Glu Ser Val Pro Pro Val Thr Asp
        115                 120                 125

Trp Ala Trp Tyr Lys Ile Thr Asp Ser Glu Asp Lys Ala Leu Met Asn
    130                 135                 140

Gly Ser Glu Ser Arg Phe Phe Val Ser Ser Ser Gln Gly Arg Ser Glu
145                 150                 155                 160

Leu

<210> SEQ ID NO 31
```

```
<211> LENGTH: 79
<212> TYPE: PRT
<213> ORGANISM: Homo sapiens

<400> SEQUENCE: 31

Met Tyr Tyr Lys Phe Ser Gly Phe Thr Gln Lys Leu Ala Gly Ala Trp
1               5                   10                  15

Ala Ser Glu Ala Tyr Ser Pro Gln Gly Leu Lys Pro Val Val Ser Thr
                20                  25                  30

Glu Ala Pro Pro Ile Ile Phe Ala Thr Pro Thr Lys Leu Thr Ser Asp
            35                  40                  45

Ser Thr Val Tyr Asp Tyr Ala Gly Lys Asn Lys Val Pro Glu Leu Gln
        50                  55                  60

Lys Phe Phe Gln Val Arg Glu Asp Thr Leu Gln Gln Lys Ser Leu
65                  70                  75
```

BIOMOLECULES INVOLVED IN ALZHEIMER'S DISEASE

CROSS-REFERENCE TO RELATED APPLICATIONS

This application is the U.S. National Stage Application of International Patent Application No. PCT/EP2016/062090 filed on May 27, 2016, which claims priority to GB Application No. 1509134.1, filed on May 28, 2015, and GB Application No. 1512596.6, filed on Jul. 17, 2015, the contents of each of which is incorporated herein by reference in its entirety.

FIELD OF THE INVENTION

The invention relates to sets of biomarkers and methods using thereof for diagnosing, staging, treating and assessing the response of a treatment for a neurocognitive disorder characterised by tau toxicity, in particular for Alzheimer's disease.

BACKGROUND OF THE INVENTION

Neurofibrillary tangles, composed of intracellular aggregates of tau protein, are a key neuropathological feature of Alzheimer's disease (AD) and other neurodegenerative diseases, collectively termed tauopathies. Tau is an intracellular microtubule-associated protein, with several unique characteristics such as natively unfolded conformation, thermostability, acid-stability, and capability of post-translational modifications.

Abnormally hyperphosphorylated tau is a key feature of human tauopathies. In AD pathogenesis, accumulation of the amyloid-μ peptide (Aβ) interacts with the signalling pathways that regulate the phosphorylation of tau. Hyperphosphorylation of tau disrupts its normal function in regulating axonal transport and leads to the accumulation of neurofibrillary tangles and toxic species of soluble tau.

Currently there is no cure for AD. Approved treatments are few and of limited efficacy, serving mostly to slow or delay progression.

Identification and development of new therapies for the treatment of AD and other tauopathies is also greatly affected by the lack of effective diagnostic, prognostic and predictive biomarkers and by the lack of new targets for the design of new therapies. Currently, AD can only be definitively diagnosed by brain biopsy or upon autopsy after a patient has died. Clearly, in clinical settings, brain biopsy is rarely performed and diagnosis is still primarily made based on the history of the symptoms and depends on a battery of neurological, psychometric and biochemical tests. These latter tests include assessment of ApoE e4 allele status and measurements of amyloid beta, tau and phospho-tau in cerebrospinal fluid.

These present methods, nevertheless, are still unsatisfactory not only for the early diagnosis of AD and other tauopathies, but also for predicting the progression of neurological disease which is important for recruitment of patients for clinical trials, for designing new therapies and for predicting the effectiveness of current and new therapies.

The ideal diagnostic biomarkers should have high specificity for disease versus non-disease and high sensitivity to distinguish between disease types and stages.

Prognostic biomarkers should reflect the intensity and severity of the pathological changes and predict their future course from a very early stage of the disease, before degeneration is observed, until advanced stages of the disease.

Pharmacodynamic biomarkers should give a reliable indication whether an administered therapy is efficacious based on the changes in the level of disease-related proteins in readily accessible body fluids such as blood, blood products including platelets, serum and most preferably plasma and CSF. It is also desirable that such pharmacodynamics biomarkers can provide guidance to clinicians when to stop treatment or switch to a different therapy.

New targets need to be efficacious, safe, meet clinical and commercial needs and, above all, be 'druggable'. A 'druggable' target is accessible to the putative drug molecule, be that a small molecule or larger biologicals and upon binding, elicit a biological response which may be measured both in vitro and in vivo. In other words, its inhibition or activation will result in a therapeutic effect in a disease state.

Hence, there remains a need for proteins that may perform with superior sensitivity and/or specificity as biomarkers in the diagnosis, staging, prognostic monitoring and assessment of the effectiveness of treatments for patients with Alzheimer's disease and other tauopathies and may serve as new targets for the development of new therapies.

SUMMARY OF THE INVENTION

The present invention, therefore, provides novel biomarkers and phosphorylated amino acids of tau or fragments thereof for use in methods for diagnosing, staging, treating and assessing the response of a treatment for a neurocognitive disorder characterised by tau toxicity such as tauopathies, in particular for Alzheimer's disease. In addition, the present invention provides novel targets for the development of new therapies against tauopathies or for repurposing existing therapies not originally designed for the treatment of neurocognitive disorders such as tauopathies.

In a first aspect the present invention provides for a panel of biomarkers comprising:
 i) protein phosphatase 1 regulatory subunit 14A comprising or having the amino acid sequence of SEQ ID NO:1 or an isoform or a variant or a fragment thereof; and/or
 ii) 2',3'-cyclic-nucleotide 3'-phosphodiesterase comprising or having the amino acid sequence of SEQ ID NO:2 or an isoform or a variant or a fragment thereof.

In a second aspect the present invention provides for a panel of biomarkers comprising tau or one or more fragments thereof, wherein tau:
 i) comprises or has the amino acid sequence of SEQ ID NO:29 and
 ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/5416 or S422;
wherein when the phosphorylated amino acid on tau is T181, the panel comprises tau or one or more fragments thereof having at least one more phosphorylated amino acid.

In a third aspect the present invention provides for a panel of biomarkers comprising one or more, optionally two or more proteins selected from Tables 5, 6, 7, 8, 9, 10, 11, 12, 13 or combinations thereof.

In one embodiment of the first aspect, the panel of biomarkers further comprises one or more, alternative two or more, proteins selected from Group A, which comprises Actin alpha cardiac muscle 1 comprising or having the amino acid sequence of SEQ ID NO:11, Antithrombin-III comprising or having the amino acid sequence of SEQ ID NO:12, BH3-interacting domain death agonist comprising or having the amino acid sequence of SEQ ID NO:3, cAMP-dependent protein kinase type I-beta regulatory subunit comprising or having the amino acid sequence of SEQ ID NO:24, Catenin delta-1 comprising or having the amino acid sequence of SEQ ID NO:4, Centrosomal protein of 170 kDa comprising or having the amino acid sequence of SEQ ID NO:23, Clathrin light chain B comprising or having the amino acid sequence of SEQ ID NO:5, Egl nine homolog 1 comprising or having the amino acid sequence of SEQ ID NO:13, Fibrinogen gamma chain comprising or having the amino acid sequence of SEQ ID NO:14, GMP reductase 1 comprising or having the amino acid sequence of SEQ ID NO:27, Guanine nucleotide-binding protein G(q) subunit alpha comprising or having the amino acid sequence of SEQ ID NO:6, Insulin-like growth factor-binding protein 6 comprising or having the amino acid sequence of SEQ ID NO:15, KxDL motif-containing protein 1 comprising or having the amino acid sequence of SEQ ID NO:28, Lambda-crystallin homolog comprising or having the amino acid sequence of SEQ ID NO:18, Myelin-associated oligodendrocyte basic protein comprising or having the amino acid sequence of SEQ ID NO:20, Neutral alpha-glucosidase AB comprising or having the amino acid sequence of SEQ ID NO:7, Nuclear pore complex protein Nup155 comprising or having the amino acid sequence of SEQ ID NO:19, OCIA domain-containing protein 1 comprising or having the amino acid sequence of SEQ ID NO:16, Protein KIAA1045 comprising or having the amino acid sequence of SEQ ID NO:25, Secernin-2 comprising or having the amino acid sequence of SEQ ID NO:8, Serum albumin comprising or having the amino acid sequence of SEQ ID NO:17, Short-chain specific acyl-CoA dehydrogenase comprising or having the amino acid sequence of SEQ ID NO:9, Synaptoporin comprising or having the amino acid sequence of SEQ ID NO:22, Syntaphilin comprising or having the amino acid sequence of SEQ ID NO:10, Transmembrane protein 119 comprising or having the amino acid sequence of SEQ ID NO: 21 and Tubulin alpha chain-like 3 comprising or having the amino acid sequence of SEQ ID NO:26.

In another embodiment, the panel of biomarkers according to the first aspect of the invention further comprises one or more proteins selected from Groups B, C or D.

In one other embodiment, the panel of biomarkers according to the first aspects and its embodiments may further comprise one or more biomarkers as defined in the second and/or third aspect of the invention.

In a fourth aspect the invention provides for a method for diagnosing a neurocognitive disorder in a subject, the method comprising:
a) assaying a sample obtained from said subject for the biomarkers of the panel as defined in any one of the first, second and third aspect of the invention, including the embodiments thereof;
b) measuring in said sample a concentration or an amount of each of the biomarkers of said panel;
c) determining whether that subject has a neurocognitive disorder by comparing said concentration or amount of each of the biomarkers of the panel in said sample with reference concentrations or amounts of said biomarkers.

In a fifth aspect the invention provides for method for staging a neurocognitive disorder in a subject, the method comprising:

a) assaying a sample obtained from said subject for the biomarkers of the panel as defined in any one of the first, second and third aspect of the invention, including the embodiments thereof;
b) measuring in said sample a concentration or an amount of each of the biomarkers of said panel;
c) determining the stage of the neurocognitive disorder in said subject by comparing said concentration or amount of each of the biomarkers of the panel in said sample with reference concentrations or amounts of said biomarkers.

In a sixth aspect the invention provides for a method for assessing in a subject the likelihood of developing a neurocognitive disorder, the method comprising:
a) assaying a sample obtained from said subject for the biomarkers of the panel as defined in any one of the first, second and third aspect of the invention, including the embodiments thereof;
b) measuring in said sample a concentration or an amount of each of the biomarkers of said panel;
c) determining whether that subject is likely to develop a neurocognitive disorder by comparing said concentration or amount of each of the biomarkers of the biomarker panel in said sample with reference concentrations or amounts of said biomarkers.

In a seventh aspect the invention provides for a method for treating a neurocognitive disorder in a subject, the method comprising:
a) assaying a sample obtained from said subject for the biomarkers of the panel as defined in any one of the first, second and third aspect of the invention, including the embodiments thereof;
b) measuring in said sample a concentration or an amount of each of the biomarkers of said panel;
c) determining whether that subject has a neurocognitive disorder by comparing said concentration or amount of each of the biomarkers in said sample with reference concentrations or amounts of said biomarkers;
d) administering to said subject a drug for treating the neurocognitive disorder.

Alternatively, the seventh aspect of the present invention may be formulated as a drug for use in the treatment of a neurocognitive disorder in a subject, wherein the subject is selected by the method comprising:
a) assaying a sample obtained from said subject for the biomarkers of the panel as defined in any one of the first, second and third aspect of the invention, including the embodiments thereof;
b) measuring in said sample a concentration or an amount of each of the biomarkers of said panel;
c) determining whether that subject has a neurocognitive disorder by comparing said concentration or amount of each of the biomarkers in said sample with reference concentrations or amounts of said biomarkers.

Alternatively, the seventh aspect of the present invention may be formulated as a use of a drug for the manufacture of a medicament for the treatment of a neurocognitive disorder in a subject, wherein the subject is selected by the method comprising:
a) assaying a sample obtained from said subject for the biomarkers of the panel as defined in any one of the first, second and third aspect of the invention, including the embodiments thereof;
b) measuring in said sample a concentration or an amount of each of the biomarkers of said panel;
c) determining whether that subject has a neurocognitive disorder by comparing said concentration or amount of each of the biomarkers in said sample with reference concentrations or amounts of said biomarkers.

In an eighth aspect the present invention provides for a method for assessing the response to a drug for treating a neurocognitive disorder in a subject, wherein the subject has been treated or is being treated with said drug, the method comprising:
a) assaying a sample obtained from a subject for the biomarkers of the panel as defined in any one of the first, second and third aspect of the invention, including the embodiments thereof;
b) measuring in said sample a concentration or an amount of each of the biomarkers of said panel;
c) determining whether that subject has responded or is responding to said drug by comparing said concentration or amount of each of the biomarkers in said sample with reference concentrations or amounts of said biomarkers.

In one embodiment of the seventh and eighth aspects of the invention, the drug for treating a neurocognitive disorder is a kinase inhibitor. Preferably, the kinase inhibitor is selected from a tau kinase inhibitor or a casein kinase inhibitor, optionally a casein kinase 1 alpha, beta, gamma, delta or epsilon. More preferably the kinase inhibitor is a casein kinase 1 delta inhibitor selected from 5-(1,3-benzoxazol-2-yl)-4-(pyridin-4-yl)pyrimidin-2-amine; 2-amino-3-[(thiophen-2-yl)carbonyl]indolizine-1-carboxamide; 2-[3-(pyridin-4-yl)-1H-pyrazol-4-yl]-1,3-benzoxazole; 2-amino-3-[(4-fluorophenyl)carbonyl]indolizine-1-carboxamide; 2-Methyl-amino-3-[(4-fluorophenyl)carbonyl]indolizine-1-carboxamide; 2-amino-3-benzoylindolizine-1-carboxamide; 2-amino-1-[(4-fluorophenyl)carbonyl]-1H-indole-3-carboxamide; combinations thereof; or pharmaceutically acceptable salt or solvate thereof. Even more preferably, the casein kinase 1 delta inhibitor is selected from 5-(1,3-benzoxazol-2-yl)-4-(pyridin-4-yl)pyrimidin-2-amine; 2-amino-3-[(4-fluorophenyl)carbonyl]indolizine-1-carboxamide; 2-Methyl-amino-3-[(4-fluorophenyl)carbonyl]indolizine-1-carboxamide.

In preferred embodiments of the fourth, fifth, sixth, seventh and eighth aspect of the invention, the neurocognitive disorder is characterised by tau toxicity. More preferably, the neurocognitive disorder is a tauopathy.

The tauopathy may be selected from the group of Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, chronic traumatic encephalopathy, alpha-synucleinopathies, Parkinson's disease or combinations thereof.

Even more preferably the tauopathy is Alzheimer's disease.

In one embodiment of the seventh aspect of the invention, step d) further comprises administering an additional therapeutic agent selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof.

In one other embodiment of the eighth aspect of the invention the subject may have also been treated or may also being treated with an additional therapeutic agent selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof.

In another embodiment of the eighth aspect, preferably or alternatively, after step c), the method comprises administering an additional therapeutic agent selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof.

In embodiments of the fourth, fifth, sixth, seventh and eighth aspect of the invention the assaying step a) and/or the measuring step b) comprise:
i) contacting said sample with one or more binding agents to each of said biomarkers of the panel; or
ii) detecting in said sample autoantibodies specific to each of said biomarkers; or
iii) detecting in said sample by mass spectrometry each of said biomarkers of the panel or fragments thereof, optionally by previously labelling said sample with one or more isobaric reactive mass labels; or
iv) detecting in said sample by 2D gel electrophoresis each of said biomarkers of the panel; or
iv) any combinations of i), ii), iii) or iv).

Preferably, the assaying in step a) and/or the measuring is step b) comprise:
i) detecting one or more fragments of said biomarkers in the panel and/or
ii) detecting one or more phosphorylated amino acids on tau comprising or having the amino acid sequence of SEQ ID NO: 29 or one or more fragments thereof; wherein when the phosphorylated amino acid on tau to be detected is T181, at least one more phosphorylated amino acid on tau or one or more fragments thereof is detected.

More preferably, the sample is immobilised on a solid support.

In embodiments of the fourth, fifth, sixth, seventh and eighth aspect of the invention the sample is selected from the group of cerebrospinal fluid (CSF), blood, plasma, serum, saliva, urine, tissue (e.g. brain tissue) or combinations thereof. Preferably the sample is CSF or blood. Also preferably, the subject is a human subject.

In a ninth aspect the present invention provides for a kit comprising reagents for assaying and/or measuring in a sample the biomarkers of a panel as defined in any one of the first, second and third aspect of the invention, including the embodiments thereof.

The reagents may comprise one or more binding agents which specifically bind to the biomarkers of the panels. Preferably, the one or more binding agents are primary antibodies, wherein each primary antibody specifically binds to:
i) a different biomarkers of the panel and/or
ii) one or more phosphorylated amino acids of tau comprising or having amino acid sequence of SEQ ID NO: 29 or fragments thereof.

The reagents may further comprise one or more secondary antibodies which specifically bind to said primary antibodies. Preferably the secondary antibodies are labelled.

In another embodiment of the ninth aspect and of its embodiments the sample is selected from the group of cerebrospinal fluid (CSF), blood, plasma, serum, saliva, urine, tissue (e.g. brain tissue) or combinations thereof.

BRIEF DESCRIPTION OF THE DRAWINGS

FIG. 1. Sequence of human protein phosphatase 1 regulatory subunit 14A (SEQ ID NO: 1). Amino acids flagged by symbol ☐ or a * indicate amino acids which are replaced by a different or a modified amino acid in an isoform or a variant of human protein phosphatase 1 regulatory subunit 14A, respectively.

FIG. 2. Sequence of human 2',3'-cyclic-nucleotide 3'-phosphodiesterase (SEQ ID NO: 2). Amino acids flagged by symbol ☐ or a * indicate amino acids which are replaced by a different or a modified amino acid in an isoform or a variant of human 2',3'-cyclic-nucleotide 3'-phosphodiesterase, respectively.

FIG. 3. Venn diagram for protein phosphatase 1 regulatory subunit 14A.

FIG. 4. Venn diagram for 2',3'-cyclic-nucleotide 3'-phosphodiesterase.

DEFINITIONS

Figure 5:
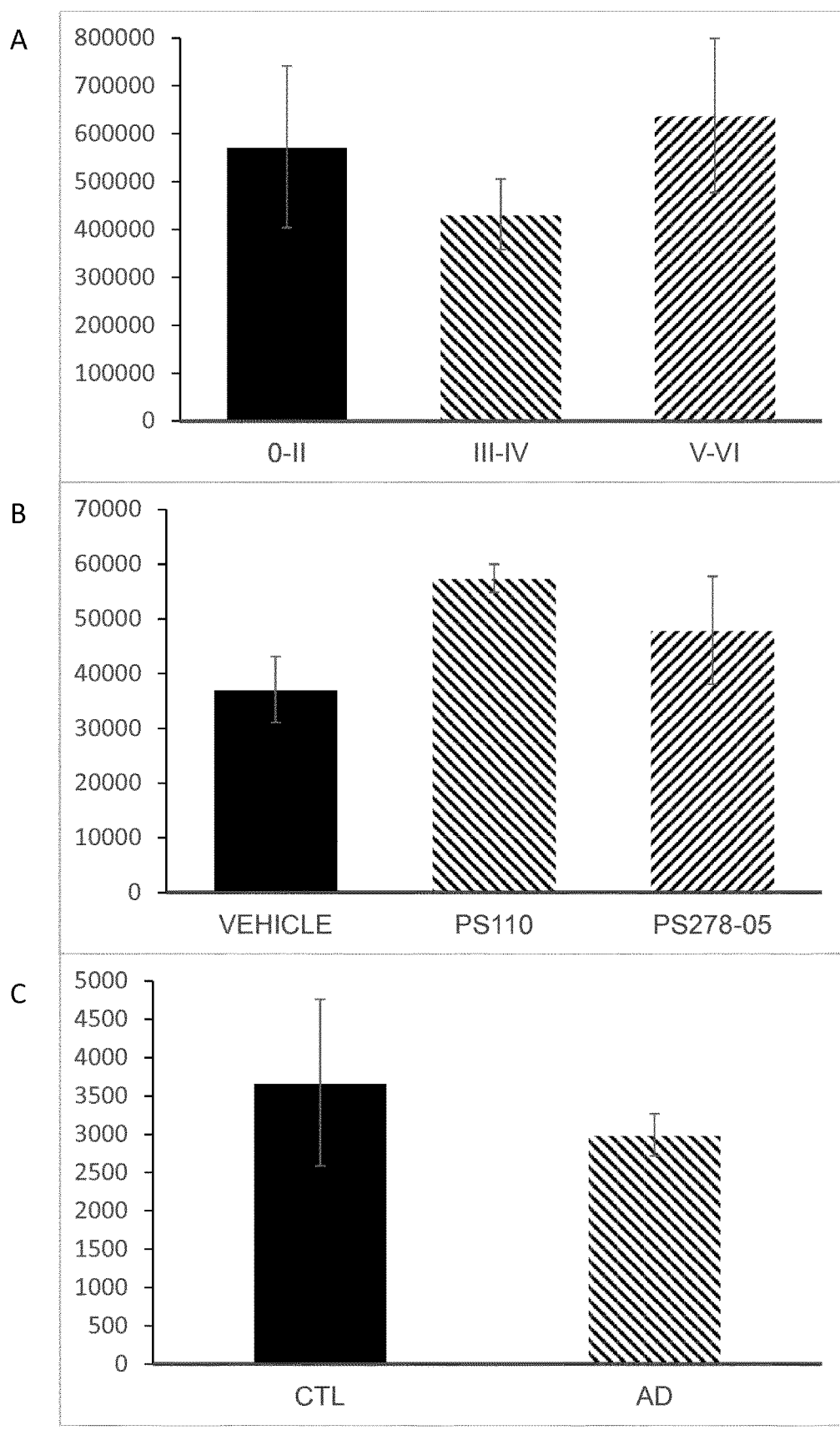
FIG. 5. Levels (as sums of ions intensities of all non-modified peptides) of protein phosphatase 1 regulatory subunit 14A in (A) Human brain with mild (Braak 0-II) (n=3), moderate (Braak III/IV) or severe (Braak v/VI) tau pathology; (B) Mouse brain from the TMHT model of human tauopathy treated orally with vehicle alone or vehicle including 30 mg/kg of casein kinase 1 delta inhibitors 5-(1,3-benzoxazol-2-yl)-4-(pyridin-4-yl)pyrimidin-2-amine (PS110) and 2-Methyl-amino-3-[(4-fluorophenyl)carbonyl]indolizine-1-carboxamide (PS278-05); and (C) CSF from cognitively affected non-AD controls (CTL; n=3) and patients with biochemically diagnosed AD (AD; n=3).

The term "biomarker(s)" includes all biologically relevant forms of the protein identified, including post-translational modifications. For example, the biomarker can be present in a glycosylated, phosphorylated, multimeric, fragmented or precursor form. A biomarker fragment may be naturally occurring or, for example, enzymatically generated and still retaining the biologically active function of the full protein. Fragments will typically be at least about 10 amino acids, usually at least about 50 amino acids in length, and can be as long as 300 amino acids in length or longer.

The term "canonical sequence" is used herein as to refer to the most prevalent sequence and/or the most similar sequence among orthologous species. In particular, unless otherwise specified, the canonical sequence refers herein to the human sequence.

The term "KEGG pathway" refers to a collection of manually drawn pathway maps representing molecular interactions and reaction networks for metabolism, genetic information processing, environmental information processing, cellular processes, organismal systems, human diseases and drug development. "KEGG pathways mapping" is the process to map molecular datasets, especially large-scale datasets in genomics, transcriptomics, proteomics, and metabolomics, to the KEGG pathway maps for biological interpretation of higher-level systemic functions; (genome.jp/kegg/pathway.html).

The term "concentration or amount" refers to the relative concentration or amount of biomarker in the sample, for example as determined by LC-MS/MS label free quantification approaches such as area under the curve and spectral counting.

The term "comparing" or "compare" or grammatical equivalents thereof, means measuring the relative concentration or amount of a biomarker in a sample relative to other samples (for example protein concentrations or amounts stored in proprietary or public database).

The term "reference concentration or amount" refers to, but it is not limited to, protein concentrations or amounts stored in proprietary or public databases. The "reference concentration or amount" may have been obtained from a large screening of patients, or by reference to a known or previously determined correlation between such a determination and clinical information in control patients. For example, the reference values may be determined by comparison to the concentration or amount of the biomarkers in a control subject, for example a healthy person (i.e. without dementia) of similar age and gender as the subject. Alternatively, the reference values are values which can be found in literature such as the ApoE ε4 allele presence whereby the presence or absence of the mutations at position 112 and 158 represent the reference to be compared to, or like the levels of total tau (T-tau)>350 ng/L, phospho-tau (P-tau)>80 ng/L and Aβ42<530 ng/L in the CSF (Hansson 0, et al., Lancet Neurol. 2006, 5(3), 228-34). In addition, the reference values may have been obtained from the same subject at one or more time points which precede in time the test time point. Such earlier sample may be taken one week or more, one month or more, three months or more, most preferably six months or more before the date of the test time point. In some embodiments, multiple earlier samples may be compared in a longitudinal manner and the slope of change in biomarker expression may be calculated as a correlate of cognitive decline.

The term "control" or as used herein "non AD control" or "non AD subject" refers to a tissue sample or a bodily fluid sample taken from a human or non-human subject that is cognitively normal or diagnosed with or presenting symptoms of a cognitive abnormality but defined, with respect to the existing biochemical tests, as non AD subjects.

The term "binding agent" generally refers to any molecule that has affinity for a biomarker of the present invention. Binding agents may comprises apatamers, antibodies, lectins and enzymes.

The term "antibody" includes polyclonal antiserum, monoclonal antibodies, fragments of antibodies such as single chain and Fab fragments, and genetically engineered antibodies. The antibodies may be chimeric or of a single species.

The term "aptamer" includes small affinity agents with selectivity for a specific target and which are polymers of nucleic acids, amino acids or other synthetic organic molecules or combinations of any of these constituent molecules.

The terms "selected reaction monitoring", "SRM" and "MRM" means a mass spectrometry assay whereby precursor ions of known mass-to-charge ratio representing known biomarkers are preferentially targeted for analysis by tandem mass spectrometry in an ion trap or triple quadrupole mass spectrometer. During the analysis the parent ion is fragmented and the number of daughter ions of a second predefined mass-to-charge ratio is counted. Typically, an equivalent precursor ion bearing a predefined number of stable isotope substitutions but otherwise chemically identical to the target ion is included in the method to act as a quantitative internal standard.

The term "immunoassay" refers to any method of quantitatively measuring the level of one or more biomarkers of the present invention by capturing and or detecting the presence of the target biomarker using one or more binding agents. Immunoassays may be direct, where the biomarker is adsorbed onto a surface and detected using a binding agent carrying a detectable label, indirect where the biomarker is adsorbed onto a surface, a first binding agent with specificity for the biomarker is then captured onto the surface through specific binding to the target biomarker and detected using a second binding agent carrying a detectable label that is specific for the first antibody. Alternatively the immunoassay may be a sandwich immunoassay in which a binding agent is immobilised on a solid support and captures the target biomarker from the analytical sample. Subsequently, the now immobilised biomarker is detected using binding agents in the direct or indirect methods as described above.

The term "bead suspension array" means an immunoassay where the biomarker is detected on one or mall solid particles held in a liquid suspension.

The term "planar array" means an immunoassay system where individual biomarkers or binding agents are immobilised in discrete addressable locations on a continuous solid surface including but not limited to glass slide, silicon wafer, nitrocellulose strip. Subsequent steps of an immunoassay are then performed using common reagents applied to the entire surface of the planar array or may be added individually at the appropriate addressable location within the array.

The term "isolated", or grammatical equivalents thereof, means throughout this specification, that the protein, antibody, polynucleotide or chemical molecule as the case may be, exists in a physical milieu distinct from that in which it may occur in nature.

As used herein, the term "subject" includes any human or non-human animal. The term "non-human animal" includes all vertebrates, e.g., mammals and non-mammals, such as non-human primates, rodents, sheep, dogs, cats, horses, cows, chickens, amphibians, reptiles, etc.

The term "treat", "treating", "treatment", "prevent", "preventing" or "prevention", or grammatical equivalents thereof, includes therapeutic treatments, prophylactic treatments and applications in which one reduces the risk that a subject will develop a disorder or other risk factor. Treatment does not require the complete curing of a disorder and encompasses the reduction of the symptoms or underlying risk factors.

The term "diagnosis", or grammatical equivalents thereof, as used herein, includes the provision of any information concerning the existence or presence, non-existence or absence or probability of the disorder in a patient. It further includes the provision of information concerning the type or classification of the disorder or of symptoms which are or may be experienced in connection with it. This may include, for example, diagnosis of the severity of the disorder. It encompasses prognosis of the medical course of the disorder, for example its duration, severity and the course of progression from mild cognitive impairment (MCI) to AD or other dementias.

The term "staging", or grammatical equivalents thereof, as used herein, means identifying in a subject the stage of a neurocognitive disorder, in particular AD. For example, AD is characterised by 3 stage or 7 stages, depending on the diagnostic framework used. The Global Dementia Scale is one such measure of global function. It is measured by assessment of severity including cognition and function against a standardised set of severity criteria.

The term "efficacy" indicates the capacity for beneficial change of a given intervention (e.g. a drug, medical device, surgical procedure, etc.). If efficacy is established, that intervention is likely to be at least as good as other available interventions, to which it will have been compared. The term "efficacy" and "effectiveness" are used herein interchangeably.

The term "comprising" indicates that the subject includes all the elements listed, but may, optionally, also include additional, unnamed elements (i.e. open).

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless the context dictates otherwise, the definitions of the features/terms set out above are not limited to any particular aspect or embodiment of the invention and apply equally to all aspects and embodiments which are described herein.

Abbreviations

CSF (cerebrospinal fluid); LBD (Lewy body dementia); FTD (fronto-temporal dementia); VaD (vascular dementia); ALS (amyotrophic lateral sclerosis) CJD (Creutzfeldt-Jakob disease); CNS (central nervous system); TMT® (Tandem Mass Tag®); TEAB (Tetra-ethylamonium Bicarbonate); TFA (Trifluoroacetic acid); SDS (Sodium dodecyl sulfate); TCEP (Tris(2-carboxyethyl)phosphine); ACN (Acetonitrile); Da (Dalton); HPLC (High-performance liquid chromatography); FA (Formic acid); IFC (Intelligent flow control); LC-MS/MS (Liquid Chromatography with tandem Mass Spectrometry detection); MS (Mass Spectrometry); MS/MS or MS2 (Tandem MS); MS/MS/MS or MS3 (triple MS) PAGE (Polyacrylamide gel electrophoresis); SCX (Strong Cation Exchange); ppm (Parts per million); $TiO_2$ (titanium dioxide); IMAC (iron metal affinity chromatography); ELISA (enzyme-linked immonusorbent assay).

DETAILED DESCRIPTION

1. Proteins Panels and Methods of Using Thereof

Whilst it is widely accepted that tau is involved in the pathology of neurodegenerative disorders such as tauopathies, like AD, and that it actively participates in the formation of neurofibrillary tangles, not much is known about the molecular processes that mediate toxicity of over expressed and hyperphosphorylated tau.

The present inventors hypothesized that tau over expression and hyperphosphorylation causes tau toxicity in the brain leading to further events, including activation of signalling pathways, which may contribute to the advancement and severity of the disease. They further hypothesised that many of the proteins involved in these pathways would be released into blood and CSF during the evolution of tau toxicity and would be detectable early in the disease process.

The present inventors have surprisingly found that multiple cellular processes, the associated proteins and/or their levels are modified in a tau dose-dependent manner and that these affected pathways are correlated with several hallmarks of AD.

Furthermore, the panel of biomarkers identified herein are not exclusively expressed in the brain, they are surprisingly also identifiable in the cerebrospinal fluid (CSF) and most importantly their abundance in CSF is regulated between non-AD and AD patients with substantive memory effects.

Finally, the present inventors successfully demonstrated herein that upon administration of tau kinase inhibitors (enzymes which inhibits tau phosphorylation), the abundance of the proteins (i.e. biomarkers) of the panels according to the present invention increases or decreases inversely to their pre-administration abundance, indicating that the inhibitors are effective in reducing hyperphosphorylation of tau. Most surprisingly, as the abundance of these proteins increases or decreases inversely to their pre-administration abundance, also the tau toxicity comparably decreases.

The present invention provides for a panel of biomarkers comprising:
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform or a variant or a fragment thereof.

Protein phosphatase 1 regulatory subunit 14A is an inhibitor of PPP1CA (serine/threonine-protein phosphatase PP1-alpha catalytic subunit). Has over 1000-fold higher inhibitory activity when phosphorylated, creating a molecular switch for regulating the phosphorylation status of PPP1CA substrates and smooth muscle contraction.

Described to participate in RNA metabolism in the myelinating cell, 2',3'-cyclic-nucleotide 3'-phosphodiesterase is the third most abundant protein in central nervous system myelin. Its catalytic activity is on nucleoside 2',3'-cyclic phosphate which is transformed into nucleoside 2'-phosphate.

An isoform is described herein as an alternative protein sequence with respect to the canonical sequence. Isoforms can be generated from the same gene by a single or by the combination of alternative promoter usage, alternative splicing, alternative initiation and ribosomal frameshifting.

A variant is described herein as to include natural variants such as (naturally occurring) polymorphisms, variations between strains, isolates or cultivars, disease-associated mutations and RNA editing events. A variant is generally reported as the amino acid change with respect to the canonical sequence. Most naturally occurring polymorphisms (also called single amino acid polymorphisms or SAPs) are due to a single nucleotide change at the codon level. RNA editing events include conversion, insertion and deletion of nucleotides.

A fragment is described herein as the result of proteolytic (enzymatic or else) cleavage of a protein. Fragments may be the results of natural proteolytic cleavage for example fragments generated during the activation of complement, the clotting cascade, or from enzymatic cleavage of matrix proteins. Alternatively, fragments may be generated in-vivo and/or in-vitro for example with proteases.

In one embodiment, the variant of protein phosphatase 1 regulatory subunit 14A comprises or has the amino acid sequence of SEQ ID NO: 1 and wherein
  a) serine at position 26 is replaced by phosphoserine; or
  b) threonine at position 38 is replaced by phosphothreonine; or
  c) serine at position 136 is replaced by phosphoserine; or
  d) glycine at position 123 is replaced by arginine.

FIG. 1 shows the human sequence of protein phosphatase 1 regulatory subunit 14A (SEQ ID NO:1); flagged by symbol □ are those amino acids that are replaced with a different amino acid in isoforms of human protein phosphatase 1 regulatory subunit 14A as indicated above in d). Amino acids flagged by a * are those amino acids which are replaced by modified amino acids in isoforms of human protein phosphatase 1 regulatory subunit 14A as indicated above in a) to c).

In another embodiment the isoform of protein phosphatase 1 regulatory subunit 14A comprises or has the amino acid sequence of SEQ ID NO:1 wherein amino acid 68 to 94 are missing (isoform 2).

In another embodiment, the variant of 2',3'-cyclic-nucleotide 3'-phosphodiesterase comprises or has the amino acid sequence of SEQ ID NO: 2 and wherein
  a) tyrosine at position 110 is replaced by phosphotyrosine; or
  b) cysteine at position 418 is replaced by cysteine methyl ester; or
  c) cysteine at position 418 is replaced by S-farnesyl cysteine; or
  d) glutamine at position 207 is replaced by arginine.

FIG. 2 shows the human sequence of 2',3'-cyclic-nucleotide 3'-phosphodiesterase (SEQ ID NO:2); flagged by symbol □ are those amino acids that are replaced with a different amino acid in isoforms of human 2',3'-cyclic-nucleotide 3'-phosphodiesterase as indicated above in d). Amino acids flagged by a * are those amino acids which are replaced by modified amino acids in isoforms of human protein phosphatase 1 regulatory subunit 14A as indicated above in a) to c).

In another embodiment the isoform of 2',3'-cyclic-nucleotide 3'-phosphodiesterase comprises or has the amino acid sequence of SEQ ID NO:2 wherein amino acid 1 to 20 are missing (isoform CNPI).

In general clinical practice, proteins for use as biomarkers are measured as a set of at least 2, preferably at least 3 or 4. Hence, in addition to protein phosphatase 1 regulatory subunit 14A comprising or having the amino acid sequence of SEQ ID NO:1 or an isoform or a variant or a fragment thereof and/or 2',3'-cyclic-nucleotide 3'-phosphodiesterase comprising or having the amino acid sequence of SEQ ID NO:2 or an isoform or a variant or a fragment thereof, the panel of biomarkers according to the present invention may further comprise one or more, alternative two or more, preferably more than two proteins selected from Group A which comprises Actin alpha cardiac muscle 1 comprising or having the amino acid sequence of SEQ ID NO:11, Anti-thrombin-III comprising or having the amino acid sequence of SEQ ID NO:12, BH3-interacting domain death agonist comprising or having the amino acid sequence of SEQ ID NO:3, cAMP-dependent protein kinase type I-beta regulatory subunit comprising or having the amino acid sequence of SEQ ID NO:24, Catenin delta-1 comprising or having the amino acid sequence of SEQ ID NO:4, Centrosomal protein of 170 kDa comprising or having the amino acid sequence of SEQ ID NO:23, Clathrin light chain B comprising or having the amino acid sequence of SEQ ID NO:5, Egl nine homolog 1 comprising or having the amino acid sequence of SEQ ID NO:13, Fibrinogen gamma chain comprising or having the amino acid sequence of SEQ ID NO:14, GMP reductase 1 comprising or having the amino acid sequence of SEQ ID NO:27, Guanine nucleotide-binding protein G(q) subunit alpha comprising or having the amino acid sequence of SEQ ID NO:6, Insulin-like growth factor-binding protein 6 comprising or having the amino acid sequence of SEQ ID NO:15, KxDL motif-containing protein 1 comprising or having the amino acid sequence of SEQ ID NO:28, Lambda-crystallin homolog comprising or having the amino acid sequence of SEQ ID NO:18, Myelin-associated oligodendrocyte basic protein comprising or having the amino acid sequence of SEQ ID NO:20, Neutral alpha-glucosidase AB comprising or having the amino acid sequence of SEQ ID NO:7, Nuclear pore complex protein Nup155 comprising or having the amino acid sequence of SEQ ID NO:19, OCIA domain-containing protein 1 comprising or having the amino acid sequence of SEQ ID NO:16, Protein KIAA1045 comprising or having the amino acid sequence of SEQ ID NO:25, Secernin-2 comprising or having the amino acid sequence of SEQ ID NO:8, Serum albumin comprising or having the amino acid sequence of SEQ ID NO:17, Short-chain specific acyl-CoA dehydrogenase comprising or having the amino acid sequence of SEQ ID NO:9, Synaptoporin comprising or having the amino acid sequence of SEQ ID NO:22, Syntaphilin comprising or having the amino acid sequence of SEQ ID NO:10, Transmembrane protein 119 comprising or having the amino acid sequence of SEQ ID NO: 21 and Tubulin alpha chain-like 3 comprising or having the amino acid sequence of SEQ ID NO:26.

Table 1 shows the names of the biomarkers of "Group A" and their Uniprot codes for the human protein and its mouse counterpart.

TABLE 1

Biomarkers of Group A

| SEQ ID NO: | Protein Name | UNIPROT ID (human) | UNIPROT ID (mouse) |
|---|---|---|---|
| 1 | phosphatase 1 regulatory subunit 14A | Q96A00 | Q91VC7 |
| 2 | 2',3'-cyclic-nucleotide 3'-phosphodiesterase | P09543 | P16330 |
| 3 | BH3-interacting domain death agonist | P55957 | P70444 |
| 4 | Catenin delta-1 | O60716 | P30999 |
| 5 | Clathrin light chain B | P09497 | Q61RU5 |
| 6 | Guanine nucleotide-binding protein G(q) subunit alpha | P50148 | P21279 |
| 7 | Neutral alpha-glucosidase AB | Q14697 | Q8BHN3 |
| 8 | Secernin-2 | Q96FV2 | Q8VCA8 |
| 9 | Short-chain specific acyl-CoA dehydrogenase, mitochondrial | P16219 | Q07417 |
| 10 | Syntaphilin | O15079 | Q80U23 |
| 11 | Actin, alpha cardiac muscle 1 | P68032 | P68033 |
| 12 | Antithrombin-III | P01008 | P32261 |
| 13 | Egl nine homolog 1 | Q9GZT9 | Q91YE3 |
| 14 | Fibrinogen gamma chain | P02679 | Q8VCM7 |
| 15 | Insulin-like growth factor-binding protein | P24592 | P47880 |
| 16 | OCIA domain-containing protein 1 | Q9NX40 | Q9CRD0 |
| 17 | Serum albumin | P02768 | P07724 |
| 18 | Lambda-crystallin homolog | Q9Y2S2 | Q99KP3 |
| 19 | Nuclear pore complex protein Nup155 | O75694 | Q99P88 |
| 20 | Myelin-associated oligodendrocyte basic protein | Q13875 | Q9D2P8 |
| 21 | Transmembrane protein 119 | Q4V9L6 | Q8R138 |
| 22 | Synaptoporin | Q8TBG9 | Q8BGN8 |
| 23 | Centrosomal protein of 170 kDa | Q5SW79 | H7BX26 |
| 24 | cAMP-dependent protein kinase type 1 | P31321 | P12849 |
| 25 | Protein KIAA1045 | Q9UPV7 | Q80TL4 |
| 26 | Tubulin alpha chain-like 3 | A6NHL2 | Q3UX10 |
| 27 | GMP reductase 1 | P36959 | Q9DCZ1 |
| 28 | KxDL motif-containing protein 1 | Q9BQD3 | Q80XH1 |

In one embodiment, the panel of biomarkers according to the present invention comprises i) protein phosphatase 1 regulatory subunit 14A comprising or having the amino acid sequence of SEQ ID NO:1 or an isoform or a variant or a fragment thereof; and/or ii) 2',3'-cyclic-nucleotide 3'-phosphodiesterase comprising or having the amino acid sequence of SEQ ID NO:2 or an isoform or a variant or a fragment thereof and one or more, preferably two or more, biomarkers selected from "Group B", which comprises Actin alpha cardiac muscle 1 comprising or having the amino acid sequence of SEQ ID NO:11, Antithrombin-III comprising or having the amino acid sequence of SEQ ID NO:12, BH3-interacting domain death agonist comprising or having the amino acid sequence of SEQ ID NO:3, Catenin delta-1 comprising or having the amino acid sequence of SEQ ID NO:4, Clathrin light chain B comprising or having the amino acid sequence of SEQ ID NO:5, Egl nine homolog 1 comprising or having the amino acid sequence of SEQ ID NO:13, Fibrinogen gamma chain comprising or having the amino acid sequence of SEQ ID NO:14, Guanine nucleotide-binding protein G(q) subunit alpha comprising or having the amino acid sequence of SEQ ID NO:6, Insulin-like growth factor-binding protein 6 comprising or having the amino acid sequence of SEQ ID NO:15, Lambda-crystallin homolog comprising or having the amino acid sequence of SEQ ID NO:18, Neutral alpha-glucosidase AB comprising or having the amino acid sequence of SEQ ID NO:7, Nuclear pore complex protein Nup155 comprising or having the amino acid sequence of SEQ ID NO:19, OCIA domain-containing protein 1 comprising or having the amino acid sequence of SEQ ID NO:16, Secernin-2 comprising or having the amino acid sequence of SEQ ID NO:8, Serum albumin comprising or having the amino acid sequence of SEQ ID NO:17, Short-chain specific acyl-CoA dehydrogenase comprising or having the amino acid sequence of SEQ ID NO:9 and Syntaphilin comprising or having the amino acid sequence of SEQ ID NO:10.

This sub-group of biomarkers (referred herein as "Group B") have been identified in separate in human plasma or human serum of non-AD individuals (http://www.plasmaproteomedatabase.org/). Hence, it is to be expected that these biomarkers will be not only present in blood/blood products in AD patients but also that their up/down-regulation observed in CSF will translate in the blood/blood products. This is particularly advantageous as blood and its products (plasma or serum) are more readily and easily accessible for diagnosis than CSF.

In another embodiment, the panel of biomarkers comprises i) protein phosphatase 1 regulatory subunit 14A comprising or having the amino acid sequence of SEQ ID NO:1 or an isoform or a variant or a fragment thereof; and/or ii) 2',3'-cyclic-nucleotide 3'-phosphodiesterase comprising or having the amino acid sequence of SEQ ID NO:2 or an isoform or a variant or a fragment thereof and one or more, preferably two or more, biomarkers selected from "Group C", which comprises Actin alpha cardiac muscle 1 comprising or having the amino acid sequence of SEQ ID NO:11, Antithrombin-III comprising or having the amino acid sequence of SEQ ID NO:12, BH3-interacting domain death agonist comprising or having the amino acid sequence of SEQ ID NO:3, cAMP-dependent protein kinase type I-beta regulatory subunit comprising or having the amino acid sequence of SEQ ID NO:24, Catenin delta-1 comprising or having the amino acid sequence of SEQ ID NO:4, Centrosomal protein of 170 kDa comprising or having the amino acid sequence of SEQ ID NO:23, Clathrin light chain B comprising or having the amino acid sequence of SEQ ID NO:5, Egl nine homolog 1 comprising or having the amino acid sequence of SEQ ID NO:13, Fibrinogen gamma chain comprising or having the amino acid sequence of SEQ ID NO:14, GMP reductase 1 comprising or having the amino acid sequence of SEQ ID NO:27, Guanine nucleotide-binding protein G(q) subunit alpha comprising or having the amino acid sequence of SEQ ID NO:6, Insulin-like growth factor-binding protein 6 comprising or having the amino acid sequence of SEQ ID NO:15, Lambda-crystallin homolog comprising or having the amino acid sequence of SEQ ID NO:18, Myelin-associated oligodendrocyte basic protein comprising or having the amino acid sequence of SEQ ID NO:20, Neutral alpha-glucosidase AB comprising or having the amino acid sequence of SEQ ID NO:7, Nuclear pore complex protein Nup155 comprising or having the amino acid sequence of SEQ ID NO:19, OCIA domain-containing protein 1 comprising or having the amino acid sequence of SEQ ID NO:16, Protein KIAA1045 comprising or having the amino acid sequence of SEQ ID NO:25, Serum albumin comprising or having the amino acid sequence of SEQ ID NO:17, Short-chain specific acyl-CoA dehydrogenase comprising or having the amino acid sequence of SEQ ID NO:9, Synaptoporin comprising or having the amino acid sequence of SEQ ID NO:22, Syntaphilin comprising or having the amino acid sequence of SEQ ID NO:10 and Tubulin alpha chain-like 3 comprising or having the amino acid sequence of SEQ ID NO:26.

This sub-group of biomarkers (which will be referred herein as "Group C") has been found to be regulated in human CSF of AD patients versus control subjects and inversely regulated in mouse brain upon administration of a casein kinase inhibitors.

TABLE 2

Biomarkers of "Group C".

| SEQ ID NO: | UNIPROT ID | Protein Name | Human CSF AD/cntrl Log 2 Braak stage 3/4 | Human CSF AD/cntrl Log 2 Braak stage 5/6 | Mouse brain Log 2 Ck1 inhibitor PS110 | Mouse brain Log 2 Ck1 inhibitor PS278 |
|---|---|---|---|---|---|---|
| 1 | Q96A00 | phosphatase 1 regulatory subunit 14A | 0.79 | 0.69 | 0.71 | 0.49 |
| 2 | P09543 | 2',3'-cyclic-nucleotide 3'-phosphodiesterase | 0.57 | 0.57 | 0.63 | 0.62 |
| 3 | P55957 | BH3-interacting domain death agonist | 0.80 | — | −0.53 | −0.56 |
| 4 | O60716 | Catenin delta-1 | — | 0.58 | −2.26 | −1.07 |
| 5 | P09497 | Clathrin light chain B | 0.90 | — | 0.70 | 0.50 |
| 6 | P50148 | Guanine nucleotide-binding protein G(q) subunit alpha | 0.59 | — | 0.82 | 0.62 |
| 7 | Q14697 | Neutral alpha-glucosidase AB | 0.72 | 0.59 | 0.52 | −0.78 |
| 9 | P16219 | Short-chain specific acyl-CoA dehydrogenase, mitochondrial | −0.75 | — | 0.54 | 0.57 |
| 10 | O15079 | Syntaphilin | — | 0.52 | −0.71 | −0.76 |
| 11 | P68032 | Actin, alpha cardiac muscle 1 | 0.56 | — | 0.58 | — |
| 12 | P01008 | Antithrombin-III | −0.59 | — | 0.57 | — |
| 13 | Q9GZT9 | Egl nine homolog 1 | 0.77 | — | — | −073 |
| 14 | P02679 | Fibrinogen gamma chain | −0.79 | — | 1.01 | — |
| 15 | P24592 | Insulin-like growth factor-binding protein | 0.86 | — | −0.53 | — |
| 16 | Q9NX40 | OCIA domain-containing protein 1 | 0.77 | 0.94 | — | −0.59 |
| 17 | P02768 | Serum albumin | −0.63 | — | 0.69 | — |
| 18 | Q9Y2S2 | Lambda-crystallin homolog | 0.60 | — | — | 0.56 |
| 19 | O75694 | Nuclear pore complex protein Nup155 | 0.49 | — | −0.53 | — |
| 20 | Q13875 | Myelin-associated oligodendrocyte basic protein | 0.60 | — | 0.84 | 0.66 |
| 22 | Q8TBG9 | Synaptoporin | 0.91 | 1.03 | — | 0.72 |
| 23 | Q5SW79 | Centrosomal protein of 170 kDa | 0.91 | 0.92 | — | −0.51 |
| 24 | P31321 | cAMP-dependent protein kinase type 1 | 1.56 | — | 0.53 | — |
| 25 | Q9UPV7 | Protein KIAA1045 | 0.67 | — | −0.63 | — |
| 26 | A6NHL2 | Tubulin alpha chain-like 3 | 1.75 | — | — | 0.67 |
| 27 | P36959 | GMP reductase 1 | 1.30 | — | 0.68 | — |

In another embodiment the panel of biomarkers according to the present invention comprises i) protein phosphatase 1 regulatory subunit 14A comprising or having the amino acid sequence of SEQ ID NO:1 or an isoform or a variant or a fragment thereof; and/or ii) 2',3'-cyclic-nucleotide 3'-phosphodiesterase comprising or having the amino acid sequence of SEQ ID NO:2 or an isoform or a variant or a fragment thereof and one or more, preferably two or more, biomarkers selected from "Group D", which comprises Secernin-2 comprising or having the amino acid sequence of SEQ ID NO:8, Transmembrane protein 119 comprising or having the amino acid sequence of SEQ ID NO: 21 KxDL motif-containing protein 1 comprising or having the amino acid sequence of SEQ ID NO:28.

This sub-group of biomarkers (which will be referred herein as "Group D") has been found to be regulated in the brain of AD patients versus control and regulated in mouse brain upon administration of casein kinase inhibitors.

TABLE 3

Biomarkers of "Group D".

| SEQ ID NO: | UNIPROT ID | Protein Name | Human brain AD/cntrl Log 2 | Mouse brain Log 2 Ck1 inhibitor | |
|---|---|---|---|---|---|
| | | | | PS110 | PS278 |
| 1 | Q96A00 | phosphatase 1 regulatory subunit 14A | 0.79 | 0.69 | 0.71 |
| 2 | P09543 | 2',3'-cyclic-nucleotide 3'-phosphodiesterase | 0.57 | 0.57 | 0.63 |
| 8 | Q96FV2 | Secernin-2 | 0.56 | −0.76 | −0.52 |
| 21 | Q4V9L6 | Transmembrane protein 119 | 1.15 | −0.66 | −0.52 |
| 28 | Q9BQD3 | KxDL motif-containing protein 1 | 0.58 | −0.58 | — |

Groups C and D (listed in Tables 2 and 3, respectively) comprise biomarkers which have been shown to be regulated in mouse brain following administration of two different casein kinase inhibitors and i) (Table 2; Group C) biomarkers which are up or down-regulated in the CSF of human patient with AD at Braak stages 3/4 or 5/6 or ii) (Table 3; Group D) biomarkers which are up/down-regulated in human brain of AD patients versus control subjects. These biomarkers are very advantageous as they allow to diagnose and stage the tauopathy but also serve as pharmacodynamics biomarkers allowing to establish if a treatment is effective in that specific patient or if an alternative approach should be followed.

Furthermore, the present invention provides for a panel of biomarkers comprising tau or one or more fragments thereof, wherein tau:
i) comprises or has the amino acid sequence of SEQ ID NO:29 and
ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422;

wherein when the phosphorylated amino acid on tau is T181, the panel comprises tau or one or more fragments thereof having at least one more phosphorylated amino acid.

The microtubule-associated protein tau becomes abnormally phosphorylated in the hippocampus and cortex of patients with Alzheimer's disease, ultimately forming aggregates which organise into paired helical filaments (PHF tau), a pathological hallmark of the condition. Certain phosphorylated forms of tau protein can propagate through the brain by trans-synaptic spreading and presumably through this and other poorly understood processes is also found in cerebrospinal fluid. The ratio of tau phosphorylated at serine 181 (based on 2N4R tau isoform sequence; SEQ ID NO: 29) relative to total tau within the CSF is an accepted biomarker used to classify individuals as having pre-symptomatic Alzheimer's disease and to confirm the clinical diagnosis in symptomatic disease.

The amino acids phosphorylated on tau having or comprising the amino acid sequence of SEQ ID NO: 29 or fragments thereof identified in the present inventions are serine and/or threonine and/or tyrosine amino acids as illustrated in Table 4.

TABLE 4

Amino acids of tau protein (SEQ ID NO: 29) found to be phosphorylated in tau from human CSF and/or human brain and/or mouse brain (X means detected)

| Amino acid Number | Mouse Brain | Human Brain | Human CSF |
|---|---|---|---|
| T39 | X | | |
| S46 | X | X | X |
| T50 | X | X | |
| T52 | X | | |
| T56 | X | X | |
| S61 | X | X | X |
| T63 | X | | |
| S64 | X | | X |
| S68 | X | | |
| T69 | X | | |
| S113 | X | | |
| T181 | X | X | X |
| S184 | X | X | X |
| S185 | X | X | X |
| S191 | X | X | |
| S195 | X | | |
| S198 | X | X | X |
| S199 | X | X | X |
| S202 | X | X | X |
| S205 | X | X | X |
| S208 | X | X | X |
| S210 | X | X | |
| T212 | X | X | X |
| S214 | X | X | X |
| T217 | X | X | X |
| T231 | X | X | X |
| S235 | | X | X |
| S237 | | X | X |
| S238 | | X | X |
| S258 | | X | X |
| S262 | X | X | X |
| S285 | | | X |
| S289 | | X | X |
| S356 | X | X | X |
| Y394 | X | X | |
| S396 | X | X | X |
| S400 | X | X | X |
| T403 | X | X | X |
| S404 | | X | X |
| S409 | X | X | |
| S412 | X | | |
| S413 | X | | |
| T414/S416 | X | | |
| S422 | | | X |

Each of the amino acid shown in Table 4 have diagnostic, prognostic and/or pharmacodynamic biomarker utility. Preferably the seventeen phosphorylated residues that were detected in all studies (X in all columns) have greatest potential as pharmacodynamics biomarkers as they are present during human disease, are also detected in an animal model treated with a casein kinase inhibitor, and could also be detected in CSF of humans.

More preferably, the panel of biomarkers comprising tau or one or more fragments thereof, wherein tau:
i) comprises or has the amino acid sequence of SEQ ID NO:29 and
ii) comprises phosphorylated amino acids S61, S64, T181, S184, S202, S205, T231 and/or S235.

In one embodiment, the panel of biomarkers comprising tau or one or more fragments thereof, wherein tau:
i) comprises or has the amino acid sequence of SEQ ID NO:29 and
ii) comprises one or more, optionally two or more phosphorylated amino acids selected from S61, S64, S199, S205, and S396.

In another embodiment, the panel of biomarkers comprising tau or one or more fragments thereof, wherein tau:
i) comprises or has the amino acid sequence of SEQ ID NO:29 and
ii) comprises phosphorylated amino acid S61.

In another embodiment, the panel of biomarkers comprising tau or one or more fragments thereof, wherein tau:
i) comprises or has the amino acid sequence of SEQ ID NO:29 and
ii) comprises phosphorylated amino acid S64.

In another embodiment, the panel of biomarkers comprising tau or one or more fragments thereof, wherein tau:
i) comprises or has the amino acid sequence of SEQ ID NO:29 and
ii) comprises phosphorylated amino acid S199.

In another embodiment, the panel of biomarkers comprising tau or one or more fragments thereof, wherein tau:
i) comprises or has the amino acid sequence of SEQ ID NO:29 and
ii) comprises phosphorylated amino acid S205.

In another embodiment, the panel of biomarkers comprising tau or one or more fragments thereof, wherein tau:
i) comprises or has the amino acid sequence of SEQ ID NO:29 and
ii) comprises phosphorylated amino acid S396.

In another embodiment, the panel of biomarkers comprising tau or one or more fragments thereof, wherein tau:
i) comprises or has the amino acid sequence of SEQ ID NO:29 and
ii) comprises phosphorylated amino acids S61 and S64.

In another embodiment, the panel of biomarkers comprising tau or one or more fragments thereof, wherein tau:
i) comprises or has the amino acid sequence of SEQ ID NO:29 and
ii) comprises phosphorylated amino acids S61 and S199.

In another embodiment, the panel of biomarkers comprising tau or one or more fragments thereof, wherein tau:
i) comprises or has the amino acid sequence of SEQ ID NO:29 and
ii) comprises phosphorylated amino acids S61 and S205.

In another embodiment, the panel of biomarkers comprising tau or one or more fragments thereof, wherein tau:
i) comprises or has the amino acid sequence of SEQ ID NO:29 and
ii) comprises phosphorylated amino acids S61 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S64 and S199.

In another embodiment, the panel of biomarkers comprising tau or one or more fragments thereof, wherein tau:
i) comprises or has the amino acid sequence of SEQ ID NO:29 and
ii) comprises phosphorylated amino acids S64 and S205.

In another embodiment, the panel of biomarkers comprising tau or one or more fragments thereof, wherein tau:
i) comprises or has the amino acid sequence of SEQ ID NO:29 and
ii) comprises phosphorylated amino acids S64 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S199 and S205.

In another embodiment, the panel of biomarkers comprising tau or one or more fragments thereof, wherein tau:
i) comprises or has the amino acid sequence of SEQ ID NO:29 and
ii) comprises phosphorylated amino acids S199 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S205 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S64 and S199.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S64 and S205.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S64 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S199 and S205.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S199 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S205 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S64, S199 and S205.

In another embodiment, the panel of biomarkers comprising tau or one or more fragments thereof, wherein tau:
i) comprises or has the amino acid sequence of SEQ ID NO:29 and ii) comprises phosphorylated amino acids S64, S199 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S64, S205 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S199, S205 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S64, S199 and S205.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S64, S199 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S199, S205 and S396.

In another embodiment, the panel of biomarkers comprising tau or one or more fragments thereof, wherein tau:
i) comprises or has the amino acid sequence of SEQ ID NO:29 and
ii) comprises phosphorylated amino acids S61, S64, S199, S205, and S396.

The embodiments relating to the amino acid sequence and the particular phosphorylated amino acids in tau or on one or more fragments thereof, as described above, are equally applicable to all other embodiments of the second aspect of the invention and to all other aspects of the invention where tau or on one or more fragments thereof is involved.

In one embodiment, the panel of biomarker comprises at least one biomarker selected from Groups A, B, C or D and one biomarker selected from tau or one or more fragments thereof, wherein tau:
i) comprises or has the amino acid sequence of SEQ ID NO:29 and
ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422;
wherein when the phosphorylated amino acid on tau is T181, the panel comprises tau or one or more fragments thereof having at least one more phosphorylated amino acid. Preferably, the biomarker selected from Groups A, B, C or D is:
i) protein phosphatase 1 regulatory subunit 14A comprising or having the amino acid sequence of SEQ ID NO:1 or an isoform or a variant or a fragment thereof; or ii) 2',3'-cyclic-nucleotide 3'-phosphodiesterase comprising or having the amino acid sequence of SEQ ID NO:2 or an isoform or a variant or a fragment thereof.

More preferably, the panel comprises three or more, four or more, five or more biomarkers, wherein at least two biomarkers, in addition to tau, are selected from Groups A, B, C or D and are:
i) protein phosphatase 1 regulatory subunit 14A comprising or having the amino acid sequence of SEQ ID NO:1 or an isoform or a variant or a fragment thereof; and
ii) 2',3'-cyclic-nucleotide 3'-phosphodiesterase comprising or having the amino acid sequence of SEQ ID NO:2 or an isoform or a variant or a fragment thereof.

Additionally, the present invention provides for a panel of biomarkers comprising one or more, optionally two or more proteins selected from Tables 5, 6, 7, 8, 9, 10, 11, 12, 13 or combinations thereof.

These biomarkers have been found to be highly regulated in the CSF of AD patients versus control. All non-modified peptides for each protein were summed for three control and three AD cases. The log 2 ratio and p-value of each protein was then calculated. Proteins with 2 or more peptides, >60% regulation and p<0.05 were selected as biomarkers for Table 5.

TABLE 5

Biomarkers up/down-regulated in the CSF of AD patient versus control

| UniProtKB Accession Number | Protein name | Log2 AD/Control | P value |
|---|---|---|---|
| I3L192 | Basigin | −3.86 | 0.04 |
| E5RJZ1 | Cytochrome c oxidase subunit 7A-related protein, mitochondrial | 4.19 | 0.05 |
| K7EIT4 | 14-3-3 protein epsilon | 0.78 | 0.04 |
| K7EJ68 | 3-ketoacyl-CoA thiolase, mitochondrial | 0.91 | 0.01 |
| B4DVF4 | 3-ketoacyl-CoA thiolase, peroxisomal | 1.28 | 0.02 |
| P25325 | 3-mercaptopyruvate sulfurtransferase | 0.81 | 0.01 |
| P08708 | 40S ribosomal protein S17 | 1.34 | 0.01 |
| E5RIP1 | 40S ribosomal protein S20 | 1.32 | 0.01 |
| D6R9I7 | 40S ribosomal protein S23 | 0.83 | 0.04 |
| P61247 | 40S ribosomal protein S3a | 0.96 | 0.04 |
| F5GZI0 | 4F2 cell-surface antigen heavy chain | 1.29 | 0.03 |
| P32754 | 4-hydroxyphenylpyruvate dioxygenase | 0.76 | 0.03 |
| F8VPE8 | 60S acidic ribosomal protein P0 | 0.73 | 0.03 |
| H7C3M2 | 60S ribosomal protein L3 | 2.45 | 0.01 |
| C9JIJ5 | 60S ribosomal protein L7 | 0.86 | <0.01 |
| Q8IZP0 | Abl interactor 1 | 1.04 | 0.01 |
| H0YN26 | Acidic leucine-rich nuclear phosphoprotein 32 family member A | 1.76 | 0.04 |
| E9PF58 | Actin-related protein 2/3 complex subunit 1A | 0.94 | 0.02 |
| B4DXW1 | Actin-related protein 3 | 0.73 | 0.04 |
| I3L1U8 | Active breakpoint cluster region-related protein | 0.92 | <0.01 |
| O14561 | Acyl carrier protein, mitochondrial | 0.72 | 0.02 |
| P07108 | Acyl-CoA-binding protein | 1.18 | 0.02 |
| O14734 | Acyl-coenzyme A thioesterase 8 | 0.76 | <0.01 |
| E9PQQ8 | Adenylate kinase isoenzyme 5 | 0.89 | 0.02 |
| P12235 | ADP/ATP translocase 1 | 0.71 | 0.03 |
| F5H1V1 | ADP-ribosylation factor 3 | 0.74 | 0.03 |
| Q9NVJ2 | ADP-ribosylation factor-like protein 8B | 0.94 | 0.01 |
| H0Y5U1 | Agrin | 1.05 | 0.03 |
| P11766 | Alcohol dehydrogenase class-3 | 0.87 | 0.05 |
| A6NHU4 | Aldo-keto reductase family 1 member C1 | −1.04 | 0.01 |
| P55008 | Allograft inflammatory factor 1 | 0.82 | 0.03 |
| P02763 | Alpha-1-acid glycoprotein 1 | −1.03 | 0.02 |

TABLE 5-continued

Biomarkers up/down-regulated in the CSF of AD patient versus control

| UniProtKB Accession Number | Protein name | Log2 AD/Control | P value |
|---|---|---|---|
| G3V3A0 | Alpha-1-antichymotrypsin | −0.84 | 0.04 |
| H0YJ11 | Alpha-actinin-1 | 0.67 | 0.01 |
| M0R2M1 | Alpha-soluble NSF attachment protein | 0.74 | 0.03 |
| P05067 | Amyloid beta A4 protein | 0.90 | <0.01 |
| K7EMN4 | Amyloid-like protein 1 | 0.73 | 0.01 |
| E9PQS3 | Amyloid-like protein 2 | 0.94 | 0.01 |
| P03950 | Angiogenin | −0.76 | 0.03 |
| E7EV01 | Ankyrin repeat and SOCS box protein 2 | 1.68 | 0.01 |
| P16157 | Ankyrin-1 | 0.86 | 0.01 |
| D6R9U4 | Ankyrin-2 | 0.65 | 0.03 |
| V9GYC1 | Apolipoprotein A-II | −0.85 | <0.01 |
| P06727 | Apolipoprotein A-IV | −1.97 | 0.04 |
| P04114 | Apolipoprotein B-100 | 0.70 | 0.04 |
| B0YIW2 | Apolipoprotein C-III | −0.77 | 0.04 |
| G3V1B6 | Apolipoprotein O | 0.84 | 0.03 |
| H0YER7 | Apoptosis inhibitor 5 | 0.79 | 0.04 |
| E9PMA0 | Apoptosis-inducing factor 1, mitochondrial | 0.69 | 0.03 |
| P29972 | Aquaporin-1 | 0.90 | <0.01 |
| B0YIW6 | Archain 1 | −1.26 | 0.01 |
| F8VXI9 | ARF GTPase-activating protein GIT2 | 1.10 | 0.02 |
| Q96P47 | Arf-GAP with GTPase, ANK repeat and PH domain-containing protein 3 | 0.66 | 0.01 |
| O43776 | Asparagine--tRNA ligase, cytoplasmic | 1.37 | 0.03 |
| P17174 | Aspartate aminotransferase, cytoplasmic | 0.99 | 0.03 |
| B1AJS1 | Astrotactin-1 | 0.70 | 0.01 |
| K7EJP1 | ATP synthase subunit alpha, mitochondrial | 0.77 | 0.04 |
| C9JU26 | ATP synthase subunit f, mitochondrial | 0.75 | 0.03 |
| P17858 | ATP-dependent 6-phosphofructokinase, liver type | 0.68 | 0.02 |
| Q96BJ3 | Axin interactor, dorsalization-associated protein | 0.98 | 0.04 |
| Q4VXN1 | Band 4.1-like protein 1 | 1.36 | 0.01 |
| E9PQD2 | Band 4.1-like protein 2 | 3.48 | 0.02 |
| P02749 | Beta-2-glycoprotein 1 | −0.70 | 0.00 |
| Q562R1 | Beta-actin-like protein 2 | 0.77 | 0.05 |
| P35612 | Beta-adducin | 0.77 | 0.05 |
| Q96KN2 | Beta-Ala-His dipeptidase | 0.71 | 0.05 |
| P07686 | Beta-hexosaminidase subunit beta | 1.49 | 0.00 |
| C9JSN9 | Biotinidase | 0.97 | 0.01 |
| Q9NZE6 | Eukaryotic translation initiation factor 4A, isoform 2, isoform CRA_b | 0.75 | 0.01 |
| Q8WXS3 | Brain and acute leukemia cytoplasmic protein | 0.88 | 0.05 |
| P11274 | Breakpoint cluster region protein | 0.99 | 0.01 |
| Q96GW7 | Brevican core protein | 0.69 | 0.03 |
| Q9HCU4 | Cadherin EGF LAG seven-pass G-type receptor 2 | 0.68 | <0.01 |
| P19022 | Cadherin-2 | 1.17 | 0.05 |
| Q9UQM7 | Calcium/calmodulin-dependent protein kinase type II subunit alpha | 0.81 | 0.02 |
| E7ETC9 | Calcium/calmodulin-dependent protein kinase type II subunit beta | 1.08 | <0.01 |
| Q16566 | Calcium/calmodulin-dependent protein kinase type IV | 0.85 | 0.03 |
| H7C4P2 | Calcium-dependent secretion activator 1 | 0.87 | 0.03 |
| F8WBR5 | Calmodulin | 1.09 | 0.03 |
| Q9P1Y5 | Calmodulin-regulated spectrin-associated protein 3 | 0.91 | 0.01 |
| P07384 | Calpain-1 catalytic subunit | 1.06 | 0.03 |
| O94985 | Calsyntenin-1 | 0.75 | 0.01 |
| Q9BQT9 | Calsyntenin-3 | 0.76 | 0.01 |
| O43852 | Calumenin | 1.15 | 0.01 |
| C9J9E2 | CaM kinase-like vesicle-associated protein | 0.70 | 0.05 |
| K7EM13 | cAMP-dependent protein kinase type I-alpha regulatory subunit | 0.97 | <0.01 |
| P31321 | cAMP-dependent protein kinase type I-beta regulatory subunit | 1.56 | 0.04 |
| Q5TDF0 | Cancer-related nucleoside-triphosphatase | 0.93 | 0.01 |
| Q8WXD9 | Caskin-1 | 0.76 | 0.04 |
| Q92851 | Caspase-10 | 1.21 | 0.01 |
| Q86VU5 | Catechol O-methyltransferase domain-containing protein 1 | 1.06 | 0.01 |
| C9IZ88 | Catenin alpha-2 | 2.11 | 0.01 |
| E9PKT6 | Cathepsin H | 0.73 | 0.01 |
| E9PNW4 | CD59 glycoprotein | 0.79 | 0.04 |
| Q5JYX0 | Cell division control protein 42 homolog | 1.04 | 0.05 |
| Q99674 | Cell growth regulator with EF hand domain protein 1 | 0.86 | <0.01 |
| Q5SW79 | Centrosomal protein of 170 kDa | 0.92 | 0.02 |
| Q8NI60 | Chaperone activity of bc1 complex-like, mitochondrial | 0.78 | 0.01 |
| Q7LBR1 | Charged multivesicular body protein 1b | 0.66 | 0.01 |
| Q96FZ7 | Charged multivesicular body protein 6 | 0.83 | <0.01 |
| Q9BWS9 | Chitinase domain-containing protein 1 | 0.85 | 0.02 |
| J3KS05 | Chromobox protein homolog 1 | 0.84 | 0.01 |
| G5E968 | Chromogranin A, isoform CRA_b | 0.78 | 0.01 |
| Q9UPT6 | C-Jun-amino-terminal kinase-interacting protein 3 | −0.85 | 0.01 |
| Q8IZR5 | CKLF-like MARVEL transmembrane domain-containing protein 4 | 0.70 | 0.01 |
| E5RGY9 | Clathrin coat assembly protein AP180 | 1.45 | 0.02 |
| D6RJD1 | Clathrin light chain B | 0.84 | 0.02 |
| Q14019 | Coactosin-like protein | 0.68 | 0.02 |
| P00740 | Coagulation factor IX | −0.73 | 0.05 |
| P53618 | Coatomer subunit beta | 1.07 | 0.03 |
| H0Y8X7 | Coatomer subunit gamma-1 | 0.69 | 0.03 |
| I3L0M4 | Coiled-coil domain-containing protein 43 | 0.99 | 0.01 |
| Q96A33 | Coiled-coil domain-containing protein 47 | 0.79 | 0.02 |
| H7C5H1 | Complement factor B | −1.11 | 0.03 |
| Q03591 | Complement factor H-related protein 1 | −0.67 | <0.01 |
| V9GYE7 | Complement factor H-related protein 2 | −1.01 | 0.01 |
| E9PDN6 | Contactin-associated protein-like 4 | 0.85 | 0.01 |
| H0YKU5 | COP9 signalosome complex subunit 2 | 1.31 | 0.01 |
| Q92905 | COP9 signalosome complex subunit 5 | 0.76 | 0.01 |
| O75367 | Core histone macro-H2A.1 | 0.67 | 0.01 |
| H0YJG0 | Creatine kinase B-type | 0.68 | 0.03 |
| E7EPF8 | C-terminal-binding protein 1 | 0.84 | 0.01 |
| E9PC62 | CUGBP Elav-like family member 2 | 0.99 | 0.01 |
| F5H6I6 | Cullin-associated NEDD8-dissociated protein 1 | 1.06 | 0.04 |
| E9PHZ2 | Cysteine and histidine-rich domain-containing protein 1 | 0.67 | 0.02 |
| Q16878 | Cysteine dioxygenase type 1 | 1.32 | 0.05 |
| H0YFA4 | Cysteine-rich protein 2 | 0.95 | 0.03 |
| H3BP04 | Cytochrome b-c1 complex subunit 2, mitochondrial | 0.67 | 0.02 |
| P14927 | Cytochrome b-c1 complex subunit 7 | 0.98 | 0.05 |
| P47985 | Cytochrome b-c1 complex subunit Rieske, mitochondrial | 1.13 | 0.04 |
| Q5JTJ3 | Cytochrome c oxidase assembly factor 6 homolog | 1.23 | 0.01 |
| K7EQD3 | Cytochrome c oxidase subunit 6B1 | 0.88 | 0.02 |
| Q99418 | Cytohesin-2 | 0.77 | 0.03 |
| E7EPF5 | Cytoplasmic protein NCK2 | 0.72 | 0.02 |
| C9JM78 | D-beta-hydroxybutyrate dehydrogenase, mitochondrial | 1.46 | 0.00 |
| Q9UKG1 | DCC-interacting protein 13-alpha | 0.79 | 0.01 |
| H7C342 | D-dopachrome decarboxylase | 0.88 | 0.03 |
| Q8NFT8 | Delta and Notch-like epidermal growth factor-related receptor | 1.02 | 0.01 |
| Q08495 | Dematin | 0.76 | 0.01 |
| P60981 | Destrin | 0.93 | 0.05 |
| Q9BPU6 | Dihydropyrimidinase-related protein 5 | 0.82 | 0.03 |

TABLE 5-continued

Biomarkers up/down-regulated in the CSF of AD patient versus control

| UniProtKB Accession Number | Protein name | Log2 AD/Control | P value |
|---|---|---|---|
| E7EPF1 | Disintegrin and metalloproteinase domain-containing protein 22 | 1.05 | 0.01 |
| B4E2H8 | Disks large homolog 1 | 1.37 | 0.03 |
| A8MVA8 | Disks large homolog 2 | 0.72 | 0.02 |
| O00273 | DNA fragmentation factor subunit alpha | −0.67 | 0.03 |
| O75190 | DnaJ homolog subfamily B member 6 | 1.27 | <0.01 |
| Q9NVH1 | DnaJ homolog subfamily C member 11 | 0.94 | 0.01 |
| Q13217 | DnaJ homolog subfamily C member 3 | 0.86 | <0.01 |
| K7EIH8 | DnaJ homolog subfamily C member 7 | 0.92 | 0.02 |
| B7Z4L4 | Dolichyl-diphosphooligosaccharide--protein glycosyltransferase subunit 1 | 1.87 | 0.01 |
| Q9P0K9 | DOMON domain-containing protein FRRS1L | 1.48 | 0.01 |
| F8VYL3 | Dynamin-1-like protein | 0.89 | 0.01 |
| P50570 | Dynamin-2 | 0.89 | 0.03 |
| Q9P225 | Dynein heavy chain 2, axonemal | 1.15 | 0.00 |
| H3BS86 | E3 ubiquitin-protein ligase CHIP | 0.83 | 0.01 |
| Q05639 | Elongation factor 1-alpha 2 | 0.68 | 0.04 |
| H3BNU3 | Elongation factor Tu, mitochondrial | 1.14 | 0.01 |
| Q9NZ08 | Endoplasmic reticulum aminopeptidase 1 | 1.16 | <0.01 |
| H0YIV0 | Endoplasmin | 1.18 | 0.04 |
| B1AKC9 | Ephrin type-B receptor 2 | 1.26 | 0.02 |
| P20827 | Ephrin-A1 | 0.86 | 0.05 |
| Q92506 | Estradiol 17-beta-dehydrogenase 8 | 0.87 | 0.04 |
| Q92731 | Estrogen receptor beta | 1.73 | 0.01 |
| E7EMV8 | Eukaryotic initiation factor 4A-II | −0.98 | 0.03 |
| A6NJH9 | Eukaryotic translation initiation factor 1A, Y-chromosomal | 0.91 | 0.03 |
| O75821 | Eukaryotic translation initiation factor 3 subunit G | 1.02 | 0.04 |
| O43909 | Exostosin-like 3 | 1.03 | <0.01 |
| I3L252 | FAD-AMP lyase | 3.43 | 0.02 |
| H3BRW3 | FAD-linked sulfhydryl oxidase ALR | 1.50 | 0.01 |
| C9JPH9 | Fascin | 0.86 | 0.01 |
| G3V1D1 | Ferritin | 1.37 | 0.03 |
| Q6MZW2 | Follistatin-related protein 4 | 1.38 | <0.01 |
| H3BR68 | Fructose-bisphosphate aldolase A | 0.93 | <0.01 |
| H6UMI1 | Gamma-aminobutyric acid receptor-associated protein | 1.40 | 0.01 |
| H0YJU6 | Gamma-aminobutyric acid receptor subunit beta-3 | 0.78 | 0.01 |
| E5RGR6 | GDNF family receptor alpha-2 | 1.06 | <0.01 |
| G3V582 | Gephyrin | 1.07 | <0.01 |
| K7EMP8 | Glial fibrillary acidic protein | 0.66 | 0.03 |
| Q8TDQ7 | Glucosamine-6-phosphate isomerase 2 | −0.65 | 0.04 |
| K7EJ70 | Glucosidase 2 subunit beta | 0.80 | <0.01 |
| P42261 | Glutamate receptor 1 | 1.13 | 0.04 |
| G3V164 | Glutamate receptor 4 | 1.02 | 0.01 |
| F5H4N6 | Glutamate receptor-interacting protein 1 | −0.87 | <0.01 |
| H7BZD1 | Glutaminase kidney isoform, mitochondrial | 0.79 | 0.03 |
| O76003 | Glutaredoxin-3 | 0.90 | 0.04 |
| P07203 | Glutathione peroxidase 1 | 1.13 | 0.02 |
| Q03013 | Glutathione S-transferase Mu 4 | 1.09 | 0.04 |
| P78417 | Glutathione S-transferase omega-1 | 1.13 | 0.01 |
| H0YMX4 | Glycine amidinotransferase, mitochondrial | 1.67 | 0.04 |
| P23434 | Glycine cleavage system H protein, mitochondrial | 0.94 | 0.01 |
| H7C024 | Glypican-1 | 1.05 | <0.01 |
| Q9NZH0 | G-protein coupled receptor family C group 5 member B | 0.97 | 0.03 |
| P01112 | GTPase HRas | 1.09 | 0.01 |
| Q9Y2T3 | Guanine deaminase | 0.75 | 0.01 |
| B1AM21 | Guanine nucleotide-binding protein G(q) subunit alpha | 0.76 | 0.04 |
| P63092 | Guanine nucleotide-binding protein G(s) subunit alpha isoforms short | 1.00 | 0.03 |
| B7Z685 | Guanylate cyclase 1, soluble, beta 3, isoform CRA_c | −0.64 | 0.02 |
| B1ANH6 | Guanylate kinase | 0.69 | 0.01 |
| P00738 | Haptoglobin | −1.07 | <0.01 |
| P00739 | Haptoglobin-related protein | −1.65 | <0.01 |
| Q6PIK3 | HCG1995540, isoform CRA_b | 0.65 | 0.03 |
| D6RG00 | HCG2018358, isoform CRA_d | 0.75 | <0.01 |
| H3BQZ7 | HCG2044799 | 0.69 | 0.01 |
| K7ENF6 | Heat shock 70 kDa protein 12A | 0.86 | 0.04 |
| P08107 | Heat shock 70 kDa protein 1A/1B | 0.70 | 0.03 |
| R4GN69 | Heat shock protein 105 kDa | −0.83 | 0.01 |
| C9J3N8 | Heat shock protein beta-1 | −0.91 | 0.01 |
| Q5H962 | HECT, UBA and WWE domain containing 1 | 1.00 | 0.05 |
| Q15477 | Helicase SKI2W | 0.86 | 0.04 |
| F5GWX2 | Heme-binding protein 1 | 1.24 | <0.01 |
| P02100 | Hemoglobin subunit epsilon | 1.50 | 0.01 |
| Q6ZVN8 | Hemojuvelin | 0.87 | <0.01 |
| Q8IZP7 | Heparan-sulfate 6-O-sulfotransferase 3 | 0.78 | 0.01 |
| P05546 | Heparin cofactor 2 | −0.66 | 0.03 |
| Q9Y3E1 | Hepatoma-derived growth factor-related protein 3 | −0.67 | 0.04 |
| Q13151 | Heterogeneous nuclear ribonucleoprotein A0 | 0.90 | 0.03 |
| H0YB39 | Heterogeneous nuclear ribonucleoprotein H | 0.80 | 0.02 |
| M0QYQ7 | Heterogeneous nuclear ribonucleoprotein M | 0.67 | 0.02 |
| B1AR61 | Hexokinase-1 | 0.83 | 0.02 |
| D6RD60 | Histidine triad nucleotide-binding protein 1 | 1.01 | 0.03 |
| P16403 | Histone H1.2 | 1.33 | 0.05 |
| D6RCF2 | Histone H2A | 0.83 | 0.01 |
| U3KQK0 | Histone H2B | 0.73 | 0.03 |
| B4DEB1 | Histone H3 | 1.31 | 0.03 |
| Q6NXT2 | Histone H3.3C | 1.27 | 0.04 |
| Q16775 | Hydroxyacylglutathione hydrolase, mitochondrial | 0.85 | 0.04 |
| Q9Y4L1 | Hypoxia up-regulated protein 1 | 0.86 | 0.02 |
| P22304 | Iduronate 2-sulfatase | 1.30 | 0.03 |
| A6NGN9 | IgLON family member 5 | 1.24 | <0.01 |
| H0Y4R1 | Inosine-5'-monophosphate dehydrogenase 2 | 0.83 | 0.04 |
| H0YB38 | Inositol monophosphatase 3 | 1.12 | 0.04 |
| Q9UMF0 | Intercellular adhesion molecule 5 | 0.80 | 0.01 |
| K7EKJ9 | Interleukin enhancer-binding factor 3 | 1.57 | 0.04 |
| C9J826 | Junction plakoglobin | 2.03 | 0.04 |
| P13645 | Keratin, type I cytoskeletal 10 | 0.66 | 0.02 |
| O43790 | Keratin, type II cuticular Hb6 | 0.66 | 0.02 |
| E9PES4 | Kinesin-like protein KIF3A | 0.67 | 0.05 |
| P01042 | Kininogen-1 | −0.67 | 0.02 |
| Q04760 | Lactoylglutathione lyase | 0.71 | 0.04 |
| E9PLW6 | L-aminoadipate-semialdehyde dehydrogenase-phosphopantetheinyl transferase | −1.29 | <0.01 |
| E5RH50 | La-related protein 1 | 0.66 | <0.01 |
| F6S6P2 | Large proline-rich protein BAG6 | 0.89 | 0.03 |
| Q15334 | Lethal(2) giant larvae protein homolog 1 | 0.74 | 0.04 |
| Q9UIC8 | Leucine carboxyl methyltransferase 1 | 1.10 | <0.01 |
| H0YMX3 | Leucine-rich repeat and immunoglobulin-like domain-containing nogo receptor-interacting protein 1 | 1.28 | <0.01 |
| Q6F5E8 | Leucine-rich repeat-containing protein 16C | −1.05 | 0.02 |
| M0R2G0 | Leucine-rich repeat-containing protein 4B | 0.76 | <0.01 |
| G3V1D4 | Lin-7 homolog C (C. elegans), isoform CRA_b | 0.72 | 0.05 |
| Q5VVL7 | Lipoamide acyltransferase component of branched-chain alpha-keto acid dehydrogenase complex, mitochondrial | 0.84 | 0.03 |

TABLE 5-continued

Biomarkers up/down-regulated in the CSF of AD patient versus control

| UniProtKB Accession Number | Protein name | Log2 AD/Control | P value |
|---|---|---|---|
| C9JXK9 | Lipoma-preferred partner | 1.08 | 0.01 |
| E9PJZ7 | Liprin-alpha-1 | 1.21 | 0.03 |
| Q13136 | Liprin-alpha-1 | 0.85 | 0.01 |
| G3V200 | Liprin-alpha-2 | 1.52 | 0.04 |
| A8MW50 | L-lactate dehydrogenase | 0.72 | 0.02 |
| F5GZQ4 | L-lactate dehydrogenase A chain | 0.68 | <0.01 |
| O95573 | Long-chain-fatty-acid--CoA ligase 3 | 0.82 | 0.01 |
| P10619 | Lysosomal protective protein | 0.70 | 0.02 |
| F8VV32 | Lysozyme C | −0.99 | 0.02 |
| Q9NZW5 | MAGUK p55 subfamily member 6 | 0.72 | 0.02 |
| A2A2V1 | Major prion protein | 1.20 | <0.01 |
| C9JF79 | Malate dehydrogenase | 1.07 | 0.04 |
| F5GX14 | Malectin | 0.75 | 0.02 |
| P49006 | MARCKS-related protein | 0.95 | 0.03 |
| B3KM87 | Matrin-3 | 0.70 | 0.02 |
| Q8N3F0 | Maturin | 0.89 | 0.02 |
| Q5HYI7 | Metaxin-3 | 1.07 | <0.01 |
| F8VSC4 | Methionine aminopeptidase 2 | 0.65 | 0.01 |
| Q13825 | Methylglutaconyl-CoA hydratase, mitochondrial | 1.50 | 0.03 |
| D6RCL2 | Microtubule-associated protein 1B | 0.73 | 0.04 |
| M0QXQ9 | Microtubule-associated protein 1S | 0.76 | 0.02 |
| Q9H936 | Mitochondrial glutamate carrier 1 | 0.66 | <0.01 |
| G3V502 | Mitochondrial import inner membrane translocase subunit Tim9 | 0.92 | 0.03 |
| E5RJK1 | Mitochondrial peptide methionine sulfoxide reductase | 0.87 | <0.01 |
| Q10713 | Mitochondrial-processing peptidase subunit alpha | 0.70 | 0.04 |
| D6RAU3 | Mitogen-activated protein kinase 10 | 0.65 | 0.04 |
| Q15746 | Myosin light chain kinase, smooth muscle | 1.08 | 0.01 |
| E7ERA5 | Myosin-10 | 0.77 | 0.02 |
| P58546 | Myotrophin | 0.79 | 0.04 |
| O95865 | N(G),N(G)-dimethylarginine dimethylaminohydrolase 2 | 0.83 | 0.01 |
| O14745 | Na(+)/H(+) exchange regulatory cofactor NHE-RF1 | 1.06 | 0.05 |
| Q4G0N4 | NAD kinase 2, mitochondrial | 0.96 | <0.01 |
| D6RAI5 | NAD(P) transhydrogenase, mitochondrial | 0.86 | <0.01 |
| F8VRD8 | NADH dehydrogenase [ubiquinone] 1 alpha subcomplex subunit 12 | 1.00 | 0.05 |
| O95182 | NADH dehydrogenase [ubiquinone] 1 alpha subcomplex subunit 7 | 0.73 | 0.02 |
| Q16795 | NADH dehydrogenase [ubiquinone] 1 alpha subcomplex subunit 9, mitochondrial | 0.74 | 0.04 |
| E9PQ68 | NADH dehydrogenase [ubiquinone] 1 beta subcomplex subunit 8, mitochondrial | −0.85 | <0.01 |
| E7EPT4 | NADH dehydrogenase [ubiquinone] flavoprotein 2, mitochondrial | 0.92 | 0.05 |
| P56181 | NADH dehydrogenase [ubiquinone] flavoprotein 3, mitochondrial | 0.70 | 0.03 |
| Q9UHQ9 | NADH-cytochrome b5 reductase 1 | 0.72 | 0.02 |
| Q9BXJ9 | N-alpha-acetyltransferase 15, NatA auxiliary subunit | 0.95 | 0.04 |
| Q8TBC4 | NEDD8-activating enzyme E1 catalytic subunit | 0.82 | 0.01 |
| Q59FP8 | Neogenin | 0.98 | 0.04 |
| O00533 | Neural cell adhesion molecule L1-like protein | 0.80 | <0.01 |
| E7EQN4 | Neurexin-1-beta | 0.99 | <0.01 |
| H7C2R8 | Neurexin-2 | 1.11 | <0.01 |
| Q9Y4C0 | Neurexin-3 | 0.93 | <0.01 |
| Q9HDB5 | Neurexin-3-beta | 0.98 | <0.01 |
| Q9NPD7 | Neuritin | 0.94 | 0.03 |
| P61601 | Neurocalcin-delta | 1.33 | 0.03 |
| Q9UBB6 | Neurochondrin | 0.80 | 0.02 |
| P16519 | Neuroendocrine convertase 2 | 1.52 | <0.01 |
| Q8NFZ4 | Neuroligin-2 | 0.96 | 0.04 |
| O95502 | Neuronal pentraxin receptor | 1.09 | <0.01 |
| P47972 | Neuronal pentraxin-2 | 1.02 | 0.01 |
| O15240 | Neurosecretory protein VGF | 1.12 | <0.01 |
| C9JQU8 | Neuroserpin | 0.71 | 0.03 |
| F5H810 | Noelin | 0.90 | <0.01 |
| H7C367 | Non-POU domain-containing octamer-binding protein | 1.02 | 0.03 |
| E9PLD1 | Non-specific lipid-transfer protein | 1.54 | 0.02 |
| H0YFY6 | Nuclear mitotic apparatus protein 1 | 1.10 | 0.02 |
| Q02818 | Nucleobindin-1 | 0.87 | 0.02 |
| Q86U38 | Nucleolar protein 9 | 0.86 | 0.03 |
| E5RHP0 | Nucleoside diphosphate kinase A | 0.84 | 0.05 |
| F8W543 | Nucleosome assembly protein 1-like 1 | 0.75 | 0.02 |
| P23515 | Oligodendrocyte-myelin glycoprotein | 0.80 | <0.01 |
| X6RKL2 | Optineurin | 0.81 | <0.01 |
| D6R9C5 | Osteopontin | 0.75 | 0.04 |
| Q9BZF1 | Oxysterol-binding protein-related protein 8 | 0.78 | 0.04 |
| Q96HC4 | PDZ and LIM domain protein 5 | 0.75 | 0.02 |
| Q9UBV8 | Peflin | 0.98 | 0.03 |
| Q02790 | Peptidyl-prolyl cis-trans isomerase FKBP4 | 0.73 | 0.04 |
| O14936 | Peripheral plasma membrane protein CASK | 1.07 | 0.04 |
| H7C5W5 | Peripherin | 1.14 | 0.04 |
| P32119 | Peroxiredoxin-2 | 0.96 | 0.03 |
| I3L0T4 | Peroxisomal acyl-coenzyme A oxidase 1 | 1.02 | 0.01 |
| Q9Y285 | Phenylalanine--tRNA ligase alpha subunit | 0.72 | 0.02 |
| F8VVM2 | Phosphate carrier protein, mitochondrial | 0.78 | 0.01 |
| A8MYT4 | Phosphatidylinositol 3-kinase | 0.83 | 0.03 |
| A8MTF1 | Phosphatidylinositol 4-kinase alpha | 0.71 | 0.01 |
| P15259 | Phosphoglycerate mutase 2 | 1.12 | 0.04 |
| A6NDG6 | Phosphoglycolate phosphatase | 1.05 | 0.03 |
| M0QZI4 | Phospholipase D3 | 0.83 | 0.01 |
| P36969 | Phospholipid hydroperoxide glutathione peroxidase, mitochondrial | 0.75 | 0.02 |
| Q9H008 | Phospholysine phosphohistidine inorganic pyrophosphate phosphatase | 0.74 | 0.03 |
| Q5SRE7 | Phytanoyl-CoA dioxygenase domain-containing protein 1 | 0.65 | 0.01 |
| Q9GZP4 | PITH domain-containing protein 1 | 0.71 | 0.04 |
| Q504U3 | PKM2 protein | 0.73 | 0.02 |
| I3L495 | Platelet-activating factor acetylhydrolase IB subunit alpha | 0.97 | 0.02 |
| Q09470 | Potassium voltage-gated channel subfamily A member 1 | 0.73 | 0.04 |
| Q9UHV9 | Prefoldin subunit 2 | 0.72 | 0.04 |
| F8W8W4 | Prenylcysteine oxidase 1 | 0.74 | <0.01 |
| Q8TBB6 | Probable cationic amino acid transporter | 0.66 | 0.05 |
| P01303 | Pro-neuropeptide Y | 0.86 | 0.04 |
| Q9H7Z7 | Prostaglandin E synthase 2 | 0.98 | <0.02 |
| Q16186 | Proteasomal ubiquitin receptor ADRM1 | 1.29 | 0.05 |
| F5GX11 | Proteasome subunit alpha type-1 | 0.84 | 0.03 |
| P28066 | Proteasome subunit alpha type-5 | 1.08 | 0.03 |
| H0Y586 | Proteasome subunit alpha type-7 | 0.78 | 0.03 |
| P02760 | Protein AMBP | −0.95 | 0.04 |
| O60678 | Protein arginine N-methyltransferase 3 | 1.27 | 0.01 |
| Q5TA58 | Protein argonaute | −0.78 | 0.03 |
| E9PGA6 | Protein C1QTNF3-AMACR | 0.76 | 0.01 |
| D6RAV0 | Protein CDV3 homolog | 0.69 | 0.02 |
| B4DFG0 | Protein DEK | 0.84 | 0.01 |
| I3L3P5 | Protein disulfide-isomerase | 0.86 | 0.01 |
| Q92520 | Protein FAM3C | 0.68 | 0.03 |
| Q13045 | Protein flightless-1 homolog | 0.65 | <0.01 |
| Q02156 | Protein kinase C epsilon type | 0.99 | 0.02 |
| Q99435 | Protein kinase C-binding protein NELL2 | 0.68 | <0.01 |
| Q5SYT8 | Protein NAMPTL | 0.83 | 0.03 |

TABLE 5-continued

Biomarkers up/down-regulated in the CSF of AD patient versus control

| UniProtKB Accession Number | Protein name | Log2 AD/Control | P value |
|---|---|---|---|
| G3V2S0 | Protein NDRG2 | 0.94 | 0.01 |
| Q9BPW8 | Protein NipSnap homolog 1 | 0.80 | 0.04 |
| O75323 | Protein NipSnap homolog 2 | 1.61 | 0.02 |
| Q9UFN0 | Protein NipSnap homolog 3A | 0.73 | 0.04 |
| G3V3Z8 | Protein numb homolog | 0.66 | 0.01 |
| Q96A00 | Protein phosphatase 1 regulatory subunit 14A | 0.70 | 0.05 |
| Q9ULR3 | Protein phosphatase 1H | 0.85 | 0.01 |
| Q9Y570 | Protein phosphatase methylesterase 1 | 1.08 | 0.03 |
| Q9Y6V0 | Protein piccolo | 0.93 | 0.04 |
| E9PDC2 | Protein prune homolog 2 | 1.12 | 0.03 |
| K7EIR2 | Protein QIL1 | −0.74 | 0.03 |
| P60903 | Protein S100-A10 | 0.75 | 0.02 |
| A8MRB1 | Protein S100-B | 1.05 | 0.02 |
| H0Y8W8 | Protein transport protein Sec31A | 1.21 | <0.01 |
| H7BY58 | Protein-L-isoaspartate O-methyltransferase | 1.04 | 0.01 |
| Q5VT82 | Protocadherin 9 | 1.02 | <0.01 |
| Q9P2E7 | Protocadherin-10 | 0.78 | 0.01 |
| A6NEC2 | Puromycin-sensitive aminopeptidase-like protein | 0.69 | 0.04 |
| P0C7P4 | Putative cytochrome b-c1 complex subunit Rieske-like protein 1 | 1.07 | 0.03 |
| Q5VTE0 | Putative elongation factor 1-alpha-like 3 | 1.30 | 0.05 |
| A8MUU1 | Putative fatty acid-binding protein 5-like protein 3 | 0.80 | 0.02 |
| Q6DN03 | Putative histone H2B type 2-C | 1.09 | 0.02 |
| Q6GMV3 | Putative peptidyl-tRNA hydrolase | 0.67 | 0.01 |
| Q9H853 | Putative tubulin-like protein alpha-4B | 0.69 | 0.04 |
| Q9NVS9 | Pyridoxine-5′-phosphate oxidase | 0.81 | 0.01 |
| H3BTN5 | Pyruvate kinase | 0.71 | 0.03 |
| E9PNP4 | Radixin | 3.05 | 0.04 |
| Q96S59 | Ran-binding protein 9 | 0.69 | 0.01 |
| Q9Y4G8 | Rap guanine nucleotide exchange factor 2 | 0.72 | 0.01 |
| Q13283 | Ras GTPase-activating protein-binding protein 1 | 0.68 | 0.04 |
| P15153 | Ras-related C3 botulinum toxin substrate 2 | 1.05 | 0.04 |
| P60763 | Ras-related C3 botulinum toxin substrate 3 | 0.97 | 0.03 |
| B4DQU5 | Ras-related protein Rab-11A | 0.67 | 0.04 |
| Q9UL25 | Ras-related protein Rab-21 | 0.69 | <0.01 |
| K7ES41 | Ras-related protein Rab-27B | 1.46 | 0.01 |
| Q8WUD1 | Ras-related protein Rab-2B | 0.80 | 0.01 |
| Q9NP90 | Ras-related protein Rab-9B | 1.47 | 0.04 |
| F6U784 | Ras-related protein Rap-2a | 1.16 | 0.05 |
| O43353 | Receptor-interacting serine/threonine-protein kinase 2 | 0.78 | 0.04 |
| P23471 | Receptor-type tyrosine-protein phosphatase zeta | 0.90 | <0.01 |
| J3KQ66 | Reelin | 0.70 | 0.01 |
| Q15493 | Regucalcin | 1.91 | 0.03 |
| H0YLG5 | Regulator of microtubule dynamics protein 3 | 0.93 | 0.04 |
| Q92900 | Regulator of nonsense transcripts 1 | 0.80 | 0.03 |
| B5MC59 | Replication protein A 14 kDa subunit | 0.71 | <0.01 |
| Q15293 | Reticulocalbin-1 | 1.35 | 0.03 |
| Q86UN3 | Reticulon-4 receptor-like 2 | 1.18 | 0.01 |
| Q5SYQ7 | Retinal dehydrogenase 1 | 1.04 | 0.01 |
| Q8TC12 | Retinol dehydrogenase 11 | −0.73 | 0.02 |
| J3KRE2 | Rho GDP-dissociation inhibitor 1 | 0.80 | 0.03 |
| Q9P227 | Rho GTPase-activating protein 23 | 0.88 | <0.01 |
| E9PMN0 | Ribonuclease inhibitor | 0.70 | 0.04 |
| H0YB34 | Ribonuclease UK114 | 1.04 | 0.02 |
| Q9Y3A5 | Ribosome maturation protein SBDS | 0.86 | 0.05 |
| O15034 | RIMS-binding protein 2 | 2.48 | 0.04 |
| Q5TZA2 | Rootletin | 0.77 | 0.03 |
| H7C5W9 | Sarcoplasmic/endoplasmic reticulum calcium ATPase 2 | 0.77 | 0.05 |
| D6RD99 | Scrapie-responsive protein 1 | 0.70 | 0.02 |
| P05060 | Secretogranin-1 | 0.80 | 0.03 |
| H0YKC2 | Secretogranin-3 | 0.87 | 0.01 |
| C9JDT0 | Secretoneurin | 1.16 | 0.01 |
| O75326 | Semaphorin-7A | 0.85 | <0.01 |
| H7C299 | Septin-5 | 0.83 | 0.02 |
| K7EJ51 | Septin-9 | 0.96 | 0.04 |
| B4DLV4 | Serine hydroxymethyltransferase | −1.13 | 0.03 |
| P34897 | Serine hydroxymethyltransferase, mitochondrial | −1.81 | 0.04 |
| O75494 | Serine/arginine-rich splicing factor 10 | 0.79 | 0.02 |
| E9PCD1 | Serine/threonine-protein kinase WNK2 | 0.75 | 0.01 |
| E9PH38 | Serine/threonine-protein phosphatase 2A 65 kDa regulatory subunit A alpha isoform | 1.00 | 0.02 |
| E9PHZ6 | Serine/threonine-protein phosphatase 2A 65 kDa regulatory subunit A beta isoform | 1.36 | 0.05 |
| Q68CR8 | Serine/threonine-protein phosphatase 2A activator | 0.69 | <0.01 |
| M0QWZ7 | Serine--tRNA ligase, mitochondrial | 1.17 | 0.02 |
| Q6ZV89 | SH2 domain-containing protein 5 | −0.80 | 0.04 |
| Q9BQI5 | SH3-containing GRB2-like protein 3-interacting protein 1 | 0.72 | <0.01 |
| P45954 | Short/branched chain specific acyl-CoA dehydrogenase, mitochondrial | 1.11 | <0.01 |
| A6NMU3 | Signal transducing adapter molecule 1 | 1.06 | 0.02 |
| C9K0U8 | Single-stranded DNA-binding protein, mitochondrial | 0.67 | 0.04 |
| Q96PX8 | SLIT and NTRK-like protein 1 | 0.77 | 0.02 |
| K7EMD6 | Small glutamine-rich tetratricopeptide repeat-containing protein alpha | 1.62 | <0.01 |
| Q8NHG7 | Small VCP/p97-interacting protein | 0.76 | 0.03 |
| Q99250 | Sodium channel protein type 2 subunit alpha | 0.80 | 0.05 |
| Q99884 | Sodium-dependent proline transporter | 1.26 | 0.01 |
| Q5VZ42 | Solute carrier family 12 member 5 | 0.83 | <0.01 |
| P61278 | Somatostatin | 1.03 | 0.03 |
| Q9BX66 | Sorbin and SH3 domain-containing protein 1 | 0.82 | 0.05 |
| Q99523 | Sortilin | 0.68 | 0.03 |
| Q9H4F8 | SPARC-related modular calcium-binding protein 1 | 0.91 | <0.01 |
| H0YJE6 | Spectrin beta chain, erythrocytic | 0.80 | <0.01 |
| K7EJR2 | Spermatogenesis-associated protein 22 | 0.66 | 0.03 |
| H3BS51 | Sphingomyelin phosphodiesterase 3 | 1.31 | 0.02 |
| Q13838 | Spliceosome RNA helicase DDX39B | 0.85 | 0.05 |
| H0Y9U2 | Splicing factor, proline- and glutamine-rich | 1.45 | 0.01 |
| Q9HCB6 | Spondin-1 | 0.75 | <0.01 |
| A2A2D0 | Stathmin | 0.78 | 0.04 |
| P31040 | Succinate dehydrogenase [ubiquinone] flavoprotein subunit, mitochondrial | 1.05 | 0.03 |
| C9J8Q5 | Succinate-semialdehyde dehydrogenase, mitochondrial | 0.77 | 0.01 |
| P17600 | Synapsin-1 | 0.95 | 0.03 |
| Q92777 | Synapsin-2 | 0.86 | 0.03 |
| Q496J9 | Synaptic vesicle glycoprotein 2C | 1.15 | 0.02 |
| K7EM19 | Synaptic vesicle membrane protein VAT-1 homolog | 0.78 | 0.04 |
| H7C4W3 | Synaptophysin | 2.38 | 0.03 |
| C9J0A2 | Synaptoporin | 0.92 | 0.03 |
| F5GX00 | Synaptotagmin-7 | 1.50 | <0.01 |
| F5GZI8 | T-complex protein 1 subunit alpha | 0.89 | 0.03 |
| P78371 | T-complex protein 1 subunit beta | 0.69 | 0.02 |
| E9PM09 | T-complex protein 1 subunit gamma | 1.64 | 0.03 |
| P24821 | Tenascin | 0.73 | 0.05 |
| Q08629 | Testican-1 | 1.73 | <0.01 |
| Q9BQ16 | Testican-3 | 0.84 | 0.03 |

TABLE 5-continued

Biomarkers up/down-regulated in the CSF of AD patient versus control

| UniProtKB Accession Number | Protein name | Log2 AD/Control | P value |
|---|---|---|---|
| J3QL04 | Tether-containing UBX domain for GLUT4 | 1.13 | 0.03 |
| H0YB37 | Tetratricopeptide repeat protein 1 | 1.03 | 0.02 |
| Q86TV6 | Tetratricopeptide repeat protein 7B | 0.95 | <0.01 |
| P10599 | Thioredoxin | 0.93 | 0.03 |
| K7EME7 | Thioredoxin-like protein 1 | 1.28 | 0.01 |
| C9JV37 | Thrombin light chain | −0.71 | 0.03 |
| Q9Y2W1 | Thyroid hormone receptor-associated protein 3 | 1.19 | 0.03 |
| G3V1L9 | Tight junction protein 1 (Zona occludens 1), isoform CRA_a | 0.67 | 0.03 |
| P13726 | Tissue factor | 0.68 | 0.02 |
| E7EN89 | Toll interacting protein, isoform CRA_b | 0.74 | 0.01 |
| F2Z393 | Transaldolase | 0.86 | 0.01 |
| Q5H9L2 | Transcription elongation factor A protein-like 5 | 1.76 | 0.01 |
| E9PL10 | Transcription factor BTF3 homolog 4 | 1.33 | <0.01 |
| M0R3C0 | Transcription intermediary factor 1-beta | 0.78 | 0.04 |
| Q00577 | Transcriptional activator protein Pur-alpha | 1.06 | 0.04 |
| B4DQI6 | Transformer-2 protein homolog alpha | 0.77 | 0.02 |
| H7BXF3 | Transformer-2 protein homolog beta | 0.72 | 0.04 |
| J3KQ45 | Trans-Golgi network integral membrane protein 2 | 0.80 | 0.05 |
| F8W888 | Transketolase | 1.44 | <0.01 |
| Q9BSH4 | Translational activator of cytochrome c oxidase 1 (Coiled-coil domain-containing protein 44) (Translational activator of mitochondrially-encoded cytochrome c oxidase I) | 1.13 | 0.01 |
| Q53FP2 | Transmembrane protein 35 | 0.87 | 0.05 |
| Q9BTV4 | Transmembrane protein 43 | −0.80 | 0.05 |
| C9JE81 | Trifunctional enzyme subunit beta, mitochondrial | 0.68 | 0.02 |
| P60174 | Triosephosphate isomerase | 1.00 | 0.05 |
| F2Z2W7 | tRNA (uracil-5-)-methyltransferase homolog A | 0.89 | <0.01 |
| Q9Y3I0 | tRNA-splicing ligase RtcB homolog | 1.15 | 0.01 |
| P28289 | Tropomodulin-1 | 1.00 | 0.04 |
| Q15714 | TSC22 domain family protein 1 | 0.89 | <0.01 |
| F8VXZ7 | Tubulin alpha-1A chain | 0.95 | 0.01 |
| M0QZL7 | Tubulin beta-4A chain | 0.75 | 0.01 |
| D6RG15 | Twinfilin-2 | −0.99 | 0.01 |
| P06241 | Tyrosine-protein kinase Fyn (EC 2.7.10.2) (Proto-oncogene Syn) (Proto-oncogene c-Fyn) (Src-like kinase) (SLK) (p59-Fyn) | 0.79 | 0.02 |
| E9PLZ4 | Tyrosine-protein phosphatase non-receptor type 5 | 0.98 | 0.02 |
| M0QYR1 | U1 small nuclear ribonucleoprotein 70 kDa (Fragment) | 0.75 | <0.01 |
| Q9UHD9 | Ubiquilin-2 | 1.15 | 0.01 |
| K7EJ02 | UBX domain-containing protein 6 | −0.78 | 0.01 |
| Q14376 | UDP-glucose 4-epimerase | 0.82 | 0.02 |
| E9PPU6 | Uncharacterized protein | −0.70 | 0.01 |
| Q9BXV9 | Uncharacterized protein C14orf142 | 0.70 | 0.03 |
| H0YEV9 | Unconventional myosin-XVIIIa | −0.81 | 0.02 |
| Q9H3H3 | UPF0696 protein C11orf68 | 0.83 | 0.01 |
| K7ELW1 | UV excision repair protein RAD23 homolog A | 0.81 | 0.01 |
| Q5W0S4 | UV excision repair protein RAD23 homolog B | 0.96 | <0.01 |
| Q709C8 | Vacuolar protein sorting-associated protein 13C | 1.45 | 0.03 |
| Q6EMK4 | Vasorin | 0.80 | 0.04 |
| P49748 | Very long-chain specific acyl-CoA dehydrogenase, mitochondrial | 0.91 | 0.01 |
| B0YJC4 | Vimentin | 0.80 | 0.03 |
| H0Y715 | Voltage-dependent calcium channel subunit alpha-2/delta-1 | 0.87 | 0.01 |
| B5MCX6 | V-set and transmembrane domain-containing protein 2A | 0.81 | 0.01 |
| K7ERA0 | V-type proton ATPase subunit a | 0.74 | <0.01 |
| Q8N8Y2 | V-type proton ATPase subunit d 2 | 1.66 | 0.01 |
| Q15904 | V-type proton ATPase subunit S1 | 1.00 | 0.02 |
| Q8TF74 | WAS/WASL-interacting protein family member 2 | 1.71 | 0.02 |
| H0YMF9 | WD repeat-containing protein 61 | −2.20 | <0.01 |
| Q9UPY6 | Wiskott-Aldrich syndrome protein family member 3 | 0.77 | 0.03 |
| P61129 | Zinc finger CCCH domain-containing protein 6 | 1.08 | 0.04 |
| Q9ULF5 | Zinc transporter ZIP10 | 0.76 | 0.02 |

In one embodiment, the panel of biomarkers comprises at least Basigin.

In another embodiment, the panel of biomarkers comprises at least Cytochrome c oxidase subunit 7A-related protein, mitochondrial.

In another embodiment, the panel of biomarkers comprises at least Basigin and Cytochrome c oxidase subunit 7A-related protein, mitochondrial.

Basigin or BSG or extracellular matrix metalloproteinase inducer (EMMPRIN) or cluster of differentiation 147 (CD147) is a type I integral membrane receptor that has many ligands, including the cyclophilin (CyP) proteins Cyp-A and CyP-B and certain integrins. Basigin has metalloproteinase-inducing ability and it also regulates several distinct functions, such as spermatogenesis, expression of the monocarboxylate transporter and the responsiveness of lymphocytes. It is expressed by many cell types, including epithelial cells, endothelial cells and leukocytes. The human Basigin protein contains 269 amino acids that form two heavily glycosylated C2 type immunoglobulin-like domains at the N-terminal extracellular portion. A second form of Basigin has also been characterized that contains one additional immunoglobulin-like domain in its extracellular portion. Its amino acid sequence is depicted in SEQ ID NO: 30.

Cytochrome c oxidase subunit 7A-related protein, mitochondrial or Cox7r is an enzyme encoded by the COX7A2L gene in humans. Cytochrome c oxidase subunit 7A-related protein, mitochondrial is a component of the Cytochrome c oxidase (COX), which is the terminal component of the mitochondrial respiratory chain and catalyzes the electron transfer from reduced cytochrome c to oxygen. Its amino acid sequence is depicted in SEQ ID NO: 31.

The embodiments relating to the biomarkers selected from Table 5, as described above, are equally applicable to all other embodiments of the third aspect of the invention and to all other aspects of the invention where biomarkers selected from Table 5 are involved.

In one embodiment, the panel of biomarker comprises at least one biomarker selected from Table 5 and at least one biomarker selected from tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid.

Preferably, the panel also comprises one biomarker selected from Groups A, B, C or D. More preferably the biomarker selected from Groups A, B, C or D is:
  i) protein phosphatase 1 regulatory subunit 14A comprising or having the amino acid sequence of SEQ ID NO:1 or an isoform or a variant or a fragment thereof; or
  ii) 2',3'-cyclic-nucleotide 3'-phosphodiesterase comprising or having the amino acid sequence of SEQ ID NO:2 or an isoform or a variant or a fragment thereof.

The biomarkers listed in Table 5 may belong to specific pathways which are known to be relevant in the pathology of AD. They may be further grouped in specific lists as those illustrated below in Tables 6 to 13 according to specific GO terms (http://geneontology.org/).

One GO term used to analyse the data was the term "Synap*". Biomarkers of Table 5 which are registered as part of this specific pathway are shown in Table 6.

In one embodiment, the panel of biomarkers according to the invention comprises one or more, preferably two or more biomarkers selected from Table 6.

TABLE 6

Proteins with GO Term 'Synap*' found to be regulated in CSF of AD patients

| UniProtKB Accession Number | Protein name | Log2 AD/Control | P value |
|---|---|---|---|
| P05067 | Amyloid beta A4 protein | 0.90 | <0.01 |
| Q9UQM7 | Calcium/calmodulin-dependent protein kinase type II subunit alpha | 0.81 | 0.02 |
| Q16566 | Calcium/calmodulin-dependent protein kinase type IV | 0.85 | 0.03 |
| C9IZ88 | Catenin alpha-2 | 2.11 | 0.01 |
| Q5JYX0 | Cell division control protein 42 homolog | 1.04 | 0.05 |
| I3L0M4 | Coiled-coil domain-containing protein 43 | 0.99 | 0.01 |
| Q8NFT8 | Delta and Notch-like epidermal growth factor-related receptor | 1.02 | 0.01 |
| P50570 | Dynamin-2 | 0.89 | 0.03 |
| P42261 | Glutamate receptor 1 | 1.13 | 0.04 |
| P01112 | GTPase HRas | 1.09 | 0.01 |
| M0R2G0 | Leucine-rich repeat-containing protein 4B | 0.76 | <0.01 |
| Q9Y4C0 | Neurexin-3 | 0.93 | <0.01 |
| Q9HDB5 | Neurexin-3-beta | 0.98 | <0.01 |
| P61601 | Neurocalcin-delta | 1.33 | 0.03 |
| Q9UBB6 | Neurochondrin | 0.80 | 0.02 |
| Q8NFZ4 | Neuroligin-2 | 0.96 | 0.04 |
| P47972 | Neuronal pentraxin-2 | 1.02 | 0.01 |
| Q96HC4 | PDZ and LIM domain protein 5 | 0.75 | 0.02 |
| I3L495 | Platelet-activating factor acetylhydrolase IB subunit alpha | 0.97 | 0.02 |
| Q09470 | Potassium voltage-gated channel subfamily A member 1 | 0.73 | 0.04 |
| P01303 | Pro-neuropeptide Y | 0.86 | 0.04 |
| Q02156 | Protein kinase C epsilon type | 0.99 | 0.02 |
| Q9Y6V0 | Protein piccolo | 0.93 | 0.04 |
| Q9Y4G8 | Rap guanine nucleotide exchange factor 2 | 0.72 | 0.01 |
| P61278 | Somatostatin | 1.03 | 0.03 |
| P17600 | Synapsin-1 | 0.95 | 0.03 |
| Q92777 | Synapsin-2 | 0.86 | 0.03 |
| H7C4W3 | Synaptophysin | 2.38 | 0.03 |

In one embodiment, the panel of biomarker comprises at least one biomarker selected from Table 6 and at least one biomarker selected from tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid.

Preferably, the panel also comprises one biomarker selected from Groups A, B, C or D. More preferably the biomarker selected from Groups A, B, C or D is:
  i) protein phosphatase 1 regulatory subunit 14A comprising or having the amino acid sequence of SEQ ID NO:1 or an isoform or a variant or a fragment thereof; or
  ii) 2',3'-cyclic-nucleotide 3'-phosphodiesterase comprising or having the amino acid sequence of SEQ ID NO:2 or an isoform or a variant or a fragment thereof.

Another GO term used to analyse the data was the term "Phosphoryl*". Biomarkers of Table 5 which are registered as part of this specific pathway are shown in Table 7.

In another embodiment, the panel of biomarkers according to the invention comprises one or more, preferably two or more biomarkers selected from Table 7.

TABLE 7

Proteins with GO Term 'Phosporyl*' found to be regulated in CSF of AD patients

| UniProtKB Accession Number | Protein name | Log2 AD/Control | P value |
|---|---|---|---|
| Q8IZP0 | Abl interactor 1 | 1.04 | 0.01 |
| P05067 | Amyloid beta A4 protein | 0.90 | <0.01 |
| P03950 | Angiogenin | −0.76 | 0.03 |
| P17858 | ATP-dependent 6-phosphofructokinase, liver type | 0.68 | 0.02 |
| P11274 | Breakpoint cluster region protein | 0.99 | 0.01 |
| Q9UQM7 | Calcium/calmodulin-dependent protein kinase type II subunit alpha | 0.81 | 0.02 |
| Q16566 | Calcium/calmodulin-dependent protein kinase type IV | 0.85 | 0.03 |
| P31321 | cAMP-dependent protein kinase type I-beta regulatory subunit | 1.56 | 0.04 |
| Q5JYX0 | Cell division control protein 42 homolog | 1.04 | 0.05 |
| O75367 | Core histone macro-H2A.1 | 0.67 | 0.01 |
| P14927 | Cytochrome b-c1 complex subunit 7 | 0.98 | 0.05 |
| Q08495 | Dematin | 0.76 | 0.01 |
| P20827 | Ephrin-A1 | 0.86 | 0.05 |
| E5RGR6 | GDNF family receptor alpha-2 | 1.06 | <0.01 |
| P01112 | GTPase HRas | 1.09 | 0.01 |
| H0YB38 | Inositol monophosphatase 3 | 1.12 | 0.04 |
| K7EKJ9 | Interleukin enhancer-binding factor 3 | 1.57 | 0.04 |
| A2A2V1 | Major prion protein | 1.20 | <0.01 |
| Q15746 | Myosin light chain kinase, smooth muscle | 1.08 | 0.01 |
| O14936 | Peripheral plasma membrane protein CASK | 1.07 | 0.04 |
| A8MTF1 | Phosphatidylinositol 4-kinase alpha | 0.71 | 0.01 |
| A6NDG6 | Phosphoglycolate phosphatase | 1.05 | 0.03 |

TABLE 7-continued

Proteins with GO Term 'Phosporyl*' found to be regulated in CSF of AD patients

| UniProtKB Accession Number | Protein name | Log2 AD/Control | P value |
|---|---|---|---|
| Q9H008 | Phospholysine phosphohistidine inorganic pyrophosphate phosphatase | 0.74 | 0.03 |
| Q02156 | Protein kinase C epsilon type | 0.99 | 0.02 |
| Q5SYT8 | Protein NAMPTL | 0.83 | 0.03 |
| O75323 | Protein NipSnap homolog 2 | 1.61 | 0.02 |
| Q96A00 | Protein phosphatase 1 regulatory subunit 14A | 0.70 | 0.05 |
| O43353 | Receptor-interacting serine/threonine-protein kinase 2 | 0.78 | 0.04 |
| P23471 | Receptor-type tyrosine-protein phosphatase zeta | 0.90 | <0.01 |
| O75326 | Semaphorin-7A | 0.85 | <0.01 |
| M0R3C0 | Transcription intermediary factor 1-beta | 0.78 | 0.04 |
| P06241 | Tyrosine-protein kinase Fyn (EC 2.7.10.2) (Proto-oncogene Syn) (Proto-oncogene c-Fyn) (Src-like kinase) (SLK) (p59-Fyn) | 0.79 | 0.02 |

In one embodiment, the panel of biomarker comprises at least one biomarker selected from Table 7 and at least one biomarker selected from tau or one or more fragments thereof, wherein tau:

i) comprises or has the amino acid sequence of SEQ ID NO:29 and ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid.

Preferably, the panel also comprises one biomarker selected from Groups A, B, C or D. More preferably the biomarker selected from Groups A, B, C or D is:

i) protein phosphatase 1 regulatory subunit 14A comprising or having the amino acid sequence of SEQ ID NO:1 or an isoform or a variant or a fragment thereof;

or ii) 2',3'-cyclic-nucleotide 3'-phosphodiesterase comprising or having the amino acid sequence of SEQ ID NO:2 or an isoform or a variant or a fragment thereof.

Another GO term used to analyse the data was the term "Stress". Biomarkers of Table 5 which are registered as part of this specific pathway are shown in Table 8.

In another embodiment, the panel of biomarkers according to the invention comprises one or more, preferably two or more biomarkers selected from Table 8.

TABLE 8

Proteins with GO Term 'Stress' found to be regulated in CSF of AD patients

| UniProtKB Accession Number | Protein name | Log2 AD/Control | P value |
|---|---|---|---|
| P11766 | Alcohol dehydrogenase class-3 | 0.87 | 0.05 |
| P05067 | Amyloid beta A4 protein | 0.90 | <0.01 |
| E9PMA0 | Apoptosis-inducing factor 1, mitochondrial | 0.69 | 0.03 |
| P29972 | Aquaporin-1 | 0.90 | <0.01 |
| Q99674 | Cell growth regulator with EF hand domain protein 1 | 0.86 | <0.01 |
| H0YIV0 | Endoplasmin | 1.18 | 0.04 |
| P07203 | Glutathione peroxidase 1 | 1.13 | 0.02 |
| C9J3N8 | Heat shock protein beta-1 | −0.91 | 0.01 |
| Q9Y4L1 | Hypoxia up-regulated protein 1 | 0.86 | 0.02 |
| Q13136 | Liprin-alpha-1 | 0.85 | 0.01 |
| A2A2V1 | Major prion protein | 1.20 | <0.01 |
| E5RJK1 | Mitochondrial peptide methionine sulfoxide reductase | 0.87 | <0.01 |
| P32119 | Peroxiredoxin-2 | 0.96 | 0.03 |
| P60903 | Protein S100-A10 | 0.75 | 0.02 |
| O43353 | Receptor-interacting serine/threonine-protein kinase 2 | 0.78 | 0.04 |
| Q99250 | Sodium channel protein type 2 subunit alpha | 0.80 | 0.05 |
| Q9BX66 | Sorbin and SH3 domain-containing protein 1 | 0.82 | 0.05 |

In yet another embodiment, the panel of biomarker comprises at least one biomarker selected from Table 8 and at least one biomarker selected from tau or one or more fragments thereof, wherein tau:

i) comprises or has the amino acid sequence of SEQ ID NO:29 and ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid.

Preferably, the panel also comprises one or more biomarker selected from Groups A, B, C or D. More preferably the one or more biomarkers selected from Groups A, B, C or D is:

i) protein phosphatase 1 regulatory subunit 14A comprising or having the amino acid sequence of SEQ ID NO:1 or an isoform or a variant or a fragment thereof;

or ii) 2',3'-cyclic-nucleotide 3'-phosphodiesterase comprising or having the amino acid sequence of SEQ ID NO:2 or an isoform or a variant or a fragment thereof.

Another GO term used to analyse the data was the term "Calcium". Biomarkers of Table 5 which are registered as part of this specific pathway are shown in Table 9.

In another embodiment, the panel of biomarkers according to the invention comprises one or more, preferably two or more biomarkers selected from Table 9.

TABLE 9

Proteins with GO Term 'Calcium' found to be regulated in CSF of AD patients

| UniProtKB Accession Number | Protein name | Log2 AD/Control | P value |
|---|---|---|---|
| P05067 | Amyloid beta A4 protein | 0.90 | <0.01 |
| E7EV01 | Ankyrin repeat and SOCS box protein 2 | 1.68 | 0.01 |
| P07686 | Beta-hexosaminidase subunit beta | 1.49 | <0.01 |
| P19022 | Cadherin-2 | 1.17 | 0.05 |
| Q9UQM7 | Calcium/calmodulin-dependent protein kinase type II subunit alpha | 0.81 | 0.02 |
| P07384 | Calpain-1 catalytic subunit | 1.06 | 0.03 |
| Q96A33 | Coiled-coil domain-containing protein 47 | 0.79 | 0.02 |
| Q08495 | Dematin | 0.76 | 0.01 |
| P78417 | Glutathione S-transferase omega-1 | 1.13 | 0.01 |
| P13645 | Keratin, type I cytoskeletal 10 | 0.66 | 0.02 |
| P01042 | Kininogen-1 | -0.67 | 0.02 |
| Q15746 | Myosin light chain kinase, smooth muscle | 1.08 | 0.01 |
| P61601 | Neurocalcin-delta | 1.33 | 0.03 |
| Q9UBV8 | Peflin | 0.98 | 0.03 |
| O14936 | Peripheral plasma membrane protein CASK | 1.07 | 0.04 |
| P01303 | Pro-neuropeptide Y | 0.86 | 0.04 |
| Q02156 | Protein kinase C epsilon type | 0.99 | 0.02 |
| Q15493 | Regucalcin | 1.91 | 0.03 |
| H7C5W9 | Sarcoplasmic/endoplasmic reticulum calcium ATPase 2 | 0.77 | 0.05 |
| P06241 | Tyrosine-protein kinase Fyn (EC 2.7.10.2) (Proto-oncogene Syn) (Proto-oncogene c-Fyn) (Src-like kinase) (SLK) (p59-Fyn) | 0.79 | 0.02 |

In one another embodiment, the panel of biomarker comprises at least one biomarker selected from Table 9 and at least one biomarker selected from tau or one or more fragments thereof, wherein tau:

i) comprises or has the amino acid sequence of SEQ ID NO:29 and ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid.

Preferably, the panel also comprises one biomarker selected from Groups A, B, C or D. More preferably the biomarker selected from Groups A, B, C or D is:

i) protein phosphatase 1 regulatory subunit 14A comprising or having the amino acid sequence of SEQ ID NO:1 or an isoform or a variant or a fragment thereof; or ii) 2',3'-cyclic-nucleotide 3'-phosphodiesterase comprising or having the amino acid sequence of SEQ ID NO:2 or an isoform or a variant or a fragment thereof.

Another GO term used to analyse the data was the term "Cytoskelet*". Biomarkers of Table 5 which are registered as part of this specific pathway are shown in Table 10.

In another embodiment, the panel of biomarker according to the invention comprises one or more, preferably two or more biomarkers selected from Table 10.

TABLE 10

Proteins with GO Term 'Cytoskelet*' found to be regulated in CSF of AD patients

| UniProtKB Accession Number | Protein name | Log2 AD/Control | P value |
|---|---|---|---|
| Q8IZP0 | Abl interactor 1 | 1.04 | 0.01 |
| E9PF58 | Actin-related protein 2/3 complex subunit 1A | 0.94 | 0.02 |
| P16157 | Ankyrin-1 | 0.86 | 0.01 |
| P04114 | Apolipoprotein B-100 | 0.70 | 0.04 |
| Q4VXN1 | Band 4.1-like protein 1 | 1.36 | 0.01 |
| Q562R1 | Beta-actin-like protein 2 | 0.77 | 0.05 |
| C9IZ88 | Catenin alpha-2 | 2.11 | 0.01 |
| Q14019 | Coactosin-like protein | 0.68 | 0.02 |
| Q08495 | Dematin | 0.76 | 0.01 |
| P60981 | Destrin | 0.93 | 0.05 |
| Q15334 | Lethal(2) giant larvae protein homolog 1 | 0.74 | 0.04 |
| O14745 | Na(+)/H(+) exchange regulatory cofactor NHE-RF1 | 1.06 | 0.05 |
| Q96HC4 | PDZ and LIM domain protein 5 | 0.75 | 0.02 |
| O14936 | Peripheral plasma membrane protein CASK | 1.07 | 0.04 |
| Q02156 | Protein kinase C epsilon type | 0.99 | 0.02 |
| Q9Y6V0 | Protein piccolo | 0.93 | 0.04 |
| O43353 | Receptor-interacting serine/threonine-protein kinase 2 | 0.78 | 0.04 |
| Q5TZA2 | Rootletin | 0.77 | 0.03 |
| B4DLV4 | Serine hydroxymethyltransferase | -1.13 | 0.03 |
| P34897 | Serine hydroxymethyltransferase, mitochondrial | -1.81 | 0.04 |
| P28289 | Tropomodulin-1 | 1.00 | 0.04 |
| B0YJC4 | Vimentin | 0.80 | 0.03 |
| Q8TF74 | WAS/WASL-interacting protein family member 2 | 1.71 | 0.02 |
| Q9UPY6 | Wiskott-Aldrich syndrome protein family member 3 | 0.77 | 0.03 |

In another embodiment, the panel of biomarker comprises at least one biomarker selected from Table 10 and at least one biomarker selected from tau or one or more fragments thereof, wherein tau:

i) comprises or has the amino acid sequence of SEQ ID NO:29 and ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid.

Preferably, the panel also comprises one or more biomarkers selected from Groups A, B, C or D. More preferably the one or more biomarkers selected from Groups A, B, C or D is:

i) protein phosphatase 1 regulatory subunit 14A comprising or having the amino acid sequence of SEQ ID NO:1 or an isoform or a variant or a fragment thereof; or ii) 2',3'-cyclic-nucleotide 3'-phosphodiesterase comprising or having the amino acid sequence of SEQ ID NO:2 or an isoform or a variant or a fragment thereof.

Yet another GO term used to analyse the data was the term "Mitochondri*". Biomarkers of Table 5 which are registered as part of this specific pathway are shown in Table 11.

In another embodiment, the panel of biomarkers according to the invention comprises one or more, preferably two or more biomarkers selected from Table 11.

TABLE 11

Proteins with GO Term 'Mitochondri*' found to be regulated in CSF of AD patients

| UniProtKB Accession Number | Protein name | Log2 AD/Control | P value |
|---|---|---|---|
| K7EJ68 | 3-ketoacyl-CoA thiolase, mitochondrial | 0.91 | 0.01 |
| P25325 | 3-mercaptopyruvate sulfurtransferase | 0.81 | 0.01 |
| O14561 | Acyl carrier protein, mitochondrial | 0.72 | 0.02 |
| P07108 | Acyl-CoA-binding protein | 1.18 | 0.02 |
| O14734 | Acyl-coenzyme A thioesterase 8 | 0.76 | <0.01 |
| P12235 | ADP/ATP translocase 1 | 0.71 | 0.03 |
| P11766 | Alcohol dehydrogenase class-3 | 0.87 | 0.05 |
| E9PMA0 | Apoptosis-inducing factor 1, mitochondrial | 0.69 | 0.03 |
| O43776 | Asparagine--tRNA ligase, cytoplasmic | 1.37 | 0.03 |
| K7EJP1 | ATP synthase subunit alpha, mitochondrial | 0.77 | 0.04 |
| Q86VU5 | Catechol O-methyltransferase domain-containing protein 1 | 1.06 | 0.01 |
| Q8NI60 | Chaperone activity of bc1 complex-like, mitochondrial | 0.78 | 0.01 |
| H3BP04 | Cytochrome b-c1 complex subunit 2, mitochondrial | 0.67 | 0.02 |
| P14927 | Cytochrome b-c1 complex subunit 7 | 0.98 | 0.05 |
| P47985 | Cytochrome b-c1 complex subunit Rieske, mitochondrial | 1.13 | 0.04 |
| Q5JTJ3 | Cytochrome c oxidase assembly factor 6 homolog | 1.23 | 0.01 |
| K7EQD3 | Cytochrome c oxidase subunit 6B1 | 0.88 | 0.02 |
| E5RJZ1 | Cytochrome c oxidase subunit 7A-related protein, mitochondrial | 4.19 | 0.05 |
| Q9NVH1 | DnaJ homolog subfamily C member 11 | 0.94 | 0.01 |
| Q92506 | Estradiol 17-beta-dehydrogenase 8 | 0.87 | 0.04 |
| Q92731 | Estrogen receptor beta | 1.73 | 0.01 |
| G3V1D1 | Ferritin | 1.37 | 0.03 |
| P07203 | Glutathione peroxidase 1 | 1.13 | 0.02 |
| P23434 | Glycine cleavage system H protein, mitochondrial | 0.94 | 0.01 |
| P08107 | Heat shock 70 kDa protein 1A/1B | 0.70 | 0.03 |
| F5GWX2 | Heme-binding protein 1 | 1.24 | <0.01 |
| B1AR61 | Hexokinase-1 | 0.83 | 0.02 |
| Q16775 | Hydroxyacylglutathione hydrolase, mitochondrial | 0.85 | 0.04 |
| K7EKJ9 | Interleukin enhancer-binding factor 3 | 1.57 | 0.04 |
| Q5VVL7 | Lipoamide acyltransferase component of branched-chain alpha-keto acid dehydrogenase complex, mitochondrial | 0.84 | 0.03 |
| A8MW50 | L-lactate dehydrogenase | 0.72 | 0.02 |
| F5GZQ4 | L-lactate dehydrogenase A chain | 0.68 | <0.01 |
| O95573 | Long-chain-fatty-acid--CoA ligase 3 | 0.82 | 0.01 |
| C9JF79 | Malate dehydrogenase | 1.07 | 0.04 |
| Q5HYI7 | Metaxin-3 | 1.07 | <0.01 |
| Q13825 | Methylglutaconyl-CoA hydratase, mitochondrial | 1.50 | 0.03 |
| Q9H936 | Mitochondrial glutamate carrier 1 | 0.66 | <0.01 |
| G3V502 | Mitochondrial import inner membrane translocase subunit Tim9 | 0.92 | 0.03 |
| E5RJK1 | Mitochondrial peptide methionine sulfoxide reductase | 0.87 | <0.01 |
| Q10713 | Mitochondrial-processing peptidase subunit alpha | 0.70 | 0.04 |
| D6RAU3 | Mitogen-activated protein kinase 10 | 0.65 | 0.04 |
| O95865 | N(G),N(G)-dimethylarginine dimethylaminohydrolase 2 | 0.83 | 0.01 |
| Q4G0N4 | NAD kinase 2, mitochondrial | 0.96 | <0.01 |
| D6RAI5 | NAD(P) transhydrogenase, mitochondrial | 0.86 | <0.01 |
| F8VRD8 | NADH dehydrogenase [ubiquinone] 1 alpha subcomplex subunit 12 | 1.00 | 0.05 |
| O95182 | NADH dehydrogenase [ubiquinone] 1 alpha subcomplex subunit 7 | 0.73 | 0.02 |
| Q16795 | NADH dehydrogenase [ubiquinone] 1 alpha subcomplex subunit 9, mitochondrial | 0.74 | 0.04 |
| E9PQ68 | NADH dehydrogenase [ubiquinone] 1 beta subcomplex subunit 8, mitochondrial | −0.85 | <0.01 |
| P56181 | NADH dehydrogenase [ubiquinone] flavoprotein 3, mitochondrial | 0.70 | 0.03 |
| Q9UHQ9 | NADH-cytochrome b5 reductase 1 | 0.72 | 0.02 |
| Q02790 | Peptidyl-prolyl cis-trans isomerase FKBP4 | 0.73 | 0.04 |
| F8VVM2 | Phosphate carrier protein, mitochondrial | 0.78 | 0.01 |
| P36969 | Phospholipid hydroperoxide glutathione peroxidase, mitochondrial | 0.75 | 0.02 |
| Q9UHV9 | Prefoldin subunit 2 | 0.72 | 0.04 |
| Q9H7Z7 | Prostaglandin E synthase 2 | 0.98 | 0.02 |
| Q02156 | Protein kinase C epsilon type | 0.99 | 0.02 |
| Q9BPW8 | Protein NipSnap homolog 1 | 0.80 | 0.04 |
| O75323 | Protein NipSnap homolog 2 | 1.61 | 0.02 |
| K7EIR2 | Protein QIL1 | −0.74 | 0.03 |
| H3BTN5 | Pyruvate kinase | 0.71 | 0.03 |
| H0YLG5 | Regulator of microtubule dynamics protein 3 | 0.93 | 0.04 |
| B4DLV4 | Serine hydroxymethyltransferase | −1.13 | 0.03 |
| P34897 | Serine hydroxymethyltransferase, mitochondrial | −1.81 | 0.04 |
| P45954 | Short/branched chain specific acyl-CoA dehydrogenase, mitochondrial | 1.11 | <0.01 |
| C9K0U8 | Single-stranded DNA-binding protein, mitochondrial | 0.67 | 0.04 |
| P31040 | Succinate dehydrogenase [ubiquinone] flavoprotein subunit, mitochondrial | 1.05 | 0.03 |
| C9J8Q5 | Succinate-semialdehyde dehydrogenase, mitochondrial | 0.77 | 0.01 |
| P10599 | Thioredoxin | 0.93 | 0.03 |
| Q9BSH4 | Translational activator of cytochrome c oxidase 1 (Coiled-coil domain-containing protein 44) (Translational activator of mitochondrially-encoded cytochrome c oxidase I) | 1.13 | 0.01 |
| C9JE81 | Trifunctional enzyme subunit beta, mitochondrial | 0.68 | 0.02 |
| P06241 | Tyrosine-protein kinase Fyn (EC 2.7.10.2) (Proto-oncogene Syn) (Proto-oncogene c-Fyn) (Src-like kinase) (SLK) (p59-Fyn) | 0.79 | 0.02 |
| Q6EMK4 | Vasorin | 0.80 | 0.04 |
| P49748 | Very long-chain specific acyl-CoA dehydrogenase, mitochondrial | 0.91 | 0.01 |

In another embodiment, the panel of biomarker comprises at least one biomarker selected from Table 11 and at least one biomarker selected from tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid.

Preferably, the panel also comprises one or more biomarkers selected from Groups A, B, C or D. More preferably the one or more biomarkers selected from Groups A, B, C or D is:

i) protein phosphatase 1 regulatory subunit 14A comprising or having the amino acid sequence of SEQ ID NO:1 or an isoform or a variant or a fragment thereof;
or
ii) 2',3'-cyclic-nucleotide 3'-phosphodiesterase comprising or having the amino acid sequence of SEQ ID NO:2 or an isoform or a variant or a fragment thereof.

The biomarkers of Table 5 were also analysed with the GO terms "Vesicle" and "Insuline". Those which are registered as part of this specific pathways are shown in Table 12 and Table 13, respectively.

In another embodiment, the panel of biomarker according to the invention comprises one or more, preferably two or more biomarkers selected from Table 12 or Table 13.

TABLE 12

Proteins with GO Term 'Vesicle' found to be regulated in CSF of AD patients

| UniProtKB Accession Number | Protein name | Log2 AD/ Control | P value |
|---|---|---|---|
| P16157 | Ankyrin-1 | 0.86 | 0.01 |
| B0YIW6 | Archain 1 | −1.26 | 0.01 |
| Q9UPT6 | C-Jun-amino-terminal kinase-interacting protein 3 | −0.85 | 0.01 |
| D6RJD1 | Clathrin light chain B | 0.84 | 0.02 |
| P53618 | Coatomer subunit beta | 1.07 | 0.03 |
| H0Y8X7 | Coatomer subunit gamma-1 | 0.69 | 0.03 |
| P50570 | Dynamin-2 | 0.89 | 0.03 |
| P61601 | Neurocalcin-delta | 1.33 | 0.03 |
| I3L495 | Platelet-activating factor acetylhydrolase IB subunit alpha | 0.97 | 0.02 |
| Q9Y6V0 | Protein piccolo | 0.93 | 0.04 |
| Q8WUD1 | Ras-related protein Rab-2B | 0.80 | 0.01 |
| Q99523 | Sortilin | 0.68 | 0.03 |
| P17600 | Synapsin-1 | 0.95 | 0.03 |

TABLE 13

Proteins with GO Term 'Insulin' found to be regulated in CSF of AD patients

| UniProtKB Accession Number | Protein name | Log2 AD/ Control | P value |
|---|---|---|---|
| P12235 | ADP/ATP translocase 1 | 0.71 | 0.03 |
| P17174 | Aspartate aminotransferase, cytoplasmic | 0.99 | 0.03 |
| P17858 | ATP-dependent 6-phosphofructokinase, liver type | 0.68 | 0.02 |
| P31321 | cAMP-dependent protein kinase type I-beta regulatory subunit | 1.56 | 0.04 |
| Q9UKG1 | DCC-interacting protein 13-alpha | 0.79 | 0.01 |
| P01112 | GTPase HRas | 1.09 | 0.01 |
| P63092 | Guanine nucleotide-binding protein G(s) subunit alpha isoforms short | 1.00 | 0.03 |
| P16519 | Neuroendocrine convertase 2 | 1.52 | 0.00 |
| O15240 | Neurosecretory protein VGF | 1.12 | 0.00 |
| Q9BZF1 | Oxysterol-binding protein-related protein 8 | 0.78 | 0.04 |
| Q02156 | Protein kinase C epsilon type | 0.99 | 0.02 |
| Q9Y6V0 | Protein piccolo | 0.93 | 0.04 |
| Q9BX66 | Sorbin and SH3 domain-containing protein 1 | 0.82 | 0.05 |
| Q99523 | Sortilin | 0.68 | 0.03 |
| Q8N8Y2 | V-type proton ATPase subunit d 2 | 1.66 | 0.01 |

In other embodiments, the panel of biomarker comprises at least one biomarker selected from Table 12 or Table 13 and at least one biomarker selected from tau or one or more fragments thereof, wherein tau:
i) comprises or has the amino acid sequence of SEQ ID NO:29 and
ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422;
wherein when the phosphorylated amino acid on tau is T181, the panel comprises tau or one or more fragments thereof having at least one more phosphorylated amino acid.

Preferably, the panel also comprises one or more biomarkers selected from Groups A, B, C or D. More preferably the one or more biomarkers selected from Groups A, B, C or D is:
i) protein phosphatase 1 regulatory subunit 14A comprising or having the amino acid sequence of SEQ ID NO:1 or an isoform or a variant or a fragment thereof;
or
ii) 2',3'-cyclic-nucleotide 3'-phosphodiesterase comprising or having the amino acid sequence of SEQ ID NO:2 or an isoform or a variant or a fragment thereof.

All non-modified peptides for each protein were summed for three control and three AD cases. The log 2 ratio and p-value of each protein was then calculated. Proteins with 2 or more peptides, >60% regulation and p<0.05 were selected as biomarkers of synaptic dysfunction (Table 6), dysregulated phosphorylation (Table 7), oxidative stress (Table 8), dysregulated calcium signalling (Table 9), dysregulated cytoskeleton (Table 10), mitochondrial damage (Table 11), abnormal vesicle function (Table 12) and dysfunctional insulin signalling (Table 13).

The panels of biomarkers described herein are useful for diagnosing, for staging, for assessing the likelihood of developing a neurocognitive disorder, and for assessing the response to a drug for treating a neurocognitive disorder, such as a neurocognitive disease characterized by tau toxicity, for example a tauopathy and in particular Alzheimer's disease. The use of these panels of biomarkers according to the present invention in any of such methods has considerable advantages.

Firstly, the biomarkers according to the present invention represent the translation of tau toxicity and resulting changes in pathways that occur in the brain into a peripheral signal in a peripheral tissue such as CSF and blood. Hence, they allow replacing tissue testing with a peripheral fluid testing. This represents a great advantage especially as the tissue primarily affected in neurocognitive disorder is the brain tissue. Brain biopsies are not carried out unless post-mortem.

Secondly, the biomarkers according to the present invention have been selected as those being capable to translate the specific stage of a neurocognitive disorder characterized by tau toxicity, such as Alzheimer's disease. This also represents a great advantage as currently clinicians assess the advancement of a neurocognitive diseases like AD through a battery of psychometric tests, which, albeit being somewhat indicative of the disease progression, may not be precise on the stage of the disease, thus, making it particularly difficult to select those therapies which have been developed and approved for a specific stage.

Thirdly, these biomarkers further comprise proteins which are not those typically reported in the literature or currently used in the clinical setting as biomarkers for tauopathies, thus providing clinicians with additional tools for identifying and distinguishing, even at an early stage, subjects who have a neurocognitive disorder characterized by tau toxicity, such as AD and subjects who, despite presenting symptoms of neurocognitive impairment are not affected by the early signs of AD.

Hence, the present invention provides for a method for diagnosing a neurocognitive disorder in a subject, the method comprising:
  a) assaying a sample obtained from said subject for biomarkers of a panel as defined herein;
  b) measuring in said sample a concentration or an amount of each of the biomarkers of said panel;
  c) determining whether that subject has a neurocognitive disorder by comparing said concentration or amount of each of the biomarkers of the panel in said sample with reference concentrations or amounts of said biomarkers;
wherein the panel of biomarkers is selected from a panel comprising:
I)
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform a variant or a fragment thereof; or
II) one or more biomarkers selected from Groups A, B, C or D; or
III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or
IV) one or more, optionally two or more proteins selected from Tables 5, 6, 7, 8, 9, 10, 11, 12, 13 or combinations thereof; or
V) combinations of I), II), III) and IV.

Preferably, the neurocognitive disorder is characterized by tau-toxicity; more preferably the neurocognitive disorder is a tauopathy selected from the group of Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, chronic traumatic encephalopathy, alpha-synucleinopathies, Parkinson's disease or combinations thereof.

Even more preferably the tauopathy is Alzheimer's disease.

The present invention also provide for a method for staging a neurocognitive disorder in a subject, the method comprising:
  a) assaying a sample obtained from said subject for biomarkers of a panel as defined herein;
  b) measuring in said sample a concentration or an amount of each of the biomarkers of said panel;
  c) determining the stage of the neurocognitive disorder in said subject by comparing said concentration or amount of each of the biomarkers of the panel in said sample with reference concentrations or amounts of said biomarkers;
wherein the panel of biomarkers is selected from a panel comprising:
I)
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform a variant or a fragment thereof; or
II) one or more biomarkers selected from Groups A, B, C or D; or
III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or
IV) one or more, optionally two or more proteins selected from Tables 5, 6, 7, 8, 9, 10, 11, 12, 13 or combinations thereof; or
V) combinations of I), II), III) and IV.

Preferably, in the staging method according to the invention, the levels of protein phosphatase 1 regulatory subunit 14A are increased in said sample of a subject with an advanced stage of the neurocognitive disorder; and/or the levels of 2',3'-cyclic-nucleotide 3'-phosphodiesterase are increased in said sample of a subject with an advanced stage of the neurocognitive disorder. In one embodiment, the staging of the neurocognitive disorder is higher (i.e. more advanced stage) the higher the tau expression and hyperphosphorylation. Hence, the stage is tau-dependent.

Preferably, the neurocognitive disorder is characterized by tau-toxicity and more preferably the neurocognitive disorder is a tauopathy selected from the group of Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, chronic traumatic encephalopathy, alpha-synucleinopathies, Parkinson's disease or combinations thereof.

Even more preferably the tauopathy is Alzheimer's disease (AD) and the staging is any one of the stages of Braak staging of AD.

Braak staging for AD was firstly described in 1991 (Braak, H. et al. (1991) Acta Neuropathologica 82 (4): 239-59) and comprises:
- stages I and II: used when neurofibrillary tangle involvement is confined mainly to the transentorhinal region of the brain;
- stages III and IV when there is also involvement of limbic regions such as the hippocampus, and
- stages V and VI when there is extensive neocortical involvement In one preferred embodiment, when the the neurocognitive disorder is AD, the concentration or amount of protein phosphatase 1 regulatory subunit 14A comprising or having the amino acid sequence of SEQ ID NO:1 or an isoform or a variant or a fragment thereof is increased in the sample of AD patients with AD Braak stage V or Braak stage VI with respect to AD patients with AD Braak stage III or stage IV.

In another preferred embodiment, when the the neurocognitive disorder is AD, the concentration or amount of 2',3'-cyclic-nucleotide 3'-phosphodiesterase comprising or having the amino acid sequence of SEQ ID NO:2 or an isoform or a variant or a fragment thereof is increased in the sample of AD patients with AD Braak stage V or Braak stage VI with respect to AD patients with AD Braak stage III or stage IV.

The invention also provides a method for assessing in a subject the likelihood of developing a neurocognitive disorder, the method comprising:
a) assaying a sample obtained from said subject for biomarkers of a panel as defined herein;
b) measuring in said sample a concentration or an amount of each of the biomarkers of said panel;
c) determining whether that subject is likely to develop a neurocognitive disorder by comparing said concentration or amount of each of the biomarkers of the biomarker panel in said sample with reference concentrations or amounts of said biomarkers;
wherein the panel of biomarkers is selected from a panel comprising:
I)
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform a variant or a fragment thereof; or
II) one or more biomarkers selected from Groups A, B, C or D; or
III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or
IV) one or more, optionally two or more proteins selected from Tables 5, 6, 7, 8, 9, 10, 11, 12, 13 or combinations thereof; or
V) combinations of I), II), III) and IV.

Preferably, the neurocognitive disorder is characterized by tau-toxicity and more preferably the neurocognitive disorder is a tauopathy selected from the group of Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, chronic traumatic encephalopathy, alpha-synucleinopathies, Parkinson's disease or combinations thereof.

Even more preferably the tauopathy is Alzheimer's disease.

The present invention also provides for a method for treating a neurocognitive disorder in a subject, the method comprising:
a) assaying a sample obtained from said subject for biomarkers of a panel as defined herein;
b) measuring in said sample a concentration or an amount of each of the biomarkers of said panel;
c) determining whether that subject has a neurocognitive disorder by comparing said concentration or amount of each of the biomarkers in said sample with reference concentrations or amounts of said biomarkers;
d) administering to said subject a drug for treating the neurocognitive disorder;
wherein the panel of biomarkers is selected from a panel comprising:
I)
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform a variant or a fragment thereof; or
II) one or more biomarkers selected from Groups A, B, C or D; or
III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or IV) one or more, optionally two or more proteins selected from Tables 5, 6, 7, 8, 9, 10, 11, 12, 13 or combinations thereof; or V) combinations of I), II), III) and IV.

Alternatively, this aspect may be formulated as a drug for use in the treatment of a neurocognitive disorder in a subject, wherein the subject is selected by the method comprising:
- a) assaying a sample obtained from said subject for the biomarkers of the panel as defined in any one of the first, second and third aspect of the invention, including the embodiments thereof;
- b) measuring in said sample a concentration or an amount of each of the biomarkers of said panel;
- c) determining whether that subject has a neurocognitive disorder by comparing said concentration or amount of each of the biomarkers in said sample with reference concentrations or amounts of said biomarkers; wherein the panel of biomarkers is selected from a panel comprising:

I)
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform a variant or a fragment thereof; or II) one or more biomarkers selected from Groups A, B, C or D; or III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or IV) one or more, optionally two or more proteins selected from Tables 5, 6, 7, 8, 9, 10, 11, 12, 13 or combinations thereof; or V) combinations of I), II), III) and IV.

or, alternatively, as a use of a drug for the manufacture of a medicament for the treatment of a neurocognitive disorder in a subject, wherein the subject is selected by the method comprising:
- a) assaying a sample obtained from said subject for the biomarkers of the panel as defined in any one of the first, second and third aspect of the invention, including the embodiments thereof;
- b) measuring in said sample a concentration or an amount of each of the biomarkers of said panel;
- c) determining whether that subject has a neurocognitive disorder by comparing said concentration or amount of each of the biomarkers in said sample with reference concentrations or amounts of said biomarkers; wherein the panel of biomarkers is selected from a panel comprising:

I)
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform a variant or a fragment thereof; or II) one or more biomarkers selected from Groups A, B, C or D; or III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or IV) one or more, optionally two or more proteins selected from Tables 5, 6, 7, 8, 9, 10, 11, 12, 13 or combinations thereof; or V) combinations of I), II), III) and IV.

In one embodiment, when the sample is a brain sample, the concentration or amount of protein phosphatase 1 regulatory subunit 14A comprising or having the amino acid sequence of SEQ ID NO:1 or an isoform or a variant or a fragment thereof; and/or 2',3'-cyclic-nucleotide 3'-phosphodiesterase comprising or having the amino acid sequence of SEQ ID NO:2 or an isoform or a variant or a fragment thereof will decrease in response to the administration of the drug for treating the neurocognitive disorder.

In another embodiment, when the sample is CSF, the concentration or amount of protein phosphatase 1 regulatory subunit 14A comprising or having the amino acid sequence of SEQ ID NO:1 or an isoform or a variant or a fragment thereof; and/or 2',3'-cyclic-nucleotide 3'-phosphodiesterase comprising or having the amino acid sequence of SEQ ID NO:2 or an isoform or a variant or a fragment thereof increase or decrease in response to the treatment.

The present invention also provide for a method for assessing the response to a drug for treating a neurocognitive disorder in a subject, wherein the subject has been treated or is being treated with said drug, the method comprises:
- a) assaying a sample obtained from said subject for biomarkers of a panel as described herein;
- b) measuring in said sample a concentration or an amount of each of the biomarkers of said biomarker panel;
- c) determining whether said treatment for Alzheimer's disease is successful by comparing said concentration or amount of each of the biomarkers of the panel in said sample with reference concentrations or amounts of said biomarkers, wherein the panel of biomarkers is selected from a panel comprising:

I)
  i) protein phosphatase 1 regulatory subunit 14A comprising or having the amino acid sequence of SEQ ID NO:1 or an isoform or a variant or a fragment thereof;

and/or
ii) 2',3'-cyclic-nucleotide 3'-phosphodiesterase comprising or having the amino acid sequence of SEQ ID NO:2 or an isoform a variant or a fragment thereof; or
II) one or more biomarkers selected from Groups A, B, C or D; or
III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or
IV) one or more, optionally two or more proteins selected from Tables 5, 6, 7, 8, 9, 10, 11, 12, 13 or combinations thereof; or
V) combinations of I), II), III) and IV.

Preferably, the neurocognitive disorder in these two aspects of the invention is characterized by tau-toxicity and more preferably the neurocognitive disorder is a tauopathy selected from the group of Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, chronic traumatic encephalopathy, alpha-synucleinopathies, Parkinson's disease or combinations thereof.

In one preferred embodiment the tauopathy is Alzheimer's disease.

In one embodiment, the drug for treating the neurocognitive disorder is a kinase inhibitor; preferably the kinase inhibitor is selected from a tau kinase inhibitor or a casein kinase inhibitor, more preferably a casein kinase 1 alpha, beta, gamma, delta or epsilon.

Even more preferably, the kinase inhibitor is a casein kinase 1 delta inhibitor. Casein kinase 1 delta inhibitors are described in WO2012080727 and WO2012080729 which are incorporated herein as reference.

Examples of casein kinase 1 delta inhibitors are 5-(1,3-benzoxazol-2-yl)-4-(pyridin-4-yl)pyrimidin-2-amine (PS-110); 2-amino-3-[(thiophen-2-yl)carbonyl]indolizine-1-carboxamide; 2-[3-(pyridin-4-yl)-1H-pyrazol-4-yl]-1,3-benzoxazole; 2-amino-3-[(4-fluorophenyl)carbonyl]indolizine-1-carboxamide (PS278); 2-Methyl-amino-3-[(4-fluorophenyl)carbonyl]indolizine-1-carboxamide 2-amino-3-benzoyl-indolizine-1-carboxamide; 2-amino-1-[(4-fluorophenyl)carbonyl]-1H-indole-3-carboxamide; combinations thereof; or pharmaceutically acceptable salt or solvate thereof.

The most preferred casein kinase 1 delta inhibitor is selected from 5-(1,3-benzoxazol-2-yl)-4-(pyridin-4-yl)pyrimidin-2-amine (PS110); 2-amino-3-[(4-fluorophenyl)carbonyl]indolizine-1-carboxamide (PS278); 2-Methyl-amino-3-[(4-fluorophenyl)carbonyl]indolizine-1-carboxamide; combinations thereof; or pharmaceutically acceptable salt or solvate thereof.

Preferably, step d) in the method of treatment according to the invention further comprises administering an additional therapeutic agent. In one embodiment, the subject has been treated or is being treated with a kinase inhibitor and the additional therapeutic agent is selected from the group of memantine (e.g. Namenda®), galantamine (e.g. Razadyne®), rivastigmine (e.g. Exelon®), donepezil (e.g. Aricept®), solanezumab, 5HT5 antagonists or combinations thereof. In another embodiment, the subject has been treated or is being treated with an agent selected from the group of memantine (e.g. Namenda®), galantamine (e.g. Razadyne®), rivastigmine (e.g. Exelon®), donepezil (e.g. Aricept®), solanezumab, 5HT5 antagonists or combinations thereof and the additional therapeutic agent is selected from a kinase inhibitor, preferably a casein kinase 1 delta inhibitor, more preferably a casein kinase inhibitor selected from 5-(1,3-benzoxazol-2-yl)-4-(pyridin-4-yl)pyrimidin-2-amine; 2-amino-3-[(4-fluorophenyl)carbonyl]indolizine-1-carboxamide; 2-Methyl-amino-3-[(4-fluorophenyl)carbonyl]indolizine-1-carboxamide; combinations thereof; or pharmaceutically acceptable salt or solvate thereof.

In one embodiment of the invention, when assessing the response to a drug for treating a neurocognitive disorder in a subject, wherein the subject has been treated or is being treated with said drug:
  i) said subject has also been treated or is also being treated with an additional therapeutic agent selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof; and/or
  ii) after step c), the method comprises administering an additional therapeutic agent selected from the group of memantine (e.g. Namenda®), galantamine (e.g. Razadyne®), rivastigmine (e.g. Exelon®), donepezil (e.g. Aricept®), solanezumab, $5HT_5$ antagonists or combinations thereof.

The assaying step a) and/or the measuring step b) of all the methods according to the present invention may further comprise:
  i) contacting said sample with one or more binding agents to each of said biomarkers of the panel; or
  ii) detecting in said sample autoantibodies specific to each of said biomarkers; or
  iii) detecting in said sample by mass spectrometry each of said biomarkers of the panel, optionally by previously labelling said sample with one or more isobaric reactive mass labels; or
  iv) detecting in said sample by 2D gel electrophoresis each of said biomarkers of the panel; or
  iv) any combinations of i), ii), iii) or iv).

Preferably, the assaying in step a) and/or the measuring in step b) comprise:
  i) detecting one or more fragments of said biomarkers in the panel and/or
  ii) detecting one or more phosphorylated amino acids on tau comprising or having the amino acid sequence of SEQ ID NO: 29 or one or more fragments thereof; wherein when the phosphorylated amino acid on tau to be detected is T181, at least one more phosphorylated amino acid on tau or one or more fragments thereof is detected.

Optionally, the sample is immobilised on a solid support.

The sample to be assayed in the methods according to the present invention is selected from the group of cerebrospinal fluid (CSF), blood, plasma, serum, saliva, urine, tissue (e.g. brain tissue) or combinations thereof.

Preferably the sample is CSF or blood.

The subject to be diagnosed or assessed or treated may be an animal model (e.g. a rodent or a primate) of AD or of a tauopathy as described herein or a human subject. Preferably, the subject to be diagnosed, assessed or treated is a human subject.

2. Kits

The present invention also provides for kits comprising reagents for assaying and/or measuring in a sample the biomarkers of the panels according to the present invention.

Preferably, the kit allows the diagnosing, staging and assessment of response to a treatment for neurocognitive disorders, in particular Alzheimer's disease.

The reagents of the kits according to the invention may comprise one or more binding agents which specifically bind to the biomarkers of the panels described herein. Preferably, the one or more binding agents are primary antibodies, wherein each primary antibody specifically binds to:
  i) a different protein of the panel and/or
  ii) one or more phosphorylated amino acids of tau comprising or having amino acid sequence of SEQ ID NO: 29 or fragments thereof.

More preferably, the primary antibodies are one or more antibodies against protein phosphatase 1 regulatory subunit 14A and/or one or more antibodies against 2',3'-cyclic-nucleotide 3'-phosphodiesterase. Other primary antibodies include antibodies against the other biomarkers of Groups A, B, C or D and of the proteins listed in Tables 5 to 13.

The primary antibodies may be immobilised on an assay plate, beads, microspheres or particles. Optionally, beads, microspheres or particles may be dyed, tagged or labelled. Optionally the assay plate is a planar array or microtitre multi-well plate.

When the kits comprise primary antibodies against the biomarkers of the panel, the kits may further comprise one or more secondary antibodies which specifically bind to said primary antibodies.

Optionally, the secondary antibodies may be labelled for example fluorescent labelled or tagged.

The kits according to the invention may further comprise one or more detection reagents for detecting the presence of the tagged secondary antibodies.

The sample is preferably selected from the group of cerebrospinal fluid (CSF), blood, plasma, serum, saliva, urine, tissue (e.g. brain tissue) or combinations thereof.

The kits of the invention allow to:
  a) assay a sample obtained from a subject for biomarkers of a panel;
  b) measure in said sample a concentration or an amount of each of the biomarkers of said panel;
  c) determine whether that subject has a neurocognitive disorder, in particular Alzheimer's disease, by comparing said concentration or amount of each of the protein in said sample to reference concentrations or amounts of said proteins;
wherein the panel of biomarkers is selected from a panel comprising:

I)
  i) protein phosphatase 1 regulatory subunit 14A comprising or having the amino acid sequence of SEQ ID NO:1 or an isoform or a variant or a fragment thereof; and/or
  ii) 2',3'-cyclic-nucleotide 3'-phosphodiesterase comprising or having the amino acid sequence of SEQ ID NO:2 or an isoform a variant or a fragment thereof; or
II) one or more biomarkers selected from Groups A, B, C or D; or
III) tau or one or more fragments thereof, wherein tau:
  i) comprises or has the amino acid sequence of SEQ ID NO:29 and
  ii) comprises one or more, optionally two or more phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422; wherein when the phosphorylated amino acid on tau is T181, the panel comprises tau or one or more fragments thereof having at least one more phosphorylated amino acid; or
IV) one or more, optionally two or more proteins selected from Tables 5, 6, 7, 8, 9, 10, 11, 12, 13 or combinations thereof; or
V) combinations of I), II), III) and IV.

In particular, the kits according to the invention may instruct to assay (as in step a)) and/or to measure (as in step b)) the sample by:
  i) contacting said sample with one or more binding agents to each of said biomarkers of the panel; or
  ii) detecting in said sample autoantibodies specific to each of said biomarkers; or
  iii) detecting in said sample by mass spectrometry each of said biomarkers of the panel, optionally by previously labelling said sample with one or more isobaric reactive mass labels; or
  iv) detecting in said sample by 2D gel electrophoresis each of said proteins of the panel; or
  iv) any combinations of i), ii), iii) or iv).

In yet another embodiment, the kits may comprise reagents suitable for preparing brain tissue, optionally for preparing formalin-fixed paraffin-embedded brain tissue sections.

The kit may additionally provide a reference which provides a quantitative measure by which determination of a concentration or amount of one or more biomarkers can be compared. The reference may indicate the amount or concentration of proteins which indicate the presence or staging or likelihood of developing a neurocognitive disorder such as a tauopathy in particular AD.

The kit may also comprise printed instructions for performing the methods according to the present invention.

In one embodiment, the kit may be for performance of a mass spectrometry assay and may comprise a set of reference peptides (e.g. SRM peptides) in an assay compatible format wherein each peptide in the set is uniquely representative of i) one or more of the biomarkers of Groups A, B, C or D; ii) phosphorylated tau comprising or having the amino acid sequence of SEQ ID NO: 29 or one or more fragments thereof; or iii) one or more of the proteins listed in Tables 5 to 13.

Preferably two or more of such unique peptides are used for each biomarker for which the kit is designed, and wherein each set of unique peptides are provided in known amounts which reflect the amount or concentration of such biomarker in a sample of a healthy subject.

Optionally, the kit may also provide protocols and reagents for the isolation and extraction of the biomarkers according to the invention from a sample, a purified preparation of a proteolytic enzyme such as trypsin and a detailed protocol of the method including details of the precursor mass and specific transitions to be monitored. The peptides may be synthetic peptides and may comprise one or more heavy isotopes of carbon, nitrogen, oxygen and/or hydrogen.

Optionally, the kits of the present invention may also comprise appropriate cells, vessels, growth media and buffers.

3. Detection and Measurement of Biomarkers

The panel of biomarkers described herein comprise both biomarkers where expression is modulated, i.e. quantitatively increased or decreased, and biomarkers which are exclusively present or absent, i.e. qualitatively expressed, in normal versus disease states. The degree to which expression differs in normal versus disease states need only be large enough to be visualised via standard characterisation techniques.

Methods for the detection and quantification of proteins are well known in the art and any suitable method may be employed.

In one embodiment, the biomarkers of the panel may be detected using a binding agent, such as an antibody, specific to that biomarker, for example in an ELISA assay or Western blotting.

Methods relating to the production of antibodies capable of specifically recognising one or more epitopes, including phosphorylated amino acids or amino acids carrying other post-translational modifications, of the individual biomarker in the panel described herein are known in the art. Such antibodies may include, but are not limited to, polyclonal antibodies, monoclonal antibodies (mAbs), humanised or chimeric antibodies, single chain antibodies, Fab fragments, F(ab')2 fragments, fragments produced by a Fab expression library, anti-idiotypic (anti-Id) antibodies, and epitope-binding fragments of any of the above.

For the production of antibodies, various host animals may be immunised by injection with a protein, or a portion thereof. Such host animals may include, but are not limited to, rabbits, mice and rats. Various adjuvants may be used to increase the immunological response, depending on the host species, including active substances such as lysolecithin, Pluronic polyols, polyanions, peptides, oil emulsions, keyhole limpet hemocyamin, dinitrophenol, and potentially useful human adjuvant such as BCG bacille Calmette-Fuerin) and *Corynebacterium parvum.*

Polyclonal antibodies are heterogeneous populations of antibody molecules derived from the sera of animals immunised with an antigen, such as target proteins, or an antigenic functional derivative thereof. For the production of polyclonal antibodies, host animals such as those described above, may be immunised by injection with differentially expressed or pathway protein supplemented with adjuvants as also described above. Monoclonal antibodies, which are homogeneous populations of antibodies to a particular antigen, may be obtained by any technique, which provides for the production of antibody molecules by continuous cell lines in culture. These include, but are not limited to, the hybridoma technique of Kohler and Milstein (1975, Nature 256; 495-497; and U.S. Pat. No. 4,376,110), the human β-cell hybridoma technique (Kosbor, et al., 1983, Immunology Today 4: 72; Cole, et al., 1983, Proc. Natl. Acad. Sci. USA 80; 2026-2030), and the EBV-hybridoma technique (Cole, et al., 1985, Monoclonal Antibodies and Cancer Therapy, Alan R. Liss Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of 'chimeric antibodies' (Morrison, et al., 1984, Proc. Natl. Acad. Sci. 81: 6851-6855; Neuberger, et al., 1984, Nature 312: 604-608; Takeda, et al., 1985, Nature 314: 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242: 423-426; Huston, et al., 1988, Proc. Natl. Acad. Sci. USA 85: 5879-5883; and Ward, et al., 1989, Nature 334: 544-546) can be adapted to produce differentially expressed or pathway protein-single chain antibodies. Single chain antibodies are formed by linking the heavy and light chain fragments of the Fv region via an amino acid bridge, resulting in a single chain polypeptide.

Antibody fragments, which recognise specific epitopes, may be generated by known techniques. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternative, Fab expression libraries may be constructed (Huse, et al., 1989, Science 246: 1275-1281) to allow rapid and easy identification of monoclonal Fab fragments with the desired specificity.

In some embodiments of the methods described herein, the sample may be immobilised on a solid support for analysis. An antibody sandwich technique may be employed in which binding agents, such as antibodies, specific for the individual protein of the panel are immobilized on a solid support such as a planar surface or a microparticle bead and proteins of the panel are captured by the immobilised binding agents, such as immobilized antibodies. The captured proteins are then detected using a second binding agent, such as a secondary antibody, that may be directly labelled with a signal generating agent (enzyme, fluorescent tag, radiolabel etc.) or may be detected using further amplification (labelled secondary antibody, streptavidin/biotin systems with enzyme, fluorophore, radiolabel etc.). Other methods may include, but are not limited to, one-dimensional or two-dimensional (2D) gel electrophoresis of samples. Such methods are followed by transfer to a solid surface using techniques such as Western blotting and subsequent detection using antibodies specific for the proteins of the panel.

In other embodiments, autoantibodies to the biomarkers of the panel may be detected using the Western blotting approach described above using samples from a healthy subject, a patient or representative of AD, and then detecting the presence of auto-antibodies specific for the biomarkers that are present in the sample, but not in healthy subjects.

An example of a non-antibody binding agent is an aptamer. Examples of aptamers include nucleic acid aptamers and peptide aptamers.

Alternatively, the biomarkers of the panel may be detected by, amongst others, silver staining of 2D gel electrophoresis or mass spectrometry techniques including LS/MS/MS, MALDI-TOF, SELDI-TOF and TMT-SRM.

Other such standard characterisation techniques by which expression differences may be visualised are well known to those skilled in the art. These include successive chromatographic separations of fractions and comparisons of the peaks, capillary electrophoresis, separations using micro-channel networks, including on a micro-chip, SELDI analysis and qPST analysis.

Chromatographic separations can be carried out by high performance liquid chromatography as described in literature, the chromatogram being obtained in the form of a plot of absorbance of light at 280 nm against time of separation. The material giving incompletely resolved peaks is then re-chromatographed and so on.

Capillary electrophoresis may also be employed. The technique depends on applying an electric potential across the sample contained in a small capillary tube. The tube has a charged surface, such as negatively charged silicate glass. Oppositely charged ions (in this instance, positive ions) are attracted to the surface and then migrate to the appropriate electrode of the same polarity as the surface (in this instance, the cathode). In this electro-osmotic flow (EOF) of the sample, the positive ions move fastest, followed by uncharged material and negatively charged ions. Thus, proteins are separated essentially according to charge on them.

Micro-channel networks function similarly to capillaries and can be formed by photoablation of a polymeric material. In this technique, a UV laser is used to generate high energy light pulses that are fired in bursts onto polymers having suitable UV absorption characteristics, for example polyethylene terephthalate or polycarbonate. The incident photons break chemical bonds with a confined space, leading to a rise in internal pressure, mini-explosions and ejection of the ablated material, leaving behind voids which form micro-channels. The micro-channel material achieves a separation based on EOF, as for capillary electrophoresis. It is adaptable to micro-chip form, each chip having its own sample injector, separation column and electrochemical detector.

Surface enhanced laser desorption ionisation time of flight mass spectrometry (SELDI-TOF-MS) combined with ProteinChip technology can also provide a rapid and sensitive means of profiling biomarkers and is used as an alternative to 2D gel electrophoresis in a complementary fashion. The ProteinChip system consists of aluminium chips to which protein samples can be selectively bound on the surface chemistry of the chip (eg. anionic, cationic, hydrophobic, hydrophilic etc). Bound biomarkers are then co-crystallised with a molar excess of small energy-absorbing molecules. The chip is then analysed by short intense pulses of $N_2$ 320 nm UV laser with protein separation and detection being by time of flight mass spectrometry. Spectral profiles of each group within an experiment are compared and any peaks of interest can be further analysed using techniques as described below to establish the identity of the protein of the panel.

Isotopic or isobaric Tandem Mass Tags® (TMT® Thermo Scientific, Rockford, USA) technology may also be used to detect proteins of the panel described herein. Briefly, the proteins in the samples for comparison are optionally digested, labelled with a stable isotope tag and quantified by mass spectrometry. In this way, expression of equivalent proteins in the different samples can be compared directly by comparing the intensities of their respective isotopic peaks or of reporter ions released from the TMT® reagents during fragmentation in a tandem mass spectrometry experiment.

Detection of the proteins of the panel described herein may be preceded by a depletion step to remove the most abundant proteins from the sample. The large majority of the protein composition of serum/plasma consists of just a few proteins. For example, albumin, which is present at a concentration of 35-50 mg/ml, represents approximately 54% of the total protein content with IgG adding other 16%. In contrast, proteins changing in response to disease, for example as a result of tissue leakage, may circulate at 10 ng/ml. This vast dynamic range of protein concentrations represents a major analytical challenge and to overcome the problem, a multiple affinity depletion column may be used to remove the most highly abundant proteins (e.g. the 2, 3, 4, 5, 6, 7, 8, 9 or 10 or more highly abundant proteins). This enables the detection of changes in lower abundance ranges because more starting material can be used and there is less interference from the highly abundant molecules. Such a depletion strategy can be applied before any detection method.

4. Examples

Certain aspects and embodiments of the invention will now be illustrated by way of example and with reference to the figures and tables described above. All documents mentioned in this specification are incorporated herein by reference in their entirety for all purposes.

All reagents for sample preparation were purchased from Sigma Aldrich® (Dorset, UK) unless stated. Tandem Mass Tags® (Thermo Scientific®); Acetonitrile (Fisher Scientific®, Loughborough, UK); Trypsin (Roche Diagnostics®, West Sussex, UK).

4.1 Proteins which Correlate with Neurofibrillary Tangle Pathology in the Brain (Braak Staging)

Samples Preparation

Nine frozen tissue samples from inferior temporal cortex samples were dissected from larger frozen tissue sections. Samples were selected according to neurofibrillary tangle (NFT) pathology (=Braak staging) and thus represent all the phases of the AD-related NFT pathology.

The study group comprised one sample each for Braak stage 0, I and II, one sample for Braak stage III, two samples with Braak stage IV, one sample for Braak stage V and a further two samples with Braak stage 6.

The samples were processed and analysed according to the SysQuant® technology as described in details herein below, within one SysQuant® TMT 10plex experiment, which included all nine samples and one study reference.

Quantitative considerations have been performed following a statistical evaluation by a principal component analysis (PCA) of the data, which showed most significant differences in samples with higher Braak staging. Consequently to the PCA results, regulations have been calculated and statistically evaluated by comparing samples with Braak stages V/VI (severe group) to samples with Braak stages III/IV (moderate group).

The cortex samples in lysis buffer (8 M urea, 75 mM NaCl, 50 mM Tris, pH 8.2, protease and phosphatase inhibitors cocktail (Roche) were lysed by sonication (20% Amplitude for 20×1 second, pulsing on and off, on ice (4° C.)) and then centrifuged at 12,500 g for 10 min at 4° C. to eliminate tissue debris. Supernatant was transferred into new tubes and the protein concentration of the samples determined using the Bradford assay. Per sample, the same protein amount was used for all subsequent steps.

After lysis, a reference sample was generated by mixing of identical amounts of all nine individual samples. In particular, for each sample 2.5 mg of protein material were taken and adjusted to a concentration of 3 mg/ml. From each adjusted sample, 167 µL were taken and combined to generate a reference sample. The remaining 666 µL (=2 mg) were used for individual sample manipulation.

DTT was added to each sample (final concentration 5 mM) and incubate for 25 min at 56° C. under shaking to reduce disulfide bonds. Samples were then allowed to cool at room temperature before adding iodoacetamide (final concentration 14 mM) and incubated for 30 min at room temperature and in the dark to alkylate cysteine residues. Unreacted iodoacetamide was quenched by adding DTT to additional 5 mM and incubating 15 min at room temperature in the dark.

Samples were diluted with 25 mM Tris-HCl, pH 8.2, to reduce the concentration of urea to 1.6 M. Trypsin (Roche, UK) was added to a final minimum concentration of 5 ng/µL (trypsin to substrate ratio of at least 1:100) together with $CaCl_2$ (final concentration of 1 mM). Samples were incubated at 37° C. overnight with shaking (~15-18 hours). Digested samples were allowed to cool to room temperature and digestion was stopped by acidification with TFA to 0.4% (vol/vol). Samples were centrifuged at 2,500 g for 10 min at room temperature and the pellet was discarded.

Samples were desalted using a 200 mg SepPak tC18 cartridges (Thermo Scientific UK) according to manufacturer's instructions and proteins were eluted with elution buffer (50% ACN, 50% H2O) and concentrated to dryness in Speedvac.

For TMT® labelling samples were re-solubilised into 567 µL of TEAB/ACN buffer for a final concentration of 2.0-2.5 mg total peptide amount per sample. TMT® labels from the TMT® 10plex regent set was added to each sample according to Table 14 below to give a final concentration of 15 mM TMT® in each sample.

TABLE 14

| Sample No. | Braak staging | TMT ® labelling |
|---|---|---|
| 1 | V | TMT$^6$-126 |
| 2 | IV | TMT$^6$-128 |
| 3 | VI | TMT$^6$-129e |
| 4 | I | TMT$^6$-127 |
| 5 | VI | TMT$^6$-130 |
| 6 | 0 | TMT$^6$-128e |
| 7 | II | TMT$^6$-129 |
| 8 | IV | TMT$^6$-127e |
| 9 | III | TMT$^6$-130e |
| Ref. | N/A | TMT$^6$-131 |

Ref. = Reference sample containing an aliquot of all the samples

Reaction were allowed to take place for 1 hr at room temperature. Hydroxylamine was added to each sample to a final concentration of 0.25% [w/v] hydroxylamine and incubated for 15 minutes. Samples were then diluted 1:3 with 2% TFA and then further diluted with water to reduce the concentration of ACN to below 5%. Samples were mixed in equal amounts to achieve one SysQuant10plex sample which was then split into two aliquots which were desalted (500 mg SepPak tC18 cartridges) and fractionated by SCX chromatography (3 mL/min as flow rate; Buffer A: Water+ 0.1% TFA; Buffer C: 7 mM KH2PO4, pH 2.65, 30% ACN (vol/vol); Buffer D: 7 mM KH2PO4, 350 mM KCl, pH 2.65, 30% ACN (vol/vol)) according to the protocol in Table 15.

TABLE 15

| Time [min] | Buffer A [%] | Buffer C [%] | Buffer D [%] |
|---|---|---|---|
| 0 | 0 | 100 | 0 |
| 2 | 0 | 100 | 0 |
| 35 | 0 | 75 | 25 |
| 36 | 0 | 0 | 100 |
| 46 | 0 | 0 | 100 |
| 47 | 100 | 0 | 0 |
| 57 | 100 | 0 | 0 |
| 58 | 0 | 100 | 0 |
| 67 | 0 | 100 | 0 |
| 68 | 0 | 100 | 0 |

Lyophilized peptides from desalting were re-suspended in 800 µL of buffer A, injected onto the HPLC system. Twelve fractions were collected and "smart pooled" by mixing fractions with low numbers of peptides with fractions containing large numbers of peptides to provide 6 final fractions with similar total peptide content and desalted.

Then, small portions were taken from each fraction to apply the subsequent analysis of non-enriched fractions. The remaining portion of the fractions were applied to enrichment for phosphopeptides by either the IMAC or the $TiO_2$ procedures, both well-known in the art. Dried fractions were transferred for LC-MS analysis LC-MS/MS Analysis "Smart-pooled" fractions were analysed twice each by LC-MS/MS (double-shot workflow), with MS acquisition performed by Top Speed MS2 HCD method.

Peptides from non-enriched fractions were re-suspended in 100 µl 2% ACN/0.1% FA, then 5 µl per fraction was injected onto a 2 cm×75 µm Acclaim PepMap100 pre-column, and separated using an EASY-Spray 50 cm×75 µm ID, PepMap RSCL, C18, 2 µm, on the EASY-nLC 1000 system (Thermo Fisher Scientific). Peptides were resolved using a 160 min separation gradient of 8 to 30% ACN/0.1% FA at 200 nL/min.

Peptides from all phospho-enriched fractions were re-suspended in 30 µl of 2% ACN/0.1% FA, then 5 µL per fraction injected and resolved using a 160 min separation gradient of 10 to 30% 0.1% FA in ACN at 200 nL/min.

Mass spectra were acquired on an Orbitrap Fusion™ Tribrid™ Mass Spectrometer (Thermo Fisher Scientific) for a total run time of 180 min using top speed higher collision induced dissociation (HCD) FTMS2 scans at 30,000 resolving power, following each FTMS scan (120,000 resolving power). HCD was carried out on the most intense ions from each FTMS scan, and then put on a dynamic exclusion list for 30 sec to avoid repeated sequencing of the same analyte. Each sample was analysed by two LC-MS/MS analytical repeats (double shot workflow).

Computational MS

The acquired spectra were processed using Proteome Discoverer 1.4 (PD 1.4; Thermo Fisher Scientific) software using the human specific UniProtKB/Swiss-Prot database (88,647 sequence entries) downloaded on 22 Feb. 2014. The raw data was searched using the Sequest HT and Mascot (Matrix Mascot server 2.2.06) search algorithms within PD 1.4. MS raw data files that belonged to the 6 fractions of any enrichment arm of the SysQuant® workflow and those which belonged to the same analytical set of runs were submitted as an individual MudPit search each. Thus, in total four MudPit searches were performed. After filtering the search results at 1% false discovery rate (FDR) at the peptide level and at least one rank 1 peptide per protein, search results were exported to MS Excel files. This data was processed by defined scripts to list all identified peptides, and their protein origin.

Data Analysis

All protein identification, peptide sequence, phosphorylation site information along with quantitative values and biological information relating to the peptide, protein and phosphorylation sites were assembled in a Microsoft Excel file (QuantSheet) to allow structured data analysis based on fold-change, significance, biological function and cellular localisation.

To evaluate the general data quality by bioinformatic means, i.e. to visualize the effect of Braak staging, and thus to guide subsequent quantitative computations, a principle component analysis (PCA) was carried out.

A thorough biological data interpretation was also performed and a targeted analysis of proteins of interest was applied, for example for tau protein and additional AD biomarkers Proteins implicated in neurodegeneration.

4.2 Quantification of Regulated Proteins in AD CSF Using TMTcalibrator™

Figure 7:
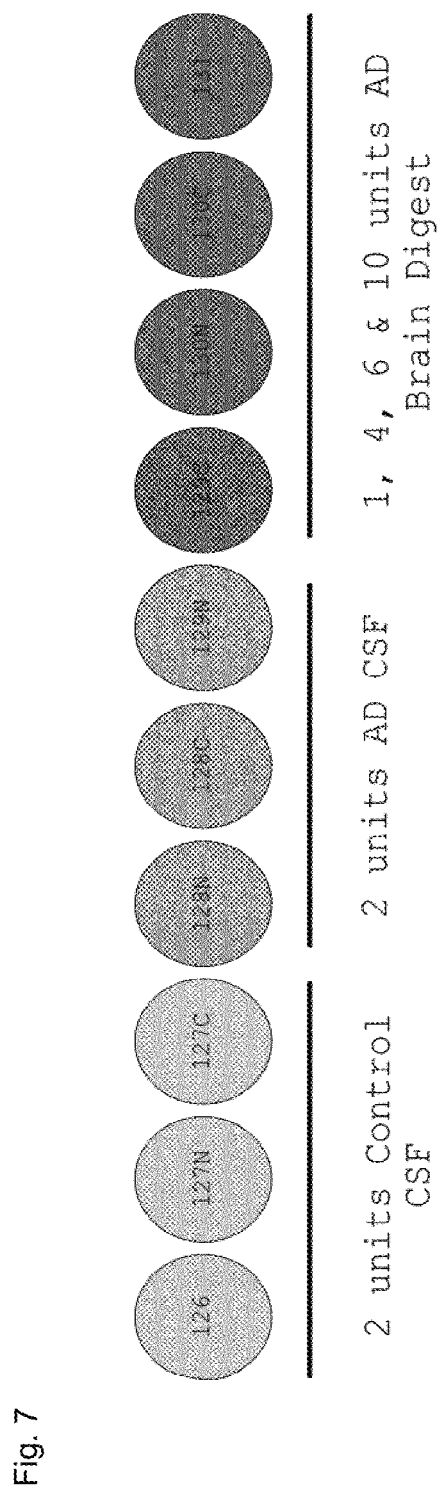
FIG. 7. Experimental design of TMTcalibrator™ experiments to measure brain derived proteins in CSF of human control and biochemically diagnosed AD subjects.

We also identified the presence and relative abundance of phosphorylated peptides of tau in human CSF drawn from controls that were biochemically negative for AD and those that were biochemically positive. Briefly, post-mortem collected pre-frontal cortex material from human subjects with moderate tau pathology (Braak stages III-IV; n=3) or severe tau pathology (Braak stages V-VI; n=3), performed in separate experiments, were pooled, digested with trypsin and labelled in four separate aliquots with TMT reagents TMT[10]-129C, 130N, 130C and 131. Each labelled aliquot from the same brain digest pool was mixed at a ratio of 0.3 mg:1.2 mg:1.8 mg:3.0 mg respectively to form a calibration standard. At the same time human cerebrospinal fluid samples (600 µg protein content (600 µl) per individual) from three non-cognitively impaired control individuals and three biochemically diagnosed cases of AD were digested with trypsin and labelled with TMT[10] reagents TMT[10]-126, 127N, 127C, 128N, 128C and 129N respectively and mixed to form the clinical test sample. Finally an equal volume of the calibration standard and clinical test sample were mixed to form the analytical sample according to FIG. 7.

Mass spectrometry and data analysis was carried out as described above in Section 4.1.

4.3 Effects of Tau Inhibition In Vivo

The inventors have also applied SysQuant to analyse protein and phosphorylation changes in the brains of TMHT (Thy-1 Mutated Human Tau) mice (developed by QPS® Austria, http://www.qps-austria.com) treated with small molecule inhibitors of the tau kinase Casein Kinase 1 delta (CK1d). Starting at 8.5 months (±2 weeks) of age, TMHT mice received CK1d inhibitors 2-Methyl-amino-3-[(4-fluorophenyl)carbonyl]indolizine-1-carboxamide (PS278-05), 5-(1,3-benzoxazol-2-yl)-4-(pyridine-4-yl)pyrimidin-2-amine (PS110), compound PF4800567 (3-[(3-Chlorophenoxy)methyl]-1-(tetrahydro-2H-pyran-4-yl)-1H-pyrazolo[3,4-d]pyrimidin-4-amine; Tocris®) or vehicle (0.5% w/v methylcellulose) for 8 weeks (54 applications) at a dosage of 30 mg/kg body weight, orally via gavage.

In total 48 animals were used and allocated to 4 treatment groups. Table 16 describes the animals, cohort and treatment group allocation, sex and age of the animals.

TABLE 16

| Cohort | Group | Treatment | Sex | Start Age [months] |
|---|---|---|---|---|
| I | A | Vehicle | m | 8.75 |
| I | A | Vehicle | f | 8.75 |
| I | A | Vehicle | f | 8.75 |
| I | A | Vehicle | f | 8.75 |
| I | A | Vehicle | m | 8.42 |
| I | A | Vehicle | m | 8.42 |
| I | B | Cmp A | m | 8.75 |
| I | B | Cmp A | m | 8.75 |
| I | B | Cmp A | f | 8.45 |
| I | B | Cmp A | f | 8.45 |
| I | B | Cmp A | m | 8.32 |
| I | C | Cmp 324 | f | 8.75 |
| I | C | Cmp 324 | f | 8.75 |
| I | C | Cmp 324 | m | 8.75 |
| I | C | Cmp 324 | m | 8.75 |
| I | C | Cmp 324 | f | 8.75 |
| I | C | Cmp 324 | m | 8.45 |
| I | D | PF4800567 | m | 8.75 |
| I | D | PF4800567 | f | 8.75 |
| I | D | PF4800567 | f | 8.75 |
| I | D | PF4800567 | f | 8.45 |
| *I | D | PF4800567 | m | 8.42 |
| I | D | PF4800567 | m | 8.32 |
| II | A | Vehicle | f | 8.65 |
| II | A | Vehicle | f | 8.65 |
| II | A | Vehicle | m | 8.55 |
| II | A | Vehicle | f | 8.52 |
| II | A | Vehicle | f | 8.35 |
| II | A | Vehicle | m | 8.19 |
| II | B | Cmp A | f | 8.55 |
| II | B | Cmp A | f | 8.55 |
| II | B | Cmp A | f | 8.52 |
| II | B | Cmp A | m | 8.19 |
| II | B | Cmp A | m | 8.19 |
| II | B | Cmp A | f | 8.35 |
| II | C | Cmp 324 | m | 8.02 |
| II | C | Cmp 324 | m | 8.02 |
| II | C | Cmp 324 | f | 8.65 |
| II | C | Cmp 324 | f | 8.65 |
| II | C | Cmp 324 | f | 8.35 |
| II | C | Cmp 324 | f | 8.52 |
| II | D | PF4800567 | f | 8.35 |
| II | D | PF4800567 | f | 8.55 |
| II | D | PF4800567 | f | 8.55 |
| II | D | PF4800567 | m | 8.35 |
| II | D | PF4800567 | m | 8.35 |
| II | D | PF4800567 | f | 8.19 |

Cmp 324 = 5-(1,3-benzoxazol-2-yl)-4-(pyridine-4-yl)pyrimidin-2-amine;
Cmp A = 2-Methyl-amino-3-[(4-fluorophenyl)carbonyl]indolizine-1-carboxamide;
f = female;
m = male Brain samples were collected within 10 minutes of euthanasia, washed in ice cold saline, transferred to a clean Eppendorf tube and immediately frozen in liquid nitrogen.

One hippocampus sample (left or right) from each of three animals in each of the vehicle, PS110 and PS278-05 groups were selected for analysis by SysQuant. A pool of all nine samples was also prepared as a reference channel. All TMT® labelling, mixing and mass spectrometry and bioinformatics studies were performed essentially as described in Section 4.1. For peptide and protein identification the UniProtKB mouse database was used, supplemented by inclusion of all human tau isoform entries.

All protein identification, peptide sequence, phosphorylation site information along with quantitative values and biological information relating to the peptide, protein and phosphorylation sites were assembled in a Microsoft Excel file (QuantSheet) to allow structured data analysis based on fold-change, significance, biological function and cellular localisation.

4.4 Detection of Phosphorylated Tau

The kinetic profile of tau phosphorylation in the various human and mouse samples studied in Sections 4.1, 4.2 and 4.3 was determined by a targeted data analysis of the respective QuantSheets. All peptides that matched the human MAPT (P10636; including P10636-8=SEQ ID NO:29) UniProt sequences were exported into a separate Microsoft Excel sheets.

Ion intensity values for each non-phosphorylated peptide were summed and the average calculated for each disease severity group (Braak Stage 0-II; Braak Stage III-IV; Braak Stage V-VI) to give a value for total tau expression. For each phosphorylated amino acid e.g. pT181, the ion intensity values of all peptides containing said phosphorylated amino acid were summed and the average calculated for each disease severity group (Braak Stage 0-II; Braak Stage III-IV; Braak Stage V-VI).

A total of 185 unique peptides from human tau were quantified in all nine brain samples with 35 high confidence (phosphoRS score>75%) phosphorylation sites. Of these, the levels of 74 peptides were significantly ($p<0.05$) regulated in the brains of patients with moderate (Braak stage III-IV) and severe (Braak stage V-VI) tau pathology Similarly, the expression levels of total tau and for each phosphorylated serine, threonine and tyrosine amino acid in mouse brains following treatment with vehicle control or the CK1d inhibitors PS278-05 and PS110 were calculated.

All peptides that matched the human MAPT (P10636; SEQ ID NO:29) UniProt sequence and/or the mouse MAPT (P10637) were exported into a separate Microsoft Excel sheet. Ion intensity values for each phosphopeptide were summed and the average calculated for each treatment group (Vehicle control, PS110, PS278-05). We quantified 124 unique peptides from human tau in all nine brain samples with 39 high confidence (phosphoRS score>75%) phosphorylation sites. Of these, the levels of 37 peptides were significantly ($p<0.05$) regulated in the hippocampi of mice treated with PS110 whilst 22 peptides were significantly ($p<0.05$) regulated in the hippocampi of mice treated with PS278-05.

Finally, the levels of total tau and for each phosphorylated serine, threonine and tyrosine amino acid in human CSF samples drawn from control and biochemically confirmed cases of AD were determined as above. All peptides that matched the human MAPT (P10636) UniProt sequence were exported into a separate Microsoft Excel sheet. Ion intensity values for each phosphopeptide were summed and the average calculated for each group (Control, AD). There were 65 quantified tau peptides in human CSF covering 27 high confidence phosphorylation sites.

In total, across the three studies we identified 44 unique phosphorylation sites on tau protein with 19 sites being quantified in all samples of human brain, mouse brain and human CSF. Table 4 collates all Tau phosphorylation sites identified by SysQuant® and TMTcalibrator™ in mouse and human brain tissue and human CSF. Amino acid numbering based on human 2N4R tau (Uniprot Accession Number P10636-8 with SEQ ID NO:29).

The method of measurement of these phosphorylated residues in tau protein are not intended to limit the invention. One or more of the sites may be measured using a binding agent such as an antibody or aptamer specific for the phosphorylated residue. However, for some sites the use of a binding agent will be less desirable due to the influence of adjacent phosphorylation on additional residues. One such case is the measurement of phosphorylated threonine 181 (2N4R tau numbering). Current diagnosis of AD is supported by the measurement of CSF levels of total tau and pT181 to yield a ratio. The larger the ratio the greater the probability that the patient has AD. In the present study we have identified that pT181 can be measured on two separate peptides in CSF. One is a singly phosphorylated peptide at threonine 181 whilst the other is triply phosphorylated at threonine 181, serine 184 and serine 185. It is probable that additional phosphorylation at S184 and S185 will interfere with the affinity of the binding agent reducing its ability to bind to the triply phosphorylated species and so under-representing the total amount of pT181 in CSF.

To overcome these limitations, phosphorylated tau is preferably measured using mass spectrometry. Any form of mass spectrometry capable of providing a relative or absolute quantification of each phosphorylation may be used. Such methods include but are not limited to data independent acquisition (DIA), data dependent acquisition (DDA), selected reaction monitoring (SRM), multiple reaction monitoring (MRM), or TMTcalibrator™. In each case a reference phosphopeptide that can be differentiated from the endogenous phosphotau peptide in the test sample using mass spectrometry is provided. The reference phosphopeptide may be provided from a biological sample and made distinct from endogenous phosphopeptides using an isotopic or isobaric mass tag. Alternatively the reference phosphopeptide may be generated from digestion of a recombinant tau protein manufactured using a synthetic lysine source that has several $H^2$, $C^{13}$, $N^{15}$, $O^{18}$ atomic substitutions to ensure each tryptic peptide will have a mass greater than the naturally occurring equivalent phosphopeptide of at least 1 Dalton, preferably more than 2 Daltons and most preferably more than 5 Daltons. Fully synthetic peptides manufactured by sequential amino acid addition may be used wherein one or more amino acids within the peptide sequence contains atomic substitutions with $H^2$, $C^{13}$, $N^{15}$, $O^{18}$ or other such appropriate stable heavy isotope.

Irrespective of the means of detection and quantification, assays intended for early diagnosis, prognosis of disease progression or monitoring of therapeutic effect may measure one, two or more different tau phosphopeptides.

4.5 Identification of Other Brain-Derived Proteins in Human CSF

In addition to identifying regulated peptides derived from tau protein, we also analysed the data from Example 4.2 to identify other disease-related proteins that are differentially expressed in human AD CSF. Briefly, the TMT® reporter ion intensities for all unmodified peptides matched to a unique UniProt accession number were summed and used to determine the relative expression of the relevant protein in human CSF. Based on the summed intensity values a log 2 ratio was calculated for each protein expression in control (n=3) and AD (n=3) groups. Statistical significance was calculated as a p-value based on the six independent protein quantification values using a two sample t-test. The resulting data matrix was exported to Microsoft Excel and filtered to select all proteins showing greater than 40% regulation ($-0.5 \leq \log 2 \geq 0.5$) and $p \leq 0.05$. This was performed for both TMTcalibrator™ experiments using brain calibrants with moderate and severe tau pathology. The list of regulated proteins including log 2 ratio and p-values is shown in Table 5.

Any of the proteins listed in Table 5 may be used as diagnostic and/or prognostic biomarkers of AD.

4.6 Results

The present inventors have surprisingly identified biomarkers which are highly regulated in the brain of patients with AD and/or which are present in the CSF and/or which are highly regulated in response to administration of casein kinase inhibitors. In addition, tau toxicity in the brain of the patients used in these experiments present elevated expression and hyperphosphorylation (tau toxicity).

Surprisingly, when the data were analysed with respect to Braak stages V or VI, protein phosphatase 1 regulatory subunit 14A resulted to be the most upregulated protein (FIG. 3). Interestingly, levels of this protein first fell between mild (Braak stage 0-II) and moderate (Braak stage III/IV) before rising significantly in severe disease. Treatment with both casein kinase 1 delta inhibitors 5-(1,3-benzoxazol-2-yl)-4-(pyridine-4-yl)pyrimidin-2-amine or 2-Methyl-amino-3-[(4-fluorophenyl)carbonyl]indolizine-1-carboxamide resulted in an up-regulation of protein phosphatase 1 regulatory subunit 14A, apparently counteracting the drop in expression levels seen in moderate tau pathology in humans). FIG. 3 shows a Venn diagram for the analyses performed on the brains of patients with AD (label "Human Brain"), CSF of patients with AD at Braak stage V or VI (label "Human CSF 5/6") and on the brains of mice treated with 5-(1,3-benzoxazol-2-yl)-4-(pyridine-4-yl)pyrimidin-2-amine (upper diagram) or 2-Methyl-amino-3-[(4-fluorophenyl)carbonyl]indolizine-1-carboxamide (lower diagram) (label "Mice ck1 inh."). The numbers in the brackets below each of the labels indicate the number of proteins identified. As it can be seen in FIG. 3, there is only one protein which is upregulated in all the samples and this protein is protein phosphatase 1 regulatory subunit 14A.

Even more surprisingly, when the data were analysed with respect to Braak stages V or VI, 2',3'-cyclic-nucleotide 3'-phosphodiesterase resulted to be the most upregulated protein (FIG. 4). Interestingly, levels of this protein first fell between mild (Braak stage 0-II) and moderate (Braak stage III/IV) before rising significantly in severe disease. Again, in the parallel study in the TMHT model of tauopathy the type of treatment did not play a significant role with both compounds increasing the expression of the protein. FIG. 4 shows a Venn diagram for the analyses performed on the brains of patients with AD (label "Human Brain"), CSF of patients with AD at Braak stage 3 or 4 (label "Human CSF 3/4) and on the brains of mice treated with 5-(1,3-benzoxazol-2-yl)-4-(pyridine-4-yl)pyrimidin-2-amine (upper diagram) or 2-Methyl-amino-3-[(4-fluorophenyl)carbonyl]indolizine-1-carboxamide (lower diagram) (label "Mice ck1 inh."). As it can be seen in FIG. 4, there is only one protein which is upregulated in all the samples and this protein is 2',3'-cyclic-nucleotide 3'-phosphodiesterase.

FIG. 5 shows a bar diagram (A) which depicts the levels of protein phosphatase 1 regulatory subunit 14A levels in human brain with mild (Braak 0-II) (n=3), moderate (Braak III/IV) or severe (Braak V/VI) tau pathology; the levels of protein phosphatase 1 regulatory subunit 14A are increased in the brain of human subjects with an advanced stage of the neurocognitive disorder (Braak V/VI). FIG. 5 diagram (B) shows that mouse brain from the TMHT model of human tauopathy treated orally with vehicle alone or vehicle including 30 mg/kg of casein kinase 1 delta inhibitors 5-(1,3-benzoxazol-2-yl)-4-(pyridin-4-yl)pyrimidin-2-amine and 2-Methyl-amino-3-[(4-fluorophenyl)carbonyl]indolizine-1-carboxamide responded to treatment altering the concentration or amount of protein phosphatase 1 regulatory subunit 14A. Finally, FIG. 5 diagram (C) shows that CSF from patients with biochemically diagnosed AD (n=3) have a decreased level of protein phosphatase 1 regulatory subunit 14A compared to cognitively affected non-AD controls (n=3).

Figure 6:
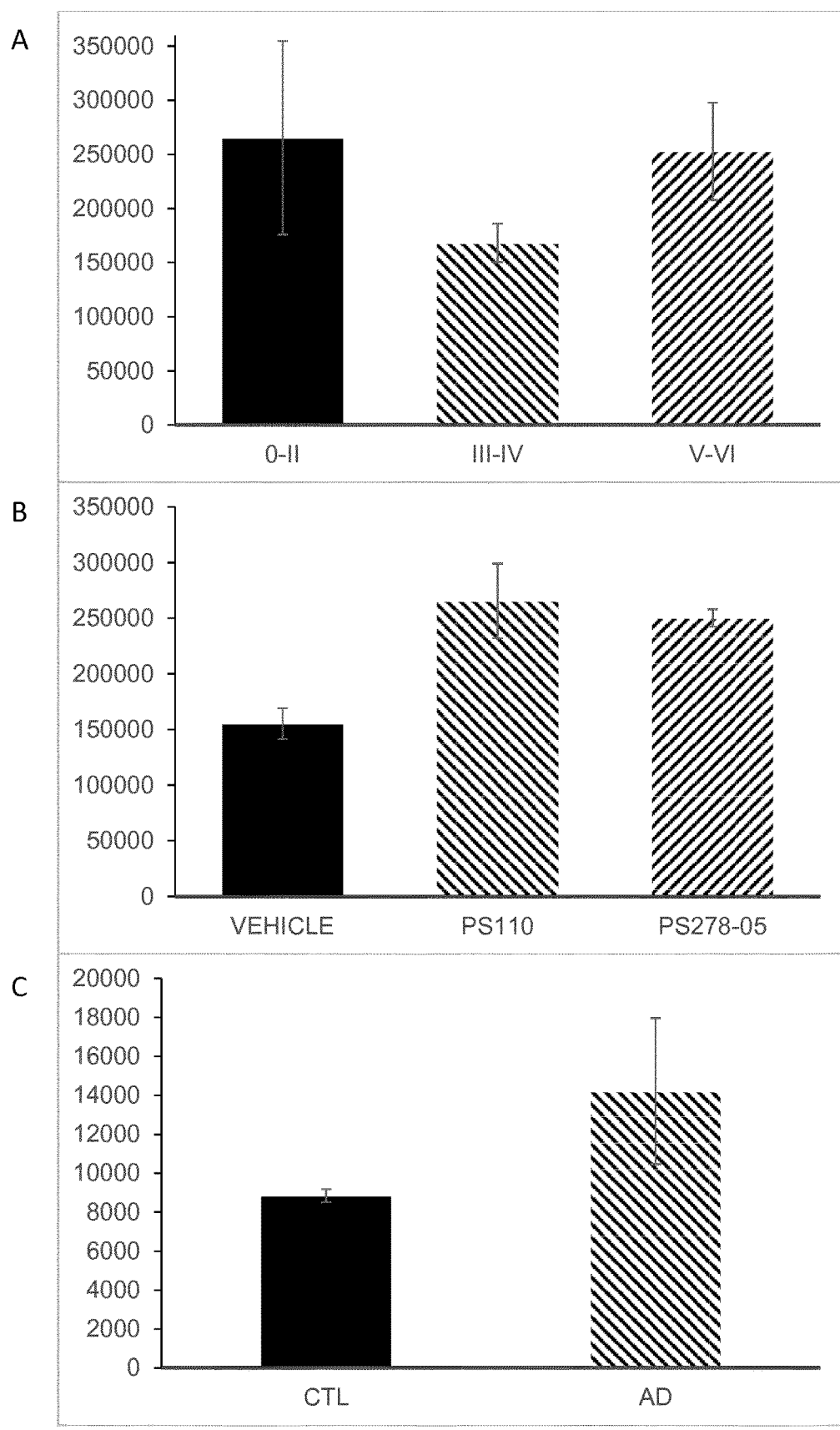
FIG. 6. Levels (as sums of ions intensities of all non-modified peptides) of 2',3'-cyclic-nucleotide 3'-phosphodiesterase in (A) Human brain with mild (Braak 0-II) (n=3), moderate (Braak III/IV) (n=3) or severe (Braak v/VI) (n=3) tau pathology; (B) Mouse brain from the TMHT model of human tauopathy treated orally with vehicle alone (n=3) or vehicle including 30 mg/kg of casein kinase 1 delta inhibitors 5-(1,3-benzoxazol-2-yl)-4-(pyridin-4-yl)pyrimidin-2-amine (PS110; n=3) and 2-Methyl-amino-3-[(4-fluorophenyl)carbonyl]indolizine-1-carboxamide (PS278-05; n=3); and (C) cerebrospinal fluid from cognitively affected non-AD controls (CTL; n=3) and patients with biochemically diagnosed AD (AD; n=3).

FIG. 6 shows a bar diagram (A) which depicts the levels of 2',3'-cyclic-nucleotide 3'-phosphodiesterase levels in human brain with mild (Braak 0-II) (n=3), moderate (Braak III/IV) or severe (Braak V/VI) tau pathology; the levels of 2',3'-cyclic-nucleotide 3'-phosphodiesterase are increased in the brain of human subjects with an advanced stage of the neurocognitive disorder (Braak V/VI). FIG. 6 diagram (B) shows that mouse brain from the TMHT model of human tauopathy treated orally with vehicle alone or vehicle including 30 mg/kg of casein kinase 1 delta inhibitors 5-(1,3-benzoxazol-2-yl)-4-(pyridin-4-yl)pyrimidin-2-amine and 2-Methyl-amino-3-[(4-fluorophenyl)carbonyl]indolizine-1-carboxamide responded to treatment altering the concentration or amount of protein 2',3'-cyclic-nucleotide 3'-phosphodiesterase. Finally, FIG. 6 diagram (C) shows that CSF from patients with biochemically diagnosed AD (n=3) have a increased level of 2',3'-cyclic-nucleotide 3'-phosphodiesterase compared to cognitively affected non-AD controls (n=3).

In summary, 1) both phosphatase 1 regulatory subunit 14A and 2',3'-cyclic-nucleotide 3'-phosphodiesterase are elevated in the brain of subjects with an advanced stage of a neurocognitive disorder (Braak stage V or stage VI); 2) in the CSF of AD subjects protein phosphatase 1 regulatory subunit 14A is decreased whilst 2',3'-cyclic-nucleotide 3'-phosphodiesterase is elevated in comparison to cognitively affected non-AD controls; and 3) both phosphatase 1 regulatory subunit 14A and 2',3'-cyclic-nucleotide 3'-phosphodiesterase are upregulated in response to casein kinase 1 delta inhibitors 5-(1,3-benzoxazol-2-yl)-4-(pyridin-4-yl)pyrimidin-2-amine and 2-Methyl-amino-3-[(4-fluorophenyl)carbonyl]indolizine-1-carboxamide.

Finally, additional proteins from Groups A, B, C, D and tables 5 to 13 can also be selected together with phosphatase 1 regulatory subunit 14A and 2',3'-cyclic-nucleotide 3'-phosphodiesterase to form enlarged biomarker panels for the diagnoses, staging and assessment of treatment of a neurocognitive disorder, in particular of AD.

The invention claimed is:

1. A kit for assaying and/or measuring two or more biomarkers in a sample comprising cerebrospinal fluid (CSF), blood, plasma, serum, saliva, urine, or tissue or a fraction thereof, obtained from a human subject, wherein the two or more biomarkers are selected from the group consisting of a tau protein, a protein phosphatase 1 regulatory subunit 14A, and/or a 2',3'-cyclic-nucleotide 3'-phosphodiesterase, said kit comprising:
 a first set of peptides comprising one or more fragments of a tau protein having the amino acid sequence of SEQ ID NO:29, in an assay-compatible format;
 a second set of peptides comprising one or more fragments of a protein phosphatase 11 regulatory subunit 14A having the amino acid sequence of SEQ ID NO:1, in an assay-compatible format; and/or
 a third set of peptides comprising one or more fragments of a 2',3'-cyclic-nucleotide 3'-phosphodiesterase having the amino acid sequence of SEQ ID NO:2, in an assay-compatible format;
 wherein the one or more fragments of SEQ ID NO:29, SEQ ID NO: 1 and SEQ ID NO: 2 are each at least 10 amino acids in length.

2. The kit of claim 1, wherein the tau protein comprises at least two phosphorylated amino acids selected from T39, S46, T50, T52, T56, S61, T63, S64, S68, T69, S113, T181, S184, S185, S191, S195, S198, S199, S202, S205, S208, S210, T212, S214, T217, T231, S235, S237, S238, S258, S262, S285, S289, S356, Y394, S396, S400, T403, S404, S409, S412, S413, T414/S416 or S422 of SEQ ID NO:29.

3. The kit of claim 1, wherein
 the first set of peptides comprises a plurality of fragments of the tau protein having the amino acid sequence of SEQ ID NO:29, each fragment having a different polypeptide sequence;
 the second set of peptides comprises a plurality of fragments of the protein phosphatase 1 regulatory subunit 14A having the amino acid sequence of SEQ ID NO: 1, each fragment having a different polypeptide sequence; and
 the third set of peptides comprises a plurality of fragments of the 2',3'-cyclic-nucleotide 3'-phosphodiesterase having the amino acid sequence of SEQ ID NO:2, each fragment having a different polypeptide sequence.

4. The kit of claim 1, wherein one or more of the peptides in the first, second, or third set of peptides, comprise at least one heavy isotope of carbon, nitrogen, oxygen and/or hydrogen.

5. The kit of claim 1, wherein the tau protein comprises one or more phosphorylated amino acids selected from S61, S64, T181, S184, S202, S205, T231 and/or S235 of SEQ ID NO:29.

6. The kit of claim 1, wherein the tau protein comprises one or more phosphorylated amino acids selected from S61, S64, S199, S205 and/or S396 of SEQ ID NO: 29.

7. The kit of claim 1, wherein the tau protein comprises a phosphorylated amino acid at S61 of SEQ ID NO:29.

8. The kit of claim 1, wherein the tau protein comprises a phosphorylated amino acid at S64 of SEQ ID NO:29.

9. The kit of claim 1, wherein the tau protein comprises a phosphorylated amino acid at S199 of SEQ ID NO:29.

10. The kit of claim 1, wherein the tau protein or fragment thereof comprises a phosphorylated amino acid at S205 of SEQ ID NO:29.

11. The kit of claim 1, wherein the tau protein comprises a phosphorylated amino acid at S396 of SEQ ID NO:29.

12. The kit of claim 1, wherein the tau protein comprises a phosphorylated amino acid at S61 and at least one of S64, S199, S205 or S396 of SEQ ID NO:29.

13. The kit of claim 1, wherein the tau protein comprises a phosphorylated amino acid at S199 and at least one of S205 or S396 of SEQ ID NO:29.

14. The kit of claim 1, wherein the tau protein comprises phosphorylated amino acids at S205 and S396 of SEQ ID NO:29.

15. The kit of claim 1, wherein the tau protein comprises phosphorylated amino acids at S61, S64 and at least one of S199, S205 or S396 of SEQ ID NO:29.

16. The kit of claim 1, wherein the kit comprises the first set of peptides, the second set of peptides, and the third set of peptides.

17. The kit of claim 1, wherein the kit comprises the first set of peptides, the second set of peptides, and the third set of peptides; and
 the first set of peptides consists of a plurality of fragments of the tau protein having the amino acid sequence of SEQ ID NO:29, wherein each fragment comprises at least 10 contiguous amino acids of the tau protein having the amino acid sequence of SEQ ID NO:29, and no two fragments have an identical amino acid sequence;
 the second set of peptides consists of a plurality of fragments of the protein phosphatase 1 regulatory subunit 14A having the amino acid sequence of SEQ ID NO:1, wherein each fragment comprises at least 10 contiguous amino acids of the protein phosphatase 1 regulatory subunit 14A having the amino acid sequence of SEQ ID NO:1, and no two fragments have an identical amino acid sequence; and the third set of peptides consists of a plurality of fragments of the 2',3'-cyclic-nucleotide 3'-phosphodiesterase having the amino acid sequence of SEQ ID NO:2, wherein each fragment comprises at least 10 contiguous amino acids of the 2',3'-cyclic-nucleotide 3'-phosphodiesterase having the amino acid sequence of SEQ ID NO:2, and no two fragments have an identical amino acid sequence.

* * * * *